US006326184B1

(12) United States Patent
Gjermansen et al.

(10) Patent No.: US 6,326,184 B1
(45) Date of Patent: Dec. 4, 2001

(54) METHOD OF PRODUCING A COMPOSITE FERMENTED BEVERAGE USING GENETICALLY MODIFIED YEAST STRAINS

(75) Inventors: Claes Gjermansen, Niva; Jorgen Hansen, Frederiksberg; Pia Francke Johannesen, Skovlunde; Mogens Bohl Pedersen, Holbaek; Steen Bech Sorensen, Solrod Strand, all of (DK)

(73) Assignee: Carlsberg A/S, Copenhagen (DK)

( * ) Notice: Subject to any disclaimer, the term of this patent is extended or adjusted under 35 U.S.C. 154(b) by 0 days.

(21) Appl. No.: 09/153,310

(22) Filed: Sep. 15, 1998

(51) Int. Cl.$^7$ ............................... C12N 1/16; C12N 1/18; C12N 1/19; C12C 1/00
(52) U.S. Cl. ................................. 435/254.2; 435/254.1; 435/254.21; 435/93; 435/194; 435/254.11
(58) Field of Search ........................... 435/254.2, 254.11, 435/254.1, 254.21, 194, 93

(56) References Cited

U.S. PATENT DOCUMENTS 4,814,188  3/1989  Dziondziak ............................... 426/7

FOREIGN PATENT DOCUMENTS 3616094   11/1987  (EP) .
574 941   12/1993  (EP) .
0699748    6/1996  (EP) .

OTHER PUBLICATIONS

S. Black et al., "A specific enzymatic reduction of L(–) Methionine Sulfoxide and a Related Nonspecific Reduction of Disulfides", J. Bio. Chem., vol. 235:10, (1960), pp. 2910–2916.
D. Botstein et al., "Sterile host yeasts (SHY): A eukaryotic system of biological containment for recombinant DNA", Gene 8 (1979) pp. 17–24.
D. Botstein et al., "Principles and Practice of Recombinant DNA Research with Yeast", pp. 607–636.
A. Breton et al., "Sulfate uptake in Saccharomyces cerevisiae: Biochemical and genetic study", J. Bacter., Oct. 1977, vol. 132, No. 1, pp. 224–232.
P. Briza et al., "Dityrosine is a prominent component of the yeast ascospore wall", J. Biol. Chem. vol. 261, No. 9, Mar. 1986, pp. 4288–4294.
H. Cherest et al., Molecular Characterization of Two High Affinity Sulfate Transporters in Saccharomyces cerevisiae, Genetics 145 (Mar., 1997) pp. 627–635.
G.P. Casey, "Cloning and analysis of two alleles of the ILV3 gene from Saccharomyces carlsbergensis", Carlsberg Res. Commun. vol. 51, (1986), pp. 327–341.
H. Cherest, "Genetic Analysis of a New Mutation Conferring Cysteine Auxotrphy in Saccharomyces cerevisiae: Updating of the Sulfur Metabolism Pathway", Genetics 130, (1992), pp. 51–58.

H. Cherest et al., "Transcriptional regulation of the MET3 gene of Saccharomyces cerevisiae", Gene 34 (1985) pp. 269–281.
C.J. Dickenson, Dimethylsulphide—its origin and control in brewing, J. Inst. Brew. Jan.–Feb., 1983, vol. 89. pp. 41–46.
C.J. Dickenson et al., "The relative importance of S–methylmethionine and dimethyl sulphoxide as precursors of dimethyl sulphide in beer", EBC Congress 1981, pp. 413–420.
J.R. Dickinson et al., "A $^{13}$C Nuclear Magnetic Resonance Investigation of the Metabolism of Leucine to Isoamyl Alcohol in Saccharomyces cerevisiae", J. Biolog. Chem. vol. 272, No. 43, pp. 26871–26878.
P. Drain et al., "Yeast LEU5 is a PET–like gene that is not essential for leucine biosynthesis", Mol. Gen. Genet. (1986) 204, pp. 397–403.
P. Drain et al., "Multiple new genes that determine activity for the first step of leucine Biosynthesis in Saccharomyces cerevisiae", Genetics, 119, (May 1988), pp. 13–20.
T–M. Enari, E.B.C. "Analytica Microbiologica", J. Inst. Brew., Mar.–Apr., 1977, vol. 83, pp. 109–118.
M.T. Elskens et al., "Glutathione as an endogeneous sulphur source in the yeast Saccharomyces cerevisiae", J. Gen. Micro. 137, (1991), pp. 637–644.
P. Friden et al., "LEU3 of Saccharomyces cerevisiae activities multiple genes for branched–chain . . . common decanucleotide core sequence", Mol. and Cell. Biol. (1988), pp. 2690–2697.
T. Fujii et al., "Nucleotide Sequences of Alcohol Acetyltransferase Genes from Lager Brewing Yeast, Saccharomyces carlsbergensis", Yeast Sequencing Reports, vol. 12, (1996), pp. 593–598.
T. Fujii et al., "Acetate Ester Production by Saccharomyces cerevisiae Lacking the ATFI Gene Encoding the Alcohol Acetyltransferase", J. Fermen. and Bio., vol. 81:6, (1996), pp. 538–542.
R.M. Gibson et al., "The influence of assimilable nitrogen compounds in wort on the ability of yeast to reduce dimethylsulphoxide", J. Inst. Brew. Nov.–Dec., 1985, vol. 91, pp. 401–405.

(List continued on next page.)

Primary Examiner—Elizabeth Slobodyansky
Assistant Examiner—Richard Hutson
(74) Attorney, Agent, or Firm—Foley & Lardner

(57) ABSTRACT

Method of preparing a composite yeast fermented beverage such as beer including lager, with predetermined content of flavour compounds, comprising combining separate batches of beverage, of which at least one is a base beverage produced with a yeast strain having reduced or lacking production of one or more flavour compounds or flavour stabilizing compounds. In the method are used yeast strains including S. cerevisiae and S. carlsbergensis which have reduced or lacking production of sulphite, dimethylsulphide, thiols, thioesters, hydrogen sulphide, higher alcohols including isoamyl alcohol and/or alcohol esters.

6 Claims, 33 Drawing Sheets

OTHER PUBLICATIONS

D. Gietz et al., "Improved method for high efficiency transformation of intact yeast cells", Nucleic Acids Research, vol. 20:6, p. 1425, (1992).

C. Gjermansen et al., "Construction of a hybrid brewing strain of *Saccharomyces carlsbergensis* by mating of meiotic segregants", Carlsberg Res. Commun., vol. 46, 1991, pp. 1–11.

C. Hadfield, "Construction of cloning and expression vectors".

C. Hadfield et al., "G418–resistance as a dominant marker and reporter for gene expression in *Saccharomyces cerevisiae*", Current Genetics (1990) 18: pp. 303–313.

J. Hansen et al., "*Saccharomyces carlbergensis* contains two functional MET2 alleles similar to homologues from *S. cerrevisiae* and *S. monacensis*", Gene 140 (1994), pp. 33–40.

J. Hansen et al., Two Divergent MET10 Genes, One from *Saccharomyces cerevisiae* and one from *Saccharomyces carlsbergensis* . . . Binding sites for FAD and NADPH, J. Bact. (1994) pp. 6050–6058.

J. Hansen et al., "Inactivation of MET2 in brewer's yeast increases the level of sulfite in beer", J. Biotech. 50 (1996), pp. 75–87.

J. Hansen et al., "Inactivation of MET10 in brewer's yeast specifically increases $SO_2$ formation during beer production", Nat. Biotech. vol. 14, Nov. 1996, pp. 1587–1591.

C.S. Hoffman et al., "A ten–minute DNA preparation from yeast efficiently releases autonomous plasmids for transformation of *Escherichia coli*", Gene 57 (1987), pp. 267–272.

Y. Hu et al., "The *Saccharomyces cerevisiae* Leu3 protein activates expression of GDH1, a key gene in nitrogen assimilation", Molec. Cell. Biol., Jan. 1995, pp. 52–57.

P.F. Johannesen, "Increasing the flux in the sulfur assimilatory pathway"; Thesis, 1994, pp. 1–114, (Text); pp. 1–63 (Figures).

M.C. Kielland–Brandt et al., "Genetics of Brewing Yeasts", The Yeasts, vol. 6, 2nd edition, (1995) pp. 223–254.

G. Kispal et al., "Mitochondrial and Cytosolic Branched––chain Amino Acid Transaminases from Yeast, Homologs of the myc Oncogene–regulated Eca39 Protein", J. Biol. Chem., 271:40 (1996) pp. 24458–24464.

C. Korch et al., "Cloning, nucleotide sequence, and regulation of MET14, the gene encoding the APS kinase of *Saccharomyces cerevisiae*", Mol Gen. Genet. (1991) 229, pp. 96–108.

T. Langin et al., "The MET2 gene of *Saccharomyces cerevisae*: molecular cloning and nucleotide sequence", Gene. 49 (1986), pp. 283–293.

G.B. Kohlhaw, "α–Isopropylmalate Synthase from Yeast", Methods in Enzymology, vol. 166, (1988), pp. 414–435.

S. Lee et al., "Yeast Strain Development for Enhanced Production of Desirable Alcohols/Esters in Beer", American Society of brewing Chemists, (1995), pp. 153–156.

C. Leemans et al., "Relation between wort DMSO and DMS concentration in beer", EBC Congress (1993), pp. 709–716.

L.E. Low et al., "Quantitation of total sulphur dioxide in beer by automated headspace gas chromatography", EBC Congress (1997), pp. 649–655.

P. Malcorps et al., "Short–chain and medium–chian aliphatic–ester synthesis in *Saccharomyces cerevisae cerevisiae*", J. Biochem. 210, Feb. 1992, pp. 1015–1022.

M.C. Meilgaard, "Flavor Chemistry of Beer: Part II: Flavor and Threshold of 239 Aroma Volatiles", MBAA Technical Quarterly, vol. 12, No. 3, (1975), pp. 151–168.

T. Minetoki et al., "The Purification, Properties and Internal Peptide Sequences . . . Kyokai No. 7", Biosci., Biotech., Biochem., 57 (12), (1993), pp. 2094–2098.

J. Moskovitz et al., "Cloning and expression of a mammalian gene involved in the reduction of methionine sulfoxide residues in proteins", Proc. Natl. Acad. Sci. vol. 93, Mar. 1996, pp. 2095–2099.

J. Moskovitz et al., "The yeast peptide–methionine sulfoxide reductase functions as an antioxidant in vivo", Proc. Natl. Acad. Sci., vol. 94, Sep. 1997, pp. 9585–9589.

H.A. Mountain et al., "Four Major Transcriptional Responses in the Methionine/Threonine Biosynthetic Pathway of *Saccharomyces cerevisiae*", Yeast vol. 7, 1991, pp. 781–803.

K. Nagami et al., "Hydrogen Sulfide in Brewing", MBAA Technical Quarterly, vol. 17, No. 2, (1980), pp. 64–68.

N. Nagasawa et al., Document Reports, Unpublished (1996) (Abstract).

H. Nishimura et al., "A positive regulatory gene, TH13, is required for thiamine metabolism in *Saccharomyces cerevisiae*", J. Bact., Jul. 1992, pp. 4701–4706.

F. Omura et al., "Reduction of Hydrogen Sulfide Production in Brewing Yeast by Consecutive Expression of MET25 Gene", American Society of Brewing Chemists, 1995, pp. 58–62.

T.L. Orr–Weaver et al., "Yeast transformation: a model system for the study of recombination", Proc. Natl. Acad. Sci., vol. 78, No. 10, pp. 6354–6358.

M.B. Pedersen, DNA sequence polymorphisms in the genus Saccharomyces IV. homoelogous chromosomes III of *Saccharomyces bayanus* . . . and S. Uvarum, Carlsberg Res. Commun. vol. 51, 1986, pp. 185–202.

M.B. Pedersen, "The use of nucleotide sequence polymorphisms and DNA karyotyping in the identification of Brewer's yeast strains . . . microbiological control", pp. 180–194.

P.G. Porgue et al., "The involvement of the Thioredoxin System in the Reduction of Methionine Sulfoxide and Sulfate", J. Biol. Chem., vol. 215:9, May 1970, pp. 2371–2374.

M. Atiqur Rahman et al., "Cloning, Sequencing, and Expression of the *Escherichia coli* Peptide Methionine Sulfoxide Reductase Gene", J. Biol. Chem., vol. 267:22, Aug. 1992, pp. 15549–15551.

C. Ramos et al., "Overproduction of Threonine by *Saccharomyces cerevisiae* Mutants Resistant to Hydroxynorvaline", App. Environ. Micro., vol. 58, No. 2, May 1992, pp. 1677–1682.

C. Ramos et al., "Formation of aromatic and kinetic absorption substances from amino acids of wort", pp. 505–519.

E.H.A. Rikkerink et al., "Opaque–White Phenotype Transition: a Programmed Morphological Transition in *Candida albicans*", J. Bacter., vol. 170:2, Feb. 1988, pp. 895–899.

R. Rothstein, "Targeting, Disruption, Replacement, and Allele Rescue Integrative DNA Transformation in Yeast," Methods in Enzymology, vol. 194, 1991, pp. 281–301.

J. Sambrook et al., "Analysis and Cloning of Eukaryotic Genomic DNA", Molecular Cloning A Laboratory Manual 2nd Ed., 1989, 34 pages.

S. Sangsoda et al., "The expression of the MET25 gene of *Saccharomyces cerevisiae* is regulated transcriptionally", Mol. gen. genet (1985) 200: pp. 407–414.

T. Satoh et al., "Purification and properties of dimethysulfoxide reductase containing a molybdenum cofactor from a photodenitrifier . . .", J. Biochem. 102, (1987), pp. 191–197.

A.B. Schaeffer et al., "Scientific Apparatus and Laboratory Methods", Science, vol. 77, 1990, 1 page.

S. Scherer et al., Replacement of chromosome segments with altered DNA sequences constructed in vitro, Proc. Natl. Acad. Sci. vol. 76:10, Oct. 1979, pp. 4951–4955.

R.H. Schiestl et al., "High efficiency transformatio of intact yeast cells using single stranded nucleic acids as a carrier", Curr. Genet. (1989) 16:339–346.

G.D. Schuler et al., "A workbench for multiple alignment construction and analysis", Proteins: Structure, Function and Genetics 9:180–189 (1991).

D.C. Schwartz et al., "Separation of Yeast Chromosome-Sized DNAs by Pulsed Field Gradient Gel Electrophoresis", Cell, Vos. 37, pp. 67–75, May 1984.

F. Sherman, "Getting started with yeast", Methods in enzymology, vol. 194, 1991, pp. 3–21.

F. Sherman et al., "Methods in Yeast genetics", Appendix A, pp. 61–64.

P. Sigsgaard et al., "Screening of the Brewing Performance of New Yeast Strains", ASBC Journal, Vo. 43, No. 2, 1985, pp. 104–108.

R.S. Sikorski et al., "A System of Shuttle Vectors and Yeast Host Stains Designed for Efficient Manipulation of DNA in *Saccharomyces cerevisiae*", Genetics 122, May 1989, pp. 19–27.

R.A. Singer et al., "Methionine nalogs and cell division regulation in the yeast *Saccharomyces cerevisiae*", Proc. Natl. Acad. Sci. vol. 75, No. 12, Dec. 1978, pp. 6083–6087.

T. Takahashi et al., "Hydrogen Sulfide in Brewing—II", MBAA Technical Quarterly, vol. 17, No. 4, 1980, pp. 210–214.

H. Tezuka et al., "Cloning of a Gene Suppressing Hydrogen Sulfide Production by *Saccharomyces cerevisiae* and its Expression in a Brewing Yeast", ASBC Journal, vol. 50, No. 4, pp. 130–133.

D. Thomas et al., "Gene–enzyme Relationship in the Sulfate Assimilation Pathway of *Saccharomyces cerevisiae*", J. Biol. Chem. vol. 265, No. 26, Sep. 1990, pp. 15518–15524.

D. Thomas et al., "Physiological analysis of mutants of *Saccharomyces cerevisiae* impaired in sulfate assimiliation", J. General Microbiology 138 (1992), pp. 2021–2028.

D. Thomas et al., "Elements involved in S–adenosylmethionine–mediated regulation of the *Saccharomyces cerevisiae* MET25 Gene", Mol. Cell. Bio. Aug. 1989, pp. 3292–3298.

J.H. Weiner et al., "Molecular analysis of dimethylsulfoxide reductase: a complex iron–sulfur molybdoenzyme of *Escherichia coli*", Biochem. Biophys. 1102 (1992) 1–18.

C. Yanisch–Perron et al., "Improved M13 phage cloning vectors and host strains: nucleotide sequences of the M13mp18 and pUC19 vectors", Gene. 33 (1985), pp. 103–119.

H. Yoshimoto, "Cloning and characterization of the ATF2 gene encoding alcohol acetyltransferase in the bottom fermenting yeast *Saccharomyces pastorianus*", Unpublished (1996) (Abstract), 2 pages.

H. Yoshimoto et al., 1996 Yeast Genetics and Molecular Biology Meeting, (Abstract) 2 pages.

S.H. Zinder et al., "Dimethyl sulphoxide reduction by micro–organisms", J. Gen. Microbio. (1978) 105, pp. 335–342.

S.H. Zinder et al., "Dimethyl Sulfoxide as an Electron Acceptor for Anearobic Growth," Arch. Microbiol. 116, (1978), pp. 35–40.

I. Yamamoto et al., "Cloning and Nucleotide Sequence of the Gene Encoding Dimethyl Sulfoxide Reductase from *Rhodobacter sphaeroides* f. sp. denitrificans", Biosci, Biotech, Biochem. 59, pp. 1850–1855.

B.J. Anness, "The Reduction of Dimethyl Sulphoxide to Dimethyl Sulphide During Fermentation", *J. Inst. Brew.*, May–Jun., 1980, vol. 86, pp. 134–137.

B.J. Anness et al., "Dimethyl Sulphide—A Review", *J. Inst. Brew.*, Jul.–Aug., 1982, vol. 88, pp. 244–252.

B.J. Anness et al., "The Measurement of Dimethyl Sulphoxide in Barley and Malt and its Reduction to Dimethyl Sulphide by Yeast", *J. Inst. Brew.*, Nov.–Dec., 1979, vol. 85, pp. 346–349.

L. Atkin et al., "Use of the Specific Gravity Gradient Tube for Brewery Control", Wallerstein Communication, vol. XI, No. 35, Dec. 1948, pp. 281–288.

V.R. Baichwal et al., "Leucine Biosynthesis in Yeast", Current Genetics (1983), 7:369–377.

C.W. Bamforth, "Dimethyl Sulphoxide Reductase of *Saccharomyces SPP.*", FEMS Microbiology Letters 7 (1980) pp. 55–59.

C.W. Bamforth et al., "Dimethy Sulphoxide Reuction by Yeast"; Brewing Research Foundation, vol. 87, 1981, pp. 32–34.

C.W. Bamforth et al., "The role of diemethy sulphoxide reductase in the formation of dimethyl sulphide during fermentations", *J. Inst. Brew.* Jan.–Feb., 1981, vol. 87, pp. 30–34.

P.T. Bilous et al., "Nucleotide sequence of the dmsABC operon encoding the anaerobic dimethyl–sulpphoxide reductase of *Escherichia coli*", Mol. Micro. (1988) 2(6), 785–795.

Fitzgerald–Hayes et. al., Isolation and Subcloning Analysis of Functional Centromere DNA (CEN11) from *Saccharomyces cerevisiae* Chromosome XI, Molecullar and Cellular Biology 2: 82–87, Jan. 1982.*

Xu et al., Isolation and characterization of sulfite mutants of *Saccharomyces cerevisiae*, Curr. Genet. 25: 488–496, 1994.*

Christopher Korch, et al.; *A Mechanism For Sulfite Production In Beer And How To Increase Sulfite Levels By Recombinant Genetics*; Jan. 1, 1991; (XP–002066286) Yeast & Fermentation, pp. 201–208.

* cited by examiner

```
GGATCCGAAA GGTGGCCTAT CAAAACAAAT TAACTTCCAC ATAACTGGAA GGCAGCAAAG  60
ATATGTCAGC AAAGACATGT TAGCTTGGTA GTGAAGTTTC TTGTTTTTTA CCTACAAAAC 120
GCCCCGCGCT GTTTTCTCAA TGTTGGAACA AAAAGCGTGC CACTAATTCC ACGTGATTAA 180
TGTCTGCAAG CCACCCCAAA AATTGTGGCT AGTATAGAAG ATGATGAACT CAACATTACT 240
TTAATTTCAT GAATTTTCTG AGGGCGTGTG TATAAAACGC AGATGTTCTC GACAACTTTA 300
CTGTACAAAC TTTACTCTTC TGCTGTAGCT AAATTTTAAA ATGAGTAGGA ACATTTTCGT 360
GAAATTCATT GAAACAAATG GCTACTAATA TCACTTGGCA TCCAAATCTT ACCTACGACG 420
AACGTAAGGA ATTAAGAAAG CAAGACGGCT GTACCGTTTG GTTGACCGGT CTAAGTGCGT 480
CAGGAAAAAG TACAATAGCT TGTGCACTGG AACAATTACT GCTTCAAAAA AACTTATCTG 540
CTTATAGGTT AGATGGTGAT AACATTCGTT TTGGTTTGAA TAAGGATTTG GGCTTCTCAG 600
AAAAGGACAG AAATGAAAAC ATTCGTAGAA TTAGTGAAGT ATCCAAGCTA TTCGCTGATT 660
CGTGTGCTGT ATCCATCACT TCATTTATTT CCCCATACAG AGTCGATAGA GACAGAGCCC 720
GTGATTTACA TAAGGAAGCA GGCTTGAAGT TCATTGAAAT TTTTGTTGAT GTTCCATTAG 780
AAGTCGCTGA GCAAAGAGAC CCTAAGGGTT TGTATAAGAA AGCCAGAGAA GGTGTGATTA 840
AAGAGTTCAC TGGTATTTCA GCTCCTTACG AAGCTCCAAA GGCCCCAGAG TTGCATTTAA 900
GAACTGACCA AAAGACTGTT GAAGAATGTG CTGCTATCAT TTATGAGTAC CTGGTCAATG 960
AGAAGATTAT CCGGAAGCAT CTATAAATCT TATAAATTGC ATTTAATGAT ATAAAGATG 1020
TATAATAGAA AACGTATTTA TTTAAAAGCC CATTCAAGAG CATTGAAAAC TGTAAATAAT 1080
GAGGAGGATG GTATAATAAA TGGTTTTAAA GTTTCACACA CTGTATCCTA TATTAGATAT 1140
TTAGTACCGA CTCCGGATCC                                            1160
```

Fig. 4 a.
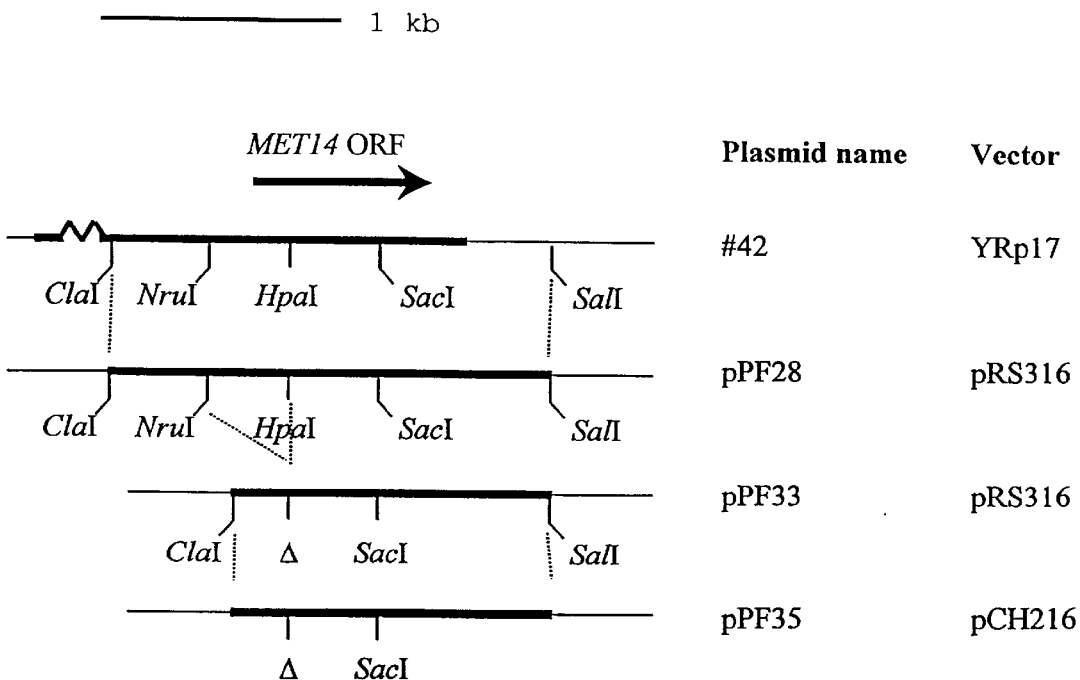
b.
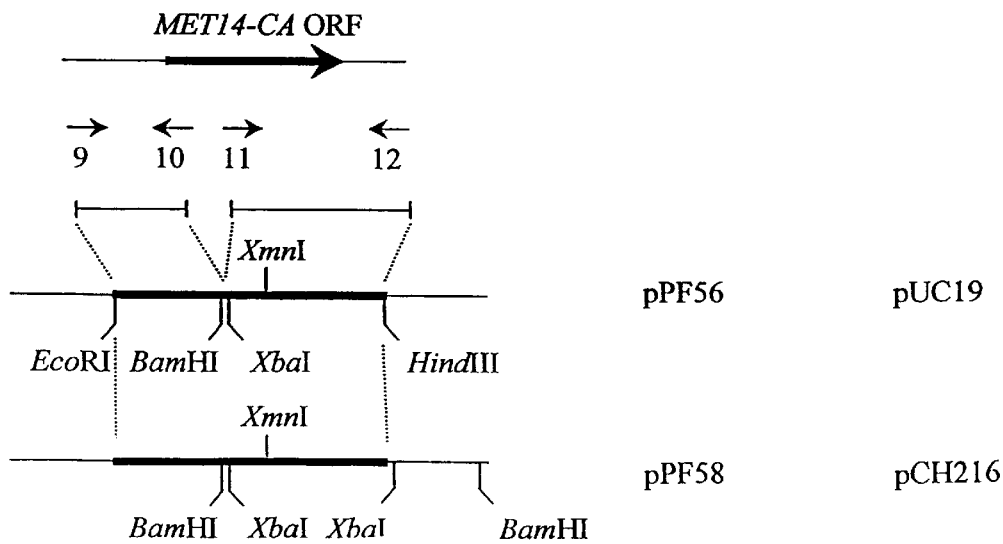
Fig. 5

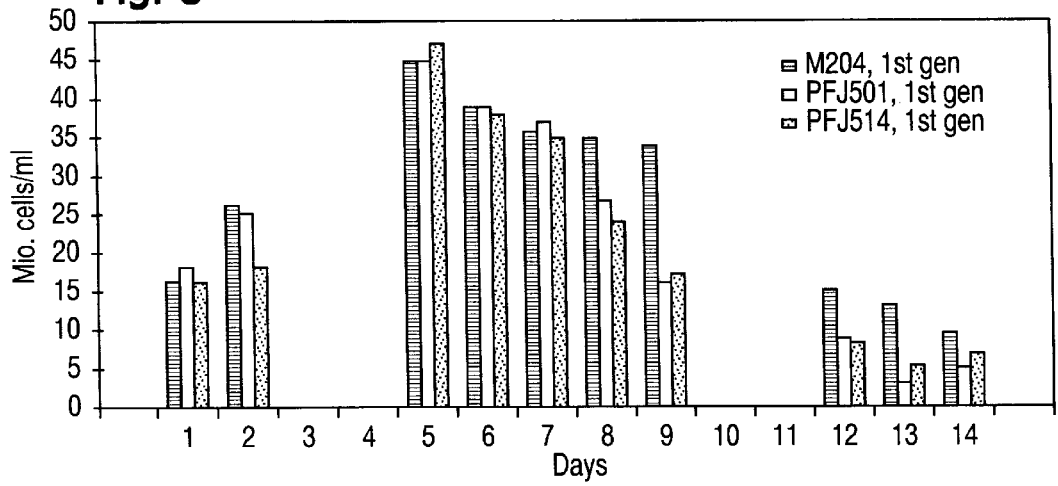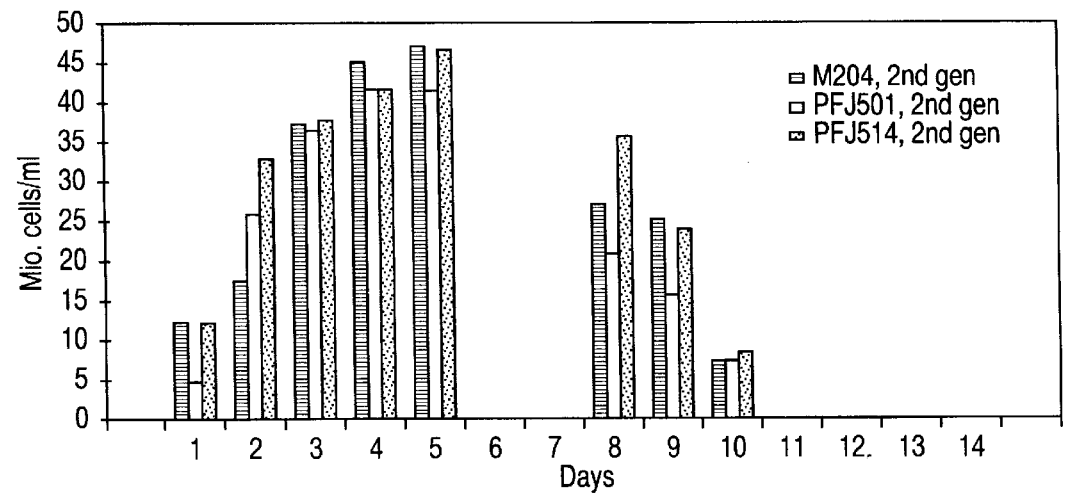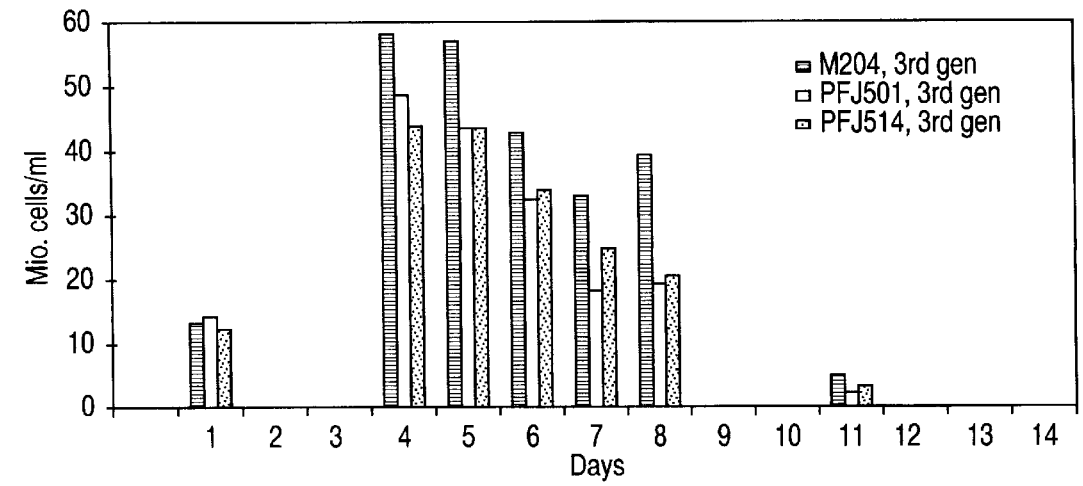
Fig. 8

```
         10        20        30        40        50
         |    .    |    .    |    .    |    .    |
MVKESIIALAEHAASRASRVIPPVKLAYKNMLKDPSSKYKPFNAPKLSNR      50
KWPDNRITRAPRWLSTDLRDGNQSLPDPMSVEQKKEYFHKLVNIGFKEIE     100
VSFPSASVCLFDFTRYAVENAPDDVSIQCLVQSREHLIKRTVEALTGAKK     150
ATIHTYLATSDMFREIVFNMSREEAISKAVEATKLVRKLTKDDPSQQATR     200
WSYEFSPECFSDTPGEFAVEICEAVKKAWEPTEENPIIFNLPATVEVASP     250
NVYADQIEYFATHITEREKVCISTHCHNDRGCGVAATELGMLAGADRVEG     300
CLFGNGERTGNVDLVTVAMNMYTQGVSPNLDFSDLTSVLDVVERCNKIPV     350
SQRAPYGGDLVVCAFSGSSHQDAIKKGFNLQNKKRAQGETQWRIPYLPLDP    400
KDIGRDYEAVIRVNSQSGKGGAAWVILRSLGLDLPRNMQIEFSSAVQDHA     450
DSLGRELKSDEISKLFKEAYNYNDEQYQAISLVNYNVEKFGTERRVFTGQ     500
VKVGDQIVDIEGTGNGPISSIVDALSNLLNVRFAVANYTEHSLGSGSSTQ     550
AASYIHLSYRRNADNEKAYKWGVGVSEDVGDSSVRAIFATINNIIHSGDV     600
SIPSLAEVEGKNAAASGSA                                   619
```

Fig. 23

Integration plasmid pSBS97-1
3760 bp

Integration plasmid pSBS97-2
3953 bp

Integration plasmid pSBS97-3 and pSBS97-6
5858 bp

Integration plasmid pSBS97-4 and pSBS97-7
5797 bp

Integration plasmid pSBS97-5 and pSBS97-8 5539 bp

US 6,326,184 B1

METHOD OF PRODUCING A COMPOSITE FERMENTED BEVERAGE USING GENETICALLY MODIFIED YEAST STRAINS

FIELD OF INVENTION

The invention relates to the field of yeast fermented beverages including beer, sake, wine and whisky and in particular the invention is concerned with the provision of customized composite yeast fermented beverages having a predetermined content of flavour compounds and/or flavour compound stabilizing compounds, which are made by combining two or more separate batches of yeast fermentates each having different contents of yeast-generated flavour compounds and/or compounds that are capable of stabilizing such flavour compounds. The invention also provides novel, genetically modified yeast strains that are useful in the invention.

Specifically, the invention has made it possible to make a composite yeast fermented beverage product such as lager beer having a predetermined content of one or more flavour compound(s) and/or compound(s) that stabilize(s) flavour compounds e.g. by providing at least one batch of fermented beverage which is produced by using a yeast strain which is modified to substantially not produce at least one flavour compound and/or compound stabilizing flavour compounds (base batch of fermentate) and combining such a batch with one or more batches of beverage fermentates that contain(s) a level of flavour compounds and/or stabilizing compounds which is normal for a fermentate produced by using a conventional yeast strain or which is produced by a modified yeast strain having, relative to conventionally used yeast strains, an enhanced production of at least one flavour compound or flavour compound stabilizing compound.

TECHNICAL BACKGROUND AND PRIOR ART

The sensory quality of a yeast fermented beverage such as beer depends largely on the particular brewing yeast strain which is used. During the beer brewing process, the yeast will in addition to ethanol produce a large variety of minor metabolites which affect the taste and flavour of the beer. Whereas the presence of certain of such minor metabolites may, at least up to certain levels, confer desirable sensory characteristics to the beer, several minor metabolites are undesired and may even, if present in higher amounts, result in spoilage of the beer.

Yeast fermented beverages including beer contain more than a hundred minor metabolites, of which some, at least when they are present above certain concentrations, will confer to the beverage an undesirable taste and flavour. A comprehensive review of beer flavouring compounds has been given by Meilgaard (1975) to which there is referred. In this connection, the most important metabolites include sulphur compounds such as dimethyl sulphide (DMS), hydrogen sulphide ($H_2S$), thiols and thioesters which at certain levels will result in undesirable sulphur-containing flavours.

DMS is a thioether of great importance for the aroma and flavour of beer. The content of DMS in conventional lager beers regularly exceeds the taste threshold level of about 30 μg/L (Meilgaard, 1975) which explains the focus that has been on this compound. Above its threshold level but below about 100 μg/L DMS contributes to the distinctive taste of some lager beers. When present at concentrations above 100 μg/L DMS may, however, impart a generally undesired flavour described as "cooked sweet corn". DMS in beer may be derived from thermal degradation of S-methyl-methionine during kiln-drying and wort preparation and it has been suggested that this is the only pathway of significance for the final DMS content in beer (Dickenson and Anderson, 1981; Dickenson, 1983). However, substantial evidence suggests that enzymatic conversion of dimethyl sulphoxide (DMSO) to DMS by the brewing yeast is of great importance and, under some circumstances, even the major source of the final DMS level in beer (Leemans et al., 1993).

There is no doubt, that Saccharomyces strains do contain an enzymatic activity that can reduce DMSO to DMS in a NADPH-dependent manner (Zinder and Brock, 1978a; Anness et al., 1979; Anness, 1980). A multicomponent methionine sulphoxide (MetSO) reductase (EC 1.8.4.5) has been isolated from yeast (Black et al., 1960; Porqué et al., 1970), and it has been suggested that this activity is identical to the DMSO reductase activity (Anness et al., 1979; Anness, 1980; Bamforth, 1980; Bamforth and Anness, 1979; 1981). The normal function of MetSO reductase seems to be reduction of oxidized methionines of cellular proteins which is in agreement with observations showing that the enzyme has a higher affinity for MetSO than for DMSO (Bamforth and Anness, 1979; 1981) and that MetSO inhibits DMSO reduction (Anness et al., 1979; Anness, 1980; Bamforth and Anness, 1981). The consequence hereof is that the degree of MetSO formation during kiln-drying of the malt will affect the degree of DMSO reduction.

The nitrogen content of the growth medium also seems to affect DMS formation by yeast. Thus, high amounts of highly assimilable nitrogen keep DMSO reductase activity at a low level, whereas enzyme activity is induced under nitrogen-limiting conditions (Gibson et al., 1985). The high nitrogen content of most worts would appear to keep DMSO reduction at the base level during fermentation. See Anness and Bamforth (1982) for a review on DMS formation in beer production. So-called DMSO reductases from some prokaryotes have been characterized, as well as the genes encoding them (Satoh and Kurihara, 1987; Bilous et al., 1988; Weiner et al., 1992; Yamamoto et al., 1995). While such enzymes, in some cases, have MetSO reducing capabilities, their main purpose in the bacterial cell is probably to act as the terminal step in DMSO respiration (Zinder and Brock, 1978b). Peptide methionine sulphoxide reductases (PMSRs) probably fulfil the role of repairing oxidised methionine species in proteins, thereby restoring their biological activity.

Sulphite is another sulphur-containing metabolite being formed during yeast fermentation. Sulphite is a versatile food additive used for preservation of foodstuffs. In beer sulphite has a dual activity in that it acts both as an antioxidant and as an agent that masks certain off-flavours. Due to its great importance, considerable work has been carried out to elucidate the physiology of sulphur metabolism in Saccharomyces species in relation to sulphite production.

Sulphite is produced by the yeast during beer fermentation and is present in the final beer. The compound is produced via the sulphur assimilation pathway. Inorganic sulphate is taken up through two sulphate permeases encoded by SUL1 and SUL2, respectively (Cherest et al., 1997). Intracellularly, sulphate is converted to adenylylsulphate (APS) by the action of ATP sulphurylase (EC 2.7.7.4) encoded by MET3. In a subsequent step, the MET14 encoded APS kinase (EC 2.7.1.25) catalyses the formation of phosphoadenylylsulphate (PAPS) which in turn is reduced by PAPS reductase (EC 1.8.99.4) (MET16 encoded) to sulphite.

Hydrogen sulphide results from reduction of sulphite and in this form inorganic sulphur is incorporated into organic compounds by fusion with O-acetyl homoserine leading to the formation of homocysteine. The latter compound is the precursor for biosynthesis of cysteine, methionine and S-adenosylmethionine (SAM). SAM represses transcriptionally all MET-genes (Cherest et al., 1985; Sangsoda et al., 1985; Langin et al., 1986; Thomas et al., 1989; Thomas et al., 1990; Korch et al., 1991; Mountain et al., 1991; Hansen et al., 1994).

Hydrogen sulphide is, as it is mentioned above, an intermediate in the sulphur assimilatory pathway of Saccharomyces spp. It is also the point of entry into the methionine biosynthetic pathway of carbon backbones derived from the threonine biosynthetic pathway. It is derived in four enzymatic steps from inorganic sulphate ions obtained from the growth medium of the yeast.

Besides being an intermediate in the yeast sulphur metabolism, hydrogen sulphide is an important flavour compound in beer and its distinct taste of "putrefied eggs" generally renders this compound undesired in beers, except at very low concentrations, where it may aid in disguising the taste of other flavour compounds such as acetyl esters.

Several workers have attempted to control the formation of hydrogen sulphide in beer production by modifying yeast strains by recombinant DNA technology. Thus, overexpression of the MET25 gene encoding the enzyme (EC 4.2.1.22) that catalyses the condensation of hydrogen sulphide and O-acetyl homoserine leads to a reduced hydrogen sulphide concentration in beer (Omura et al., 1995). When the gene NSH5 (STR4, CYS4) encoding the first of two steps (EC 4.2.1.22) in formation of cysteine from homocysteine is overexpressed, the hydrogen sulphide level is also reduced (Tezuka et al., 1992). This effect was suggested by these authors to be due to faster removal of homocysteine and thus of its precursor, hydrogen sulphide. These experiments suggest the existence of metabolic bottlenecks around the conversion of hydrogen sulphide into organic sulphur compounds. In the literature, there have been speculations that hydrogen sulphide may be a precursor for certain thiols and thioesters, e. g. methane- and ethanethiol (MeSH and EtSH) and methyl- and ethylthioacetate (MeSAc and EtSAc). Thus, in the above experiment with NSHS (Tezuka et al., 1992), the decrease in hydrogen sulphide production was followed by a decrease in methanethiol and ethanethiol production.

Another group of flavour compounds which, when present above certain threshold levels, result in undesirable flavours include higher alcohols and esters such as ethyl acetate, isoamyl acetate and ethyl hexanoate. Above their threshold levels such esters will confer a fruity (apple, banana) flavour to beer.

A variety of higher alcohols is found in beer. As used herein "higher alcohols" indicate other alcohols than ethanol. Such higher alcohols that are also referred to in the art as fusel alcohols are listed in Meilgaard (1975) and include isoamyl alcohol.

Some of the higher alcohols are produced by metabolism of the branched chain amino acids isoleucine, valine and leucine. α-Ketoacids (α-keto-β-methylvalerate, α-ketoisovalerate and α-ketoisocaproate) are important intermediates for branched-chain amino acids as well as for higher alcohols. Isoamyl alcohol and its corresponding acetate ester are among the distinct beer flavour components.

Three enzymatic steps encoded by the genes LEU4 (Baichwal et al. 1983), LEU1 and LEU2 are involved in de novo synthesis of α-keto-isocaproate. The enzymes are α-isopropylmalate (αIPM) synthase (Leu4p, EC 4.1.3.12), isopropylmalate isomerase (Leu1p, EC 4.2.1.33) and β-isopropylmalate dehydrogenase (Leu2p, EC 1.1.1.85) (Reviewed by Kohlhaw, 1988). The pathway is regulated by a complex consisting of the regulatory protein Leu3p and isopropylmalate. The complex acts as an activator and regulates the level of mRNA being produced by binding to a regulatory region in front of the LEU4, LEU1 and LEU2 coding regions. Conversion of α-ketoisocaproate to leucine is catalyzed by the transaminases encoded by the genes BAT1 and BAT2. Deletion of both BAT1 and BAT2 results in auxotrophy for the branched-chain amino acids isoleucine, valine and leucine (Kispal et al. 1996).

In the yeast cell, the leucine level is regulated in several ways, of which feed-back inhibition of the isopropylmalate synthase by leucine is one. It is possible to inactivate the feed-back inhibition of Leu4p. Leucine feed-back inhibition resistant mutants with a dramatically lower sensitivity for leucine have been isolated. The mutants are resistant to the leucine analogue 5,5,5-trifluoro-DL-leucine (TFL). LEU4 was originally isolated as a mutant resistant to TFL (Baichwal et al. 1983). Such dominant feed-back resistant (LEU4$^{fbr}$) mutations are known to produce high amounts of isoamyl alcohol and isoamyl acetate in brewers yeast (Lee et al. 1995).

Previous studies have shown that at least three isopropylmalate synthases are present in the yeast cell (Baichwal et al. 1983). Two synthases are produced by LEU4 (80% of the wild-type activity). The two forms produced by LEU4 include a long form (designated Ia) that is exported to the mitochondria and a short form designated Ib present in the cytoplasm. The gene coding for the remaining activity was originally designated LEU5, but later investigations have shown LEU5 to be a gene with PET gene similarities (petites: unable to grow on non-fermentable carbon sources) (Drain and Schimmel, 1986) and not directly involved in the leucine synthesis pathway. Inactivation of the LEU4 gene product does not in itself lead to leucine auxotrophy (Baichwal et al. 1983). The leu4 (leaky) phenotype might be due to other synthase activities. Three other loci (LEU6, LEU7 and LEU8) responsible for leucine biosynthesis have been described, where LEU7 and LEU8 appear to be candidates for a gene or genes that encode an α-IPM synthase activity (Drain and Schimmel, 1988). Linkage to known open reading frames has not yet been established.

During the Saccharomyces cerevisiae genome-sequencing project (http://genome-www.stanford.edu/Saccharomyces/), a putative LEU4 homologue has been identified. The open reading frame (ORF) is designated YOR108W and is located on chromosome XV. The ORF YOR108W is homologous to LEU4 with more than 80% nucleotide identity in a contiguous sequence of 1806 nucleotides of 1860 nucleotides found in the LEU4 ORF, whereas the upstream regulatory regions are clearly different. There appears to be a possibility for translation of a long and a short form similar to LEU4. Upstream of the YOR108W ORF two regulatory Gcn4p and Leu3p binding sequences seem to be present.

An α-ketoisocaproate decarboxylase activity encoded by the ORF YDL080C has been described for S. cerevisiae (Dickinson et al., 1997). This ORF is most likely the same as THI3 (Nishimura et al., 1992). The enzyme appears to catalyze the conversion of α-ketoisocaproate to isoamyl alcohol. In a ydl080 disruptant a minor activity (40% activity relative to that of the wild type) appears to be present.

Two alcohol acetyltransferase genes designated ATF1 (ORF YOR377W on chromosome XV) and ATF2 (ORF YGR177C on chromosome VII) have been identified in *S. cerevisiae*. Alcohol acetyl-transferases (AATases EC 2.3.1.84) catalyze the transfer of the acetyl group from acetyl-CoA to alcohols thereby producing acetate esters. AATase1 encoded by the ATF1 gene has been purified (Malcorps & Dufour,1992 and Minetoki et al., 1993), while AATase2 is only known as an open reading frame, ATF2 (Nagasawa et al., 1995). AATase1 and AATase2 have about 36% amino acid sequence identity. The ATF1 gene has been disrupted (Fujii et al. 1996b). This mutant produced about 20% isoamyl acetate and about 60% ethyl acetate as compared to the original strain (Fujii et al. 1996b).

The allotetraploid lager yeast, *Saccharomyces carlsbergensis*, has at least two different genomic sets. One genomic set is similar to that of *S. cerevisiae* whereas another genomic set is similar to that of *S. monacensis* (Pedersen, 1986). Allotetraploid lager yeast thus has two copies of a *S. cerevisiae*-like allele of ATF1 (designated herein as ATF1-CE), and two copies of a *S. carlsbergensis* specific allele (designated herein as ATF1-CA), presumably originating from *S. monacensis*. Fujii et al. (1996a) cloned the two genes ATF1-CE and ATF1-CA (previously designated ATF1 and Lg-ATF1, respectively) and determined the nucleotide sequence. The amino acid sequences encoded by the two genes are 76% identical. The ATF2-CE gene from the bottom fermenting yeast *Saccharomyces pastorianus* has been cloned and sequenced (Yoshimoto et al., 1996a, 1996b). It is not known whether two forms of this gene are found in the *S. carlsbergensis* lager yeast. Fermentation of wort with a brewers yeast transformed with a 2 μ-based plasmid containing the ATF1-CE gene resulted in increased levels of isoamyl acetate (7.6-fold) and ethyl acetate (3.9-fold) in the final beer compared to the control (Fujii et al., 1993).

Abnormal flavours may also be associated with various ketones of which diacetyl is the most important and with aldehydes such as acetaldehyde, the precursor for ethanol, and so-called staling aldehydes of which the most important is trans-2-nonenal which confer to beer a highly undesired "cardboard" flavour.

Currently, the brewing industry attempts to control the sensory quality of beer such as lager by several measures, including blending of batches having an undesired content of one or several metabolites with batches having a lower content hereof. However, when using conventional strains of brewer's yeast, it may not be possible to obtain a fully acceptable blend of beer by this approach. An alternative approach is to select, by using classical breeding and mutagenization techniques, yeast strains which, relative to the conventionally used strains, have a lower production of an undesired metabolite.

The most widely used yeast for brewing is Saccharomyces spp. However, not all Saccharomyces spp. are suitable for brewing purposes. Typical faults of non-brewing Saccharomyces strains include production of phenolic off-flavour, inability to utilize maltotriose and low fermentation rate at the temperature optimal for the desired aroma of the beer.

In the industry, the characteristics of the existing brewing yeasts may be improved by selecting strains which e.g. have a higher rate of fermentation, a decrease in beer maturation time, better flocculation characteristics or increased tolerance to alcohol.

There are, however, two major factors that currently limit progress in the breeding of brewing yeasts. First, it is often complicated to translate the desired change in yeast performance into biochemical and genetic terms. The second difficulty is that brewing yeasts generally have deficiencies in their sexual reproduction and as a consequence hereof it is difficult to carry out many of the breeding steps and procedures in genetic analysis that are trivial with the non-brewing yeasts used as genetic reference strains in academic studies.

Although the designation *Saccharomyces carlsbergensis* is widely accepted, this common lager yeast is also conventionally referred to as *S. pastorianus* or *S. uvarum*. It has a complicated genetic structure, being allotetraploid with one chromosome set similar to the *S. cerevisiae* genome while the other set is structurally similar to that of *S. monacensis*. Therefore, it is expected to find two copies of a *S. cerevisiae*-like allele and two copies of a *S. monacensis*-like allele of a certain gene in *S. carlsbergensis*. Hereinafter, the *S. cerevisiae*-like allele is specified by the gene name followed by -CE (e.g. MET2-CE). Similarly, the *S. carlsbergensis*-specific (*S. monacensis*-like) allele is designated by the gene name followed by -CA. It is generally assumed that this "mixed" genome may have an effect on the characteristics of the lager brewing yeast. Strain improvement by classical genetic methods is not straightforward, as most brewing yeasts exhibit poor sporulation and low spore viability.

It is therefore currently a significant problem in the brewing industry that it is impossible or difficult to provide a range of variants of the same beverage type such as lager beer which are specifically adapted to consumer preferences in individual marketplaces or to different seasons of the year by having specific and predetermined contents of compounds determining the sensory characteristics of the beverages.

Methods to make fermented beverages having a modified content of aroma or flavour compounds have been developed. One approach which has been used to modify beverages is to add isolated and/or concentrated aroma or flavour compounds derived from a yeast fermentation process and using such compounds as flavour additives to beverages. Thus, as an example, it is suggested in U.S. Pat. No. 3,713,838 to produce food products and beverages to which are added flavour compounds isolated from yeast dregs from a conventional brewing process. In WO 96/39480 is disclosed the use of kettle hop extracts to provide a fully hop flavoured beverage Another approach is to provide yeast strains which have been modified to produce an increased level of particular flavour compounds. Thus, EP 574 941-Al discloses *Saccharomyces cerevisiae* strains transformed with a plasmid-borne gene coding for alcohol acetyltransferase (AATase). Such transformed strains having multiple copies of this AATase-encoding ATF1 gene showed an enhanced production of isoamyl acetate and ethyl acetate.

In WO 94/08019 is disclosed microbial strains which are transformed with a gene coding for α-acetolactate decarboxylase, an enzyme capable of converting the diacetyl precursor, α-acetolactate, directly to acetoin, thus avoiding the formation of diacetyl.

JP 62-92577 and 30-07579 disclose mutants of *Saccharomyces cerevisiae* that have enhanced production of amyl alcohol and isobutyl alcohol, whereas JP 50-49465 discloses yeast mutant strains producing high amounts of β-phenethylene alcohol and esters thereof.

There have been very few attempts to provide brewing yeast strains including *S. carlsbergensis* having a reduced production of flavour compounds. Thus, it has been attempted to control the production of diacetyl by blocking the acetolactate synthase activity in *Saccharomyces cerevisiae* by mutation or in *Saccharomyces carlsbergensis* by in vitro deletion and replacement by recombination of ILV2 genes with the mutant alleles. However, completely blocking this biosynthetic step in *Saccharomyces carlsbergensis* has not yielded brewing strains with satisfactory characteristics, presumably because the parental strains herefor do not take up isoleucine and valine as effectively as *Saccharomyces cerevisiae* (Kielland-Brandt et al. 1995).

Thus, the prior art is not aware of industrially suitable strains of brewer's yeast in which pathways for production of undesired metabolites have been substantially completely interrupted or of strains of the lager brewing yeast *Saccharomyces carlsbergensis* that has been modified to produce in the brewing process none or less of a flavour compound and/or a compound that stabilizes a flavour compound.

It has now been found that it is possible to provide modified Saccharomyces brewer's yeast strains including modified strains of *Saccharomyces carlsbergensis* in which one or several biosynthetic pathways leading to the formation of flavour compounds or compounds stabilizing such compounds have been substantially completely blocked and that such modified strains have retained the beverage fermentation capacity and efficiency of the parent strains.

This has provided industrially attractive means for producing yeast fermented beverages including lager beers which substantially do not contain one or more flavour compounds or flavour stabilizing compounds that is/are normally produced by the lager yeast strain. In turn, this achievement has made it possible to produce, in an industrial production scale, a fermented base beverage in which one or more flavour-related metabolite(s) normally present in a particular beverage type is/are absent or present at very low levels. Such a base beverage can in turn be "flavour customized" by blending it with batches of beverage having a normal or enhanced content of the respective flavour compounds or by adding isolated flavour compounds to provide a composite beer having a desired, predetermined flavour compound profile.

SUMMARY OF THE INVENTION

Accordingly, the present invention relates in a first aspect to a method of preparing a composite yeast fermented beverage having a predetermined content of flavour compounds or compounds stabilizing the flavour of said beverage, the method comprising (i) producing separate batches of fermented beverage using a different strain of yeast for each batch, at least one of said batches being a fermented base beverage produced with a yeast strain which is modified by mutation or recombination to have, relative to the parent strain from which it is derived, a reduced or lacking production of at least one flavour compound or of at least one compound that is capable of stabilizing the flavour of said composite yeast fermented beverage by forming adducts with staling compounds present therein, (ii) optionally followed by at least partially dehydrating one or more of said separate batches or isolating therefrom a flavour or stabilizing-compound, and (iii) combining said batches and/or isolated compounds to obtain the composite beverage.

In useful embodiments of the above method the composite beverage comprises at least one batch of beverage that is produced by using a yeast strain which is not mutationally or recombinationally modified in respect of production of flavouring or flavour stabilizing compounds. and/or at least one batch of fermented beverage that is produced by using a yeast strain which is modified by mutation or recombination to have, relative to the parent strain from which it is derived, an enhanced production of a flavour compound or of a compound that is capable of stabilizing the flavour of the composite yeast fermented beverage by forming adducts with staling compounds present therein.

In further aspects, the invention pertains to a composite beverage obtainable by the above method and to the use of a batch of yeast fermented beverage produced by a modified yeast having an enhanced flavour compound production, or a flavour compound isolated from such a batch, as a flavouring agent.

In still further aspects, there are provided a genetically modified yeast strain which, relative to its parent strain, has a reduced or lacking production of sulphite during production of a fermented beverage and a method of producing a yeast fermented beverage using such a modified yeast strain, a genetically modified yeast strain which, relative to its parent strain, has a reduced or lacking capability of converting dimethyl sulphoxide into dimethyl sulphide, and a method of producing a fermented beverage using such a modified strain.

In another aspect there is provided a novel non-recombinantly modified *Saccharomyces carlsbergensis* yeast strain having, under beer fermentation conditions, relative to its parent strain, an altered production of at least one of hydrogen sulphide, a thiol or a thioester, and a method for producing a lager beer using such strain.

In still another aspect, the invention pertains to a genetically modified *Saccharomyces carlsbergensis* yeast strain which, relative to its parent strain, has a reduced or lacking production under beer fermentation conditions of a fusel alcohol and/or an ester thereof, and to a method of producing a lager beer, comprising fermenting a brewer's wort by such a modified yeast strain.

DETAILED DISCLOSURE OF THE INVENTION

One major objective of the present invention is to provide a method of preparing a composite yeast fermented beverage by combining separate batches of fermented beverage of which at least one is produced by a yeast strain which is genetically modified by mutation and/or recombination to have, relative to its parent strain, a reduced or lacking production of at least one flavour compound or flavour stabilizing compound.

Another objective is to provide a composite beverage having a predetermined content of one or more flavour compound(s) and/or compounds that stabilizes the flavour of the beverage.

It will be appreciated that the invention also provides the means of providing novel fermented beverages which are based on the production of a single batch using a single yeast strain according to the invention which is genetically modified by mutation and/or recombination to have, relative to its parent strain, a reduced or lacking production of at least one flavour compound or flavour stabilizing compound.

In a particularly interesting embodiment of the invention, the composite yeast fermented beverage is a beer such as a lager beer. Almost all beer production world-wide is carried out with pure cultures, i.e. single cell cultures, of yeast belonging to the genus Saccharomyces. Beer can also be made with yeast which are not Saccharomyces spp. such as e.g. *Schizosaccharomyces pombe*. Among Saccharomyces spp. brewing yeast, *S. carlsbergensis* as described above is a commonly used strain for production of lager beer.

However, the invention is also useful in the manufacturing of any other type of yeast fermented beverage, of which notable examples include wine, sake and cider. It is within the scope of the invention to provide either separate batches of such beverages having a modified content of flavouring compounds which are manufactured by means of a modified yeast strain according to the invention, or a composite beverage being produced by combining two or more separate batches of the beverage, each of which is made with a different yeast strain, at least one of said batches being a fermented base beverage produced with a yeast strain which is modified by mutation or recombination to have, relative to the parent strain from which it is derived, a reduced or lacking production of at least one flavour compound or of at least one compound that is capable of stabilizing the flavour of said composite yeast fermented beverage by forming adducts with staling compounds present therein.

Whereas the composite beverage may be prepared by combining two or more separate batches of fermented beverage as they are after completion of the fermentation step, it may be convenient to make a composite beverage of which at least one of the components is a batch which is at least partially dehydrated. In accordance with the invention, it is also possible to isolate from one or more of the separate batches, a flavour compound or a flavour stabilizing compound with the objective of obtaining the composite beverage by combining the one or more batches of beverage with the thus isolated compound(s).

It will be understood that in one convenient embodiment, the invention provides a fermented base beverage produced with a yeast strain which is modified by mutation or recombination to have, relative to the parent strain from which it is derived, a reduced or lacking production of at least one flavour compound or of at least one compound that is capable of stabilizing the flavour of said composite yeast. As used herein the expression "fermented base beverage" indicates a separately produced beverage which, with respect to one or more flavouring and/or flavour stabilizing compound as defined above, has a reduced content relative to the content in the same beverage produced with a yeast strain which, with respect to the particular compounds, have not been genetically modified.

Thus, such a base beverage may be one that has a reduced content of at least one compound that is normally present in that particular type of beverage. In a beer, and also in other yeast fermented beverages, such compounds include those mentioned by Meilgaard (1975) to which there is referred. Thus, as an example, a base beer beverage may have a reduced content of one or more of the following compounds: sulphite, hydrogen sulphide, dimethyl sulphoxide, methanethiol, ethanethiol, methylthioacetate, ethylthioacetate, amyl alcohol and isoamyl acetate.

In accordance with the invention, the desired composite beverage is made by combining a base beverage as defined above with one or more batch components or flavouring and/or stabilizing compound(s) isolated from such a batch. It will be understood that these components which are combined with the base beverage will include (i) batches of beverages produced with a yeast strain that has not been genetically modified, (ii) batches of beverage produced with a strain that is genetically modified by mutation or recombination to have a reduced or enhanced content of one or more particular flavouring or stabilizing compound(s), (iii) batches of (i) or (ii) that has been partially dehydrated and (iv) one or more flavouring and/or stabilizing compounds isolated from (i), (ii) or (iii).

Another objective of the invention is to make it possible to provide a composite beverage by manufacturing, either centrally or locally, a base beverage by using a genetically modified yeast strain as provided herein and based upon that base beverage make composite beverages by combining the base beverage with one or more of the above components. It may be particularly convenient to use, as the non-base beverage components, rehydrated, i.e. concentrated, beverages or isolated compounds, as this makes it economically feasible to ship such components from a central production facility to manufacturers of a base beverage who can then combine their own base beverage with one or more of the provided components to make the final product having the desired flavour.

It will also be appreciated that it is possible for such a manufacturer to make different composite beverages based on the base beverage each having a specified and predetermined flavour profile.

Whereas the invention can be applied as described above to facilitate local production of composite beverages having a given desired flavour profile, it also makes it possible to provide a central production facility with the means of providing in an economically advantageous manner the possibility to manufacture, based on a bulk production of a base beverage as defined herein, a range of products within a given beverage product which are all different with respect to content of flavour compounds, i.e. having different flavour profiles.

Sulphite is, as it is described above, an important compound in yeast fermented beverages including beer where sulphite acts both as an antioxidant and as an agent that masks certain off-flavours and thereby stabilizes beer flavour. In particular, it has been shown that several aldehydes such as trans-2-nonenal (t2n) are responsible for so-called "stale flavour". It is recognized that sulphite may mask the staling effect of such compounds. Thus, a certain level of sulphite in beer and other yeast fermented beverages is essential.

However, whereas it is generally desirable that a fermented beverage has a high content of sulphite in order to obtain a high stability of the beverage, there are in many countries regulatory limits for how much sulphite a beverage is permitted to contain. It is well-known that even if the same yeast strain is used in the fermentation of the beverage, the amount of sulphite in separate production batches may vary considerably and hence, the amount of sulphite is either too low to secure stability or it exceeds the permitted level. In the former case, sulphite can be added up to the desired level.

The present invention has made it possible to provide a beverage product having an optimized, predetermined level of sulphite by combining a batch of the beverage having a high content of sulphite with at least one other batch made with a genetically modified yeast strain which does not produce sulphite or which, relative to its parent strain, has a significantly reduced production hereof. Accordingly, in one useful embodiment the method makes use of a yeast strain which is modified by mutation or recombination to have a reduced or lacking production of sulphite, e.g. a strain that produces at the most 5 ppm of sulphite, such as at the most 4 ppm including at the most 3 ppm or even at the most 2 ppm, e.g. at the most 1 ppm. In preferred embodiments, the strain is substantially incapable of producing sulphite. Such a modified yeast strain is preferably a Saccharomyces species including *Saccharomyces carlsbergensis*.

In accordance with the invention, the method of preparing a composite beverage may imply that at least one batch of fermented beverage is used that is produced by using a yeast strain which is modified genetically to have, relative to the parent strain from which it is derived, an enhanced production of a flavour compound or of a flavour stabilizing compound. Accordingly, the invention encompasses that such a batch is produced with a yeast strain which is modified by mutation or recombination to have an enhanced production of sulphite, such as a sulphite production in excess of 30 ppm, including in excess of 40 ppm such as in excess of 50 ppm of sulphite, e.g. in excess of 100 ppm. Such a strain can e.g. be provided as described in Hansen et al., 1996b.

Hydrogen sulphide is, as it is mentioned above, a generally undesired sulphur compound in yeast fermented beverages including beer, as it confers a strong "putrefied egg" off-flavour to the beverage. The threshold level of that compound has been reported as being 10 $\mu$g/L in lager beer and 30 $\mu$g/L in ales. It is therefore one objective of the present invention to provide batches of fermented beverage having a low content of that compound. Additionally, it has been shown that there is a direct metabolic linkage between formation of hydrogen sulphide and certain thiols such as e.g. ethanethiol and thioesters including methylthioester and ethylthioester. This linkage implies that fermenting the beverage batch with a yeast strain having a reduced or lacking ability to produce hydrogen sulphide will result in a beverage also having a reduced content of thiols and esters of such thiols.

Accordingly, in a useful embodiment of the invention, there is used a method of producing a composite beverage wherein the yeast strain which is modified by mutation or recombination has a reduced or lacking production of a compound selected from the group consisting of hydrogen sulphide, a thiol and a thioester. However, it is also possible to provide such a modified strain which has an enhanced production of at least one of hydrogen sulphide, a thiol and a thioester.

In further embodiments, the method according to the invention provides the means of making a beverage batch which is made by fermenting with a yeast strain which is genetically modified to have a reduced or lacking production of dimethyl sulphide and of making a beverage batch to be used as a component in the composite beverage which has a reduced or no production of a fusel alcohol such as amyl alcohol or isoamyl alcohol and/or an ester of such a fusel alcohol. In one specific embodiment of the latter method, the modified yeast strain having a reduced or lacking production of fusel alcohol is one that is modified in a gene involved in metabolism of branched amino acids, which in the parent strain leads to formation of isoamyl acetate. As it is described above, the pathway leading to the formation of isoamyl alcohol and isoamyl acetate in yeast belonging to the Saccharomyces genus involves several enzymes encoded by specific genes. It has been found that modified strains of brewer's yeast can be provided which has a reduced or lacking production of isoamyl alcohol and/or the corresponding acetate ester by disrupting or mutating at least one of the genes involved in this pathway such as a gene selected from the group consisting of LEU1, LEU2, LEU3, LEU4, YOR108W, ATF1, AFT1-CE, ATF1-CA and ORF YDL080CR (THI3). Examples of how such genetically modified strains can be provided will be described in details in the following examples.

A further objective of the present invention is to provide a method of making a composite beverage which includes that the separate batches of beverage which are used for making the final composite beverage can be produced in conventional industrial scale and using conventional production methods including, when the beverage is a beer, that a conventional brewer's wort can be used. This implies that the modified strains which are used for fermentation have a fermentation performance under such industrial production conditions which is essentially equivalent to that of a normal, non-modified production strain of yeast. This requirement implies i.a. that the fermentation time under conventional conditions is not extended to any significant degree and that the amount of yeast biomass that is produced during the fermentation is substantially at the same level as with a normal yeast production strain.

In the present context, the expression "industrial scale" indicates that the volume of a batch of yeast fermented beverage is at least 1,000 L such as at least 10,000 litres, including at least 50,000 litres.

In one specific embodiment, an example of which is described in the following examples, the composite yeast fermented beverage is made by combining at least 2 separate batches of beverage each having a different content of sulphite so as to obtain a composite beverage having a predetermined content of sulphite. The predetermined amount of sulphite will depend on the type of fermented beverage and may also be determined by local regulatory rules. Typically, a predetermined level of sulphite may be in the range of 5 to 20 including 10 to 20 ppm such as in the range of 12 to 18 ppm including in the range of 14 to 16 ppm, e.g. about 15 ppm.

Whereas the invention as described herein is particularly useful in the production of a fermented beverage product such as beer including lagers, stouts and ales, it will be appreciated that genetically modified yeast strain as provided herein can be used in the production of any fermented beverage where there is a need to control the content of one or more flavour compounds. This applies in particular to beverage products like wine, cider and sake, but it is contemplated that such modified yeast strains are useful in the production of spirits and beverage products which is made by distillation of yeast fermented cereals, fruits and vegetables. It is also envisaged that the methods for providing genetically modified yeast strains as provided herein can be applied directly to yeast strains which are particularly adapted to be effective leavening agents in bread doughs such as baker's yeast.

Accordingly, the genetically modified yeast strains as provided herein include brewer's yeast, wine yeast, distiller's yeast, baker's yeast and a fusion or a hybrid thereof.

In the production of conventional yeast fermented beverages, the yeast strain is generally present in the fermentation medium as free, non-immobilized cells, optionally in a flocculated or partially separated state. However, it may be convenient in a fermentation process to have the yeast cells in an immobilized state. Accordingly, the present invention encompasses a method as defined herein wherein the yeast strain used for at least one of the batches is immobilized during fermentation. The immobilization may e.g. be on polymer particles or on any other solid support material or the cells may alternatively be contained or entrapped in or by a porous material having pores of a size which retains the yeast cells but permits the liquid phase of the fermentation medium and solutes therein to come into contact with the thus immobilized yeast cells.

The method of the invention may, as it is mentioned above, comprise a step of at least partially dehydrating at least one of the separate batches of fermented beverage. Such a dehydration step can be carried out using any conventional method of removing water from an aqueous medium including as examples evaporation and filtration by reverse osmosis. The rehydration step may lead to a concentrate of the fermented beverage having a dry matter (DM) content of at least 10 wt % including a DM content of at least 20 wt % such as at least 30 wt %, e.g. at least 40 wt % DM such as at least 50 wt % DM.

In a final step of the method according to the invention, the base fermented beverage is combined with one or more separate batches of fermented beverage and/or isolated compounds to obtain the final composite beverage product. The number of batch components that is combined may vary e.g. according to particular customer preferences. Thus, the number of components which are combined is typically in the range of 2 to 10, such as in the range of 2 to 8 including a number in the range of 2 to 5 batches. In a specific embodiment, the proportion of the fermented base beverage in the composite beverage is at least 25% by volume, such as at least 50% including at least 75%.

It will be appreciated it is possible to add further components to at least one of the separate batches or to the composite fermented beverage with the objective of providing additional desirable characteristics to the beverage product. Thus, as examples such further additive components are selected from a flavour component, a stabilizing agent and a colouring agent. Such a flavour component may e.g. be a separate yeast fermented beverage batch having a high content of one or more particularly desired flavour compounds.

In a further aspect, the invention relates to a composite beverage obtainable by the method as described herein. As it has been mentioned above, such a beverage can be a beer including ale, lager and stout, a wine, a spirit product, an ethanol-containing beverage product made by distillation of a fermented cereal, fruit or vegetable material. In preferred embodiments, the beverage is a beer, which can be provided as bulk in large shipment containers such as tanks or barrels or as retail products in conventional containers for that purpose including bottles made of glass or a polymeric material such as e.g. PET or PEN, and metal containers e.g. of tin foil or aluminium.

Whereas one major use of the batches of yeast fermented beverage as defined herein is as a component of a composite beverage product, it will be appreciated that such batches having a relatively high content of a flavour compound which is desirable in another context such as in the manufacturing of a food product other than a beverage, such batches can, optionally after having been at least partially dehydrated, be used directly as a flavour compound in food products e.g. in a bakery product, or the flavour compounds may be isolated from such batches and used in such isolated form, optionally after purification, as a flavour compound.

In a further aspect, the invention relates to a genetically modified yeast strain which, relative to its parent strain, has a reduced or lacking production of sulphite during production of a fermented beverage.

As it is described above, sulphite is produced by yeast via the sulphur assimilation pathway, the final steps of which include that the MET14 encoded APS kinase catalyses the formation of phosphoadenylylsulphate (PAPS) which in turn is reduced by PAPS reductase (encoded by MET16) to sulphite. A sulphite deficient yeast strain according to the invention can be provided by genetically modifying a strain having a wild-type sulphur assimilation pathway in one or more of the genes involved in that pathway.

Such modifications are e.g. provided by disruption of one or more genes, e.g. by replacing a wild-type gene with a deletion allele whereby the gene becomes inactivated. Other possible means of making a strain deficient with respect to a certain phenotype is to mutate the strain in the appropriate target gene including mutation by means of conventional chemical mutagens or UV and site-directed mutagenesis according to methods which are well-known in the art. Alternatively, sulphite deficient yeast strains can be provided by selecting strains which are spontaneously mutated in one or more genes involved in the sulphur pathway. Illustrative examples of using such techniques for providing sulphite deficient yeast strains including *S. carlsbergensis* are described in details in the following examples. In the present context, useful yeast strains include strains wherein all copies of the MET14 gene coding for APS kinase is inactivated.

It has been found that it is possible to provide such a genetically modified yeast strain which during production of a fermented beverage produces less than 5 ppm sulphite in the beverage. In preferred embodiments, the modified strain produces less than 4 ppm sulphite including less than 3 ppm sulphite such as less than 2 ppm sulphite, e.g. less than 1 ppm sulphite. In particularly preferred embodiments, the modified yeast strain is substantially incapable of producing sulphite.

In accordance with the invention, strains of any species of yeast which are used in the production of fermented beverages including *Saccharomyces carlsbergensis* and *Saccharomyces cerevisiae* can be provided which are genetically modified to have a reduced or lacking production of sulphite. One typical example of such strains is the *Saccharomyces carlsbergensis* strain PFJ501 that has been deposited in accordance with the Budapest Treaty on Jul. 8, 1998 with the American Type Culture Collection (ATCC) under the accession number ATCC 74454.

It will be appreciated that a sulphite deficient yeast strain can be further modified so as to have, in addition to the reduced or lacking capability to produce sulphite, a reduced or lacking production of one or more of other of the above flavour compounds or flavour stabilizing compounds. Thus, in a further embodiment the sulphite deficient yeast strain according to the invention is further genetically modified to have under fermentation conditions, relative to its parent strain, a modified production of at least one further of the above compounds including a reduced or lacking production of a fusel alcohol and an ester thereof and/or an altered production of at least one of hydrogen sulphide, a thiol or a thioester and/or a reduced or lacking capability to produce dimethyl sulphide from dimethyl sulphoxide.

It is a significant objective of the present invention to provide genetically modified yeast strains as described above which irrespective of the modification have retained the capacity to ferment a medium to a beverage at an industrially acceptable efficiency. Thus, the sulphite deficient strains are strains which are industrially feasible in the production of a fermented beverage including a lager beer, the method comprising fermenting an aqueous substrate medium with the modified yeast strain as described above.

Dimethylsulphide, DMS is another sulphur compound, the level of which in a fermented beverage determines the organoleptic characteristics hereof. In accordance with the invention, it is therefore desirable to produce batches of yeast fermented beverages having a reduced level of this flavour compound. Accordingly, the invention provides in another aspect a genetically modified yeast strain which, relative to its parent strain, has a reduced or lacking capability of converting dimethyl sulphoxide (DMSO) into dimethyl sulphide.

The present inventors have confirmed that the *S. cerevisiae* open reading frame (ORF), YER042w, encodes a MetSO reductase and they suggest the designation MXR1 for the gene. It was discovered that this MetSO reductase is capable of reducing DMSO to DMS. It was also discovered that the allotetraploid lager yeast *S. carlsbergensis* contains a gene which is homologous to the above *S. cerevisiae* ORF. As referred to herein, this homologous gene is designated MXR1-CE. It was further discovered that *S. carlsbergensis* contains at least one further gene coding for MetSO reductase also showing homology to the YER042w ORF and the MXR1-CE. This homologous further gene is designated herein as the MXR1-CA gene.

Based on these discoveries it has become possible to provide yeast strains including strains of *Saccharomyces carlsbergensis* and *Saccharomyces cerevisiae* having a reduced or lacking capability of converting DMSO into DMS. Such strains can be made by genetically modifying a yeast strain having functional genes coding for the MeSO reductase including the above genes. Thus, in one useful embodiment, the yeast strain according to the invention is a yeast strain such as a Saccharomyces strain in which the ORF YER042w (MXR1) or a homologue hereof which codes for a gene product capable of converting dimethyl sulphoxide into dimethyl sulphide, is inactivated.

An inactivation of one or more of said genes can be made by use of conventional techniques including those mentioned above in connection with the description of a sulphite deficient strain.

It will be understood that a yeast strain as described above, which is modified to have a reduced production of DMS can be further genetically modified to have under fermentation conditions, relative to its parent strain, a reduced or lacking production of a fusel alcohol and an ester thereof and/or an altered production of at least one of hydrogen sulphide, a thiol or a thioester and/or a reduced or lacking capability to produce sulphite.

To be useful as a beverage fermenting strain according to the invention, a DMS deficient yeast strain has preferably retained its capability to be an effective fermenting strain in industrial beverage production such as in the production of a lager beer. Accordingly, an objective of the invention is to provide a method of producing a yeast fermented beverage, comprising fermenting an aqueous substrate medium with a DMS deficient yeast strain according to the invention.

As mentioned above, there have been disclosed attempts to control the formation of hydrogen sulphide in beer production by means of DNA recombinant technology. It has now been found that it is possible to provide non-recombinantly modified *Saccharomyces carlsbergensis* yeast strains having under beer fermentation conditions, relative to its parent strain, an altered production of hydrogen sulphide or of a thiol or a thioester. Such non-recombinational methods include conventional mutagenization procedures and selection of spontaneously occurring mutants combined, when appropriate, with crossing of yeasts of opposite mating types. In the following, illustrative examples of such procedures and methods are described. These examples, however, are not limiting and any non-recombinational method which lead to modified brewing yeast strains having, relative to their respective parent strain, a reduced or enhanced production of hydrogen sulphide or sulphur compound, the production of which is linked to the hydrogen sulphide production, is encompassed by the invention.

Thus, in accordance with the invention there is provided a mutant *S. carlsbergensis* yeast strain which, relative to a parent strain from which it is derived, has a reduced hydrogen sulphide production including the strains designated herein as JH441, JH442, JH443 and JH444 as described in the following, of which JH441 has been deposited in accordance with the Budapest Treaty on July 8, 1998 with the American Type Culture Collection (ATCC) under the Accession No. ATCC 74451.

There is also provided *S. carlsbergensis* strains having, relative to a parent strain, an enhanced hydrogen sulphide production, including the strains disclosed herein which are designated JH506, JH515, JH516 and JH517, of which JH506 has been deposited in accordance with the Budapest Treaty on Jul. 8, 1998 with the American Type Culture Collection (ATCC) under the Accession No. ATCC 74453.

It will be understood that a yeast strain as described above, which is modified to have a reduced or enhanced production of hydrogen sulphide can be further genetically modified to have under fermentation conditions, relative to its p arent strain, a reduced or lacking production of a fusel alcohol and an ester thereof and/or a reduced or lacking capability of converting dimethyl sulphoxide into dimethyl sulphide and/or a reduced or lacking capability to produce sulphite.

It is another objective of the present invention to provide a genetically modified yeast strain as described above which irrespective of the modification has retained the capacity to ferment a medium to a beverage at an industrially acceptable efficiency. Thus, such modified strains are preferably strains which are industrially feasible in respect of a method of producing fermented beverage including a lager beer, the method comprising fermenting an aqueous substrate medium with the modified yeast strain as described above.

In one aspect of the invention, there is provided a genetically modified *Saccharomyces carlsbergensis* yeast strain which, relative to its parent strain, has a reduced or lacking production under beer fermentation conditions of a fusel alcohol and/or an ester thereof. The genetic background for the production of these flavour compounds are outlined above. Based on the pathway leading to higher alcohols and their corresponding esters, several approaches can be used to provide *S. carlsbergensis* strains having a reduced production of these compounds.

Thus, with respect to e.g. reduced production of isoamyl alcohol and esters thereof including the acetate ester, at least the following approaches can be used in an attempt to provide such modified yeast strains:

(a) Inactivation/modification of the isopropylmalate synthases in the leucine de novo synthesis pathway (encoded by LEU4 and ORF YOR108w);

(b) Inactivation of the THI3 (YDLO80C) activity responsible for the conversion of α-ketoisocaproate to 3-methyl-1-butanol; and (c) Removal of the alcohol acetyl transferase activities encoded by ATF1-CE, ATF1-CA and ATF2 genes.

Examples of suitable methods involved in both approaches are described in the following examples. It appears from these examples that strains in which one or more of these genes are inactivated can be generated by introducing into the relevant chromosome a deletion allele of the naturally occurring gene by means of e.g. a disruption plasmid comprising the mutant gene or by means of the two-step deletion procedure as described by Scherer and Davis (1979), the so-called loop-in/loop-out method. Although these methods are presently preferred, it is contemplated that alternative conventional methods for disrupting or inactivating genes can be applied such as e.g. site-directed mutagenesis or disruption by means of transposable elements including transposons. It is also conceivable that strains having the reduced production of a higher alcohol and/or the corresponding ester can be provided by random mutagenesis or by selecting spontaneously occurring mutants.

In one useful embodiment the invention provides a *S. carlsbergensis* strain having a reduced or lacking production of isoamyl alcohol and/or isoamyl acetate including a strain in which a gene involved in the leucine de novo synthesis pathway is inactivated or modified such as a strain in which at least one of LEU4 and ORF YOR108w is inactivated or modified.

As mentioned above, a brewer's yeast strain modified in its pathways leading to the generation of esters of higher alcohols can be provided as a strain in which at least one gene coding for alcohol acetyl transferase activity including the genes ATF1-CE, ATF1-CA and ATF2 is inactivated or deleted.

A genetically modified *S. carlsbergensis* which in accordance with the invention has a reduced or lacking production of one or more higher alcohols and/or esters of such alcohols and which is effective in a method of producing a lager beer, comprising fermenting a brewer's wort, can be further genetically modified to have under fermentation conditions, relative to its parent strain, an altered production of at least one of hydrogen sulphide, a thiol or a thioester and/or a reduced or lacking capability of converting dimethyl sulphoxide into dimethyl sulphide and/or a reduced or lacking capability to produce sulphite.

The invention is further illustrated in the following examples and the drawings wherein.

Figure 3:
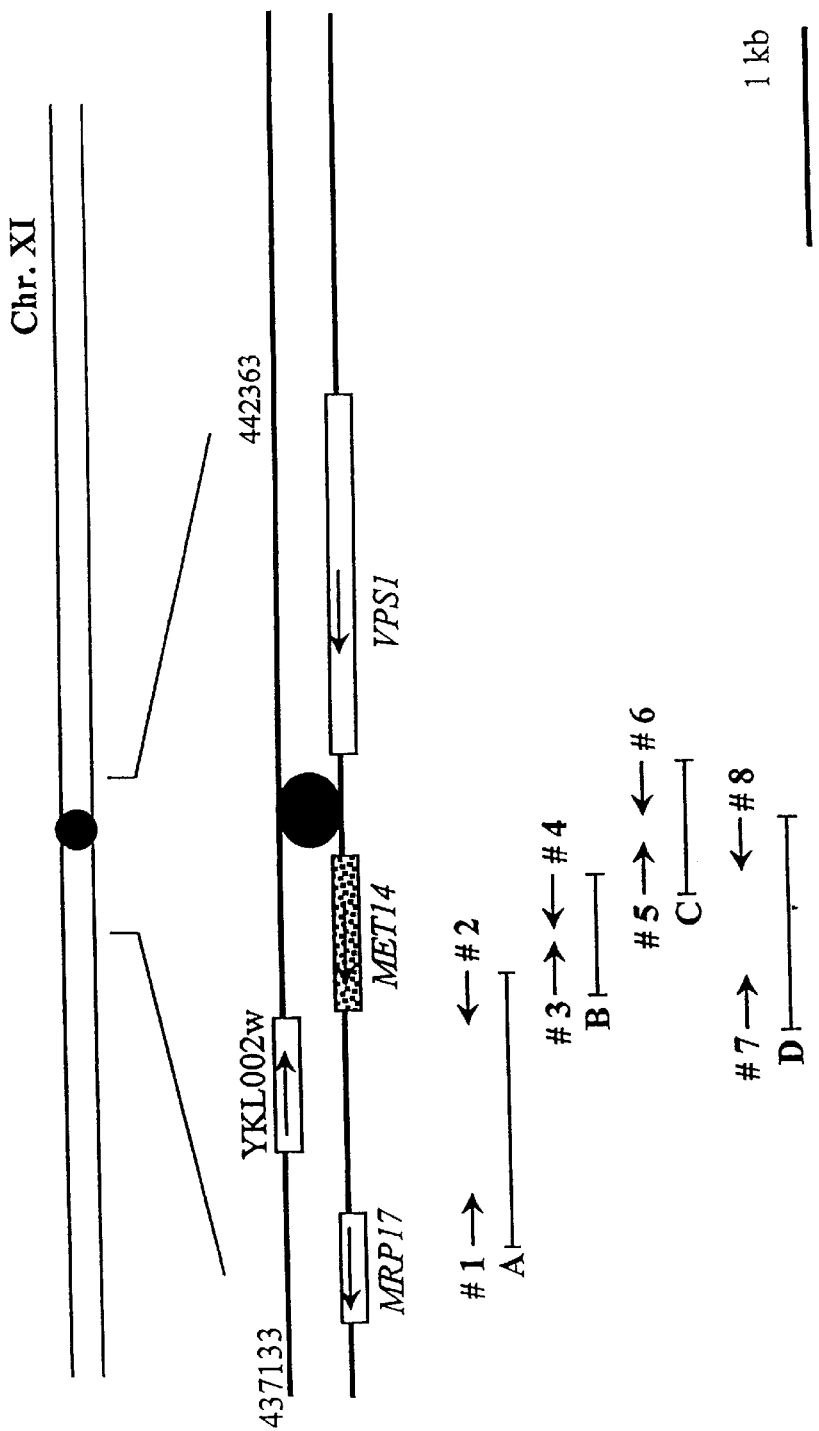

FIG. 3 illustrates the isolation of the *S. monacensis* MET14 gene that was done by using the sequence information from the *S. cerevisiae* sequence database (SGD). The MET14 gene is found on chromosome XI. A part of the chromosome, from bp 437133 to 442363, has been enlarged schematically, showing MET14 and its flanking open reading frames. oligoprimers were designed (numbered #1–#6, see Table 1.2) having either an XbaI or BamHI site in the end, enabling PCR amplification of the 3'- and 5'-ends of MET14 and also the open reading frame of the gene. The PCR fragments A and B digested with either XbaI or BamHI were cloned into pRS316 (Sikorski and Hieter, 1989) digested with the same enzymes. Both inserts were sequenced using appropriate oligoprimers. PCR fragment C was sequenced directly using oligoprimer #5. Based on the raw sequences, oligoprimer #7 and #8 were designed allowing amplification of fragment D, containing the entire MET14-CA gene including 3'- and 5'-regions. Three individually synthesized D-fragments were digested with BamHI and cloned into the BamHI site of pUC18 resulting in pPF50, pPF51 and pPF52;

FIG. 4 shows the sequence (SEQ ID NO:41) of the MET14-CA gene. The result of sequencing of the three independent clones pPF50, pPF51 and pPF52. The ATG-start codon and TAA-stop codon are underlined. The BamHI sites in the ends are cloning sites and not part of the sequence;

FIG. 5a shows the construction of a deletion allele of MET14. The insert in clone #42 is approximately 8,000 bp, the ClaI-SalI restriction digest leaves behind about 5,600 bp of the insert; A Δ denotes the position of the deletion;

FIG. 5b illustrates the construction of a deletion allele of MET14-CA by PCR. The four oligoprimers (#9–#12, Table 1.2) were all designed with restriction sites in the ends, EcoRI, BamHI, XbaI and HindIII, respectively. Only relevant restriction sites are depicted.

Figure 6:
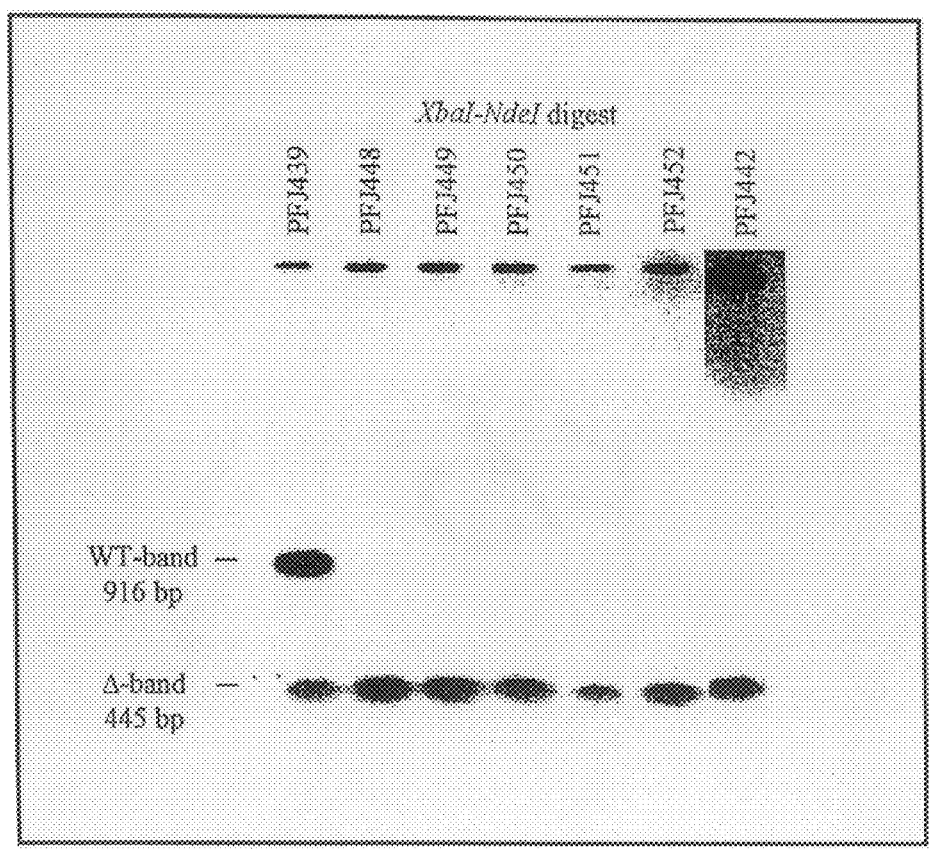
Figure 7:
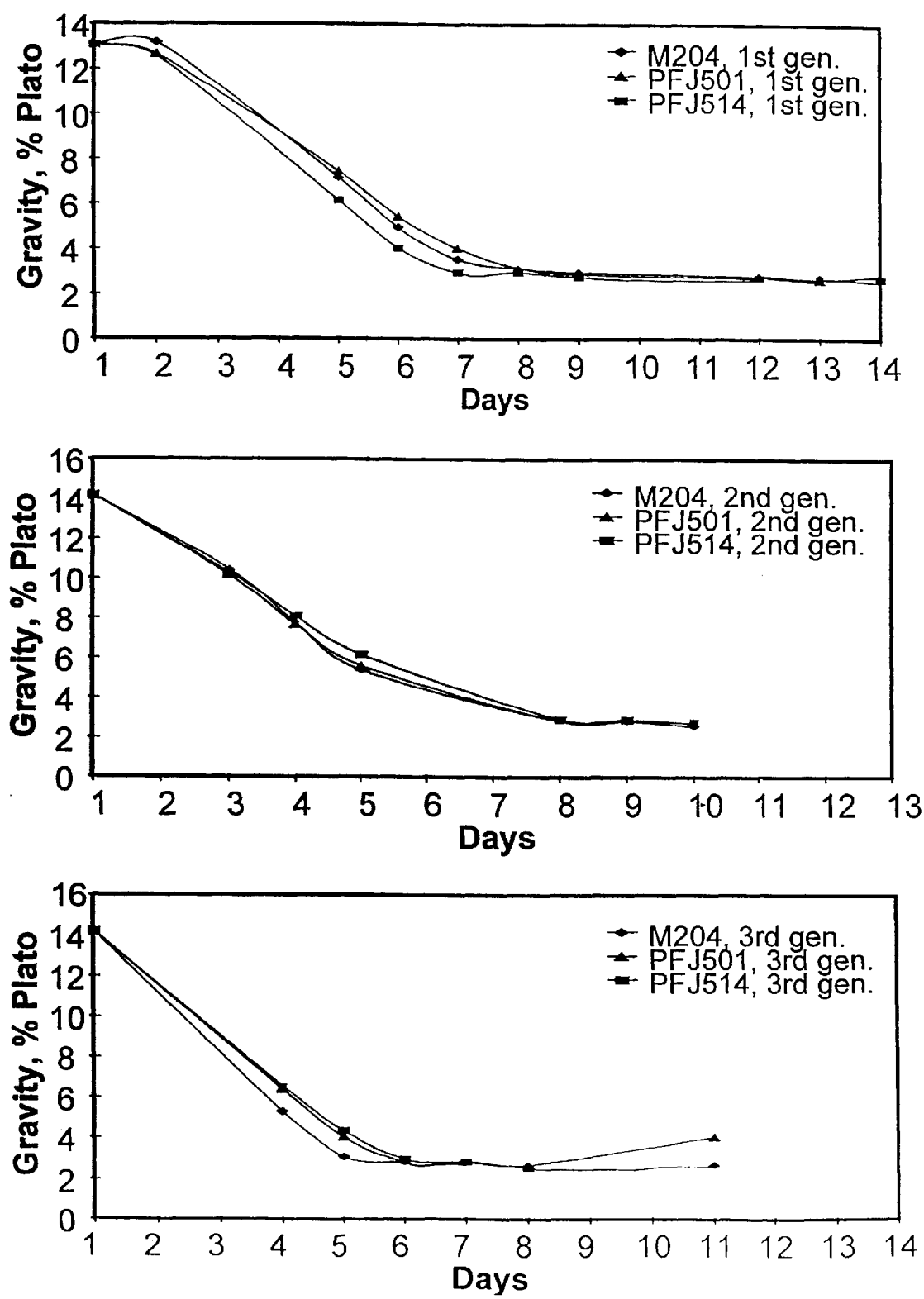
Figure 9:
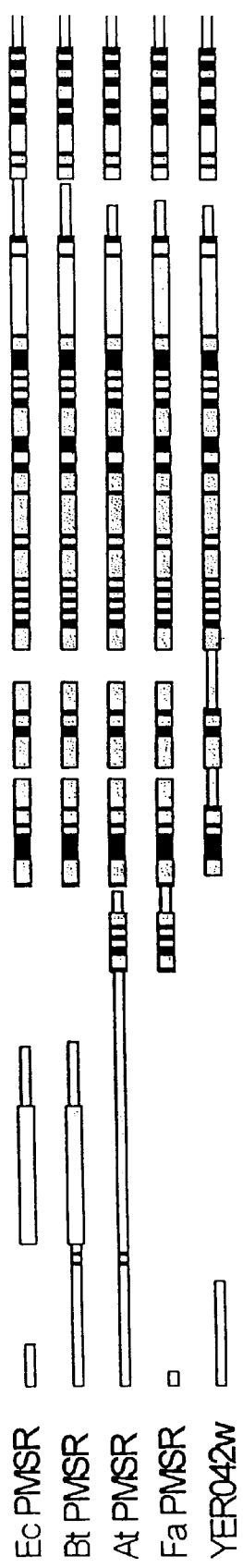
Figure 10:
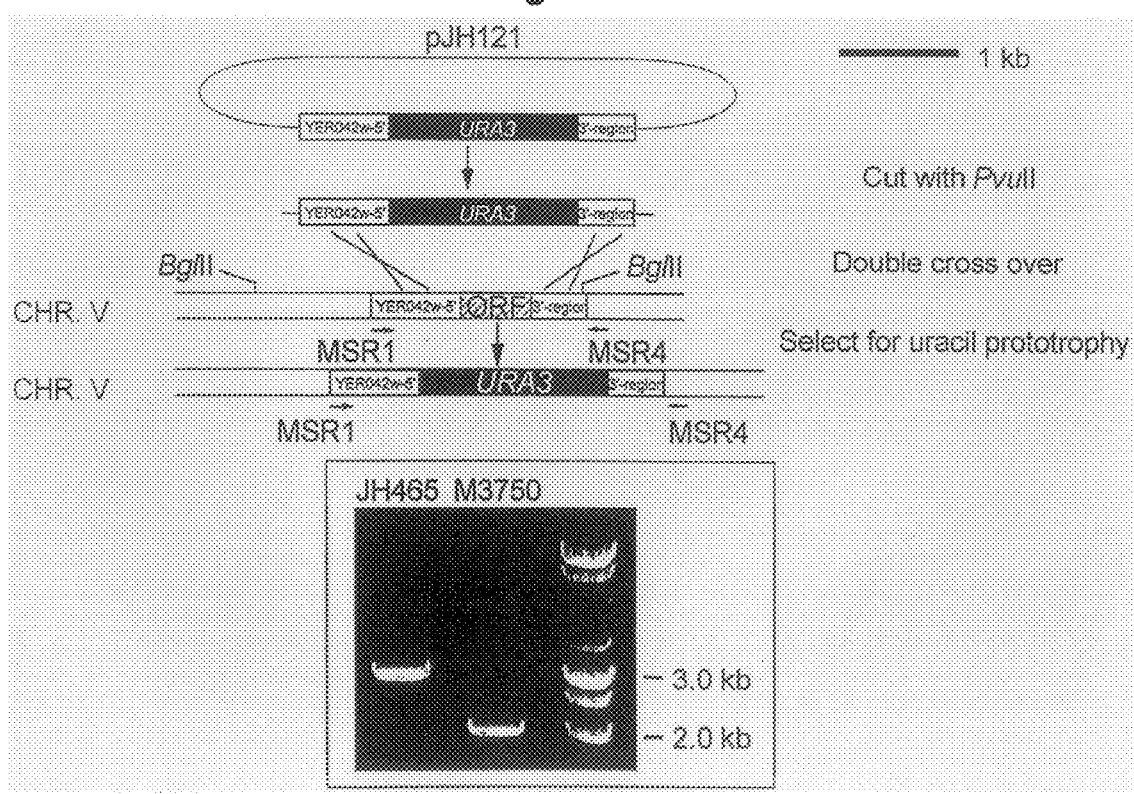
Figure 11:
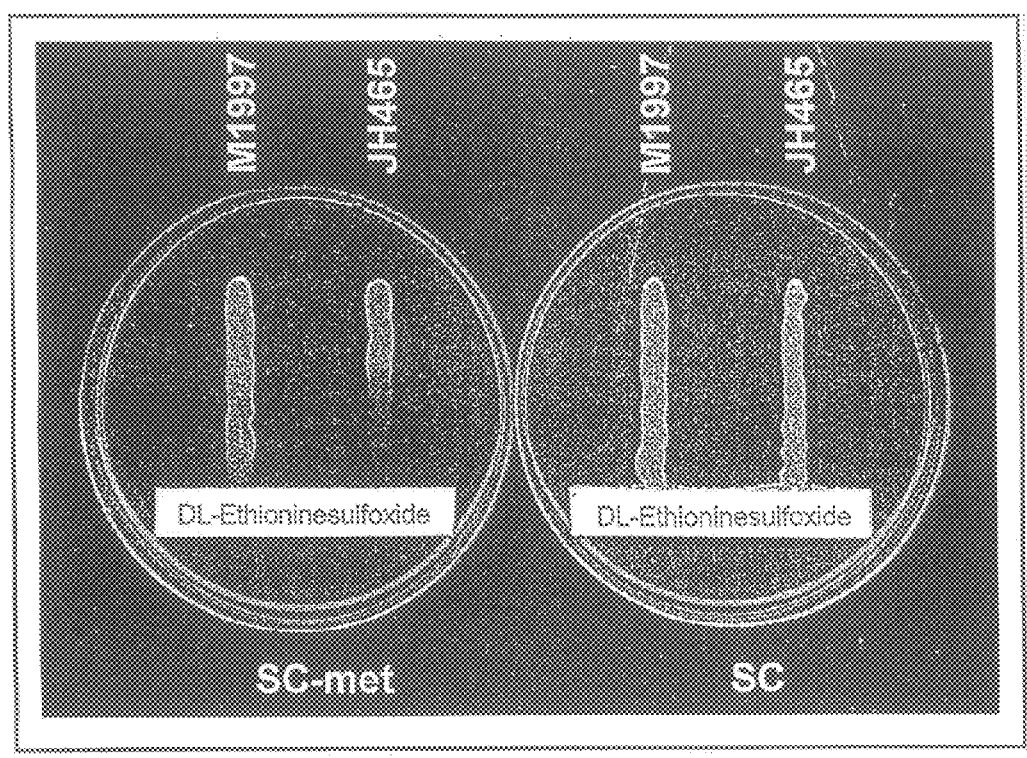
Figure 12:
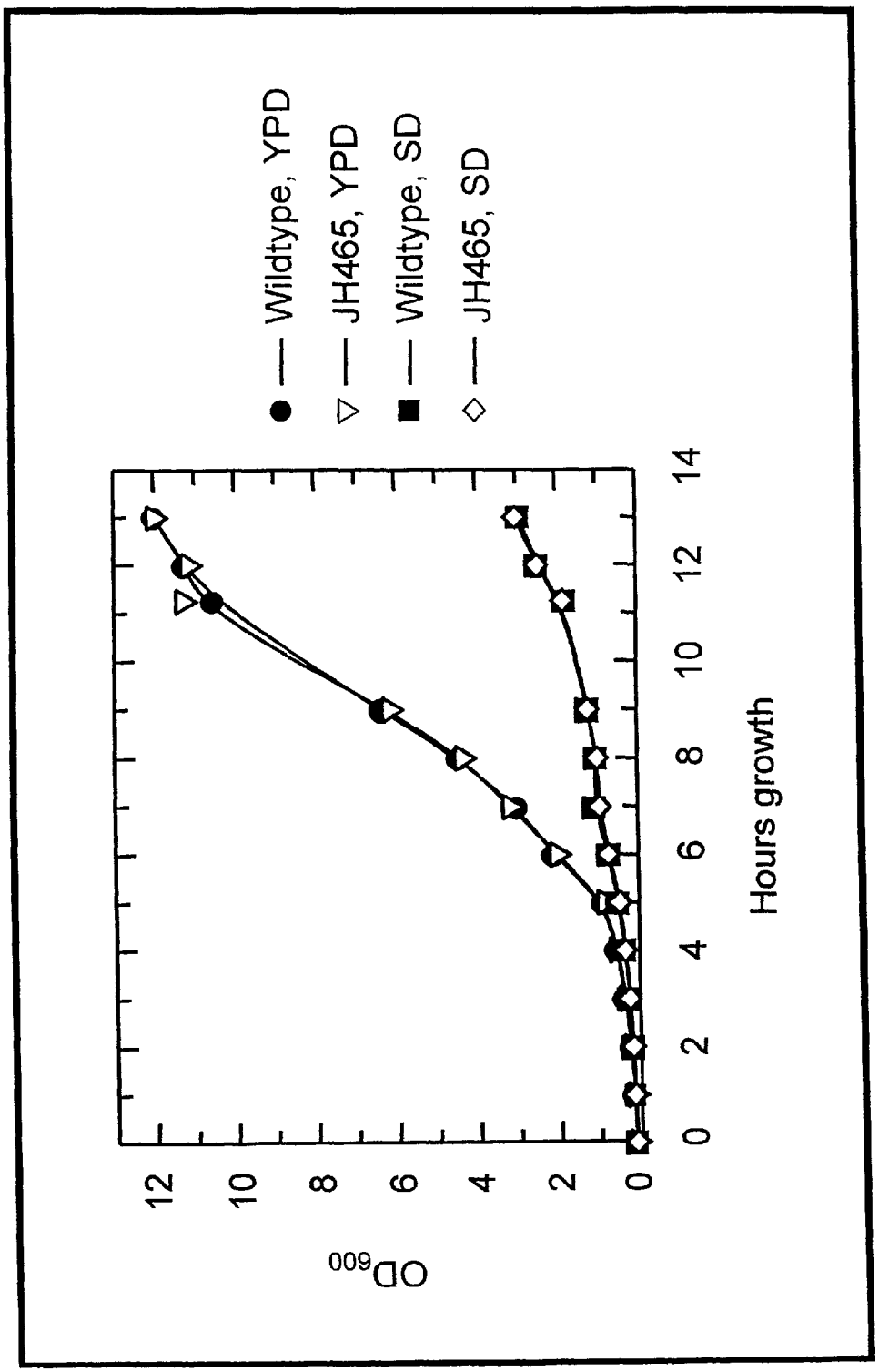
Figure 13:
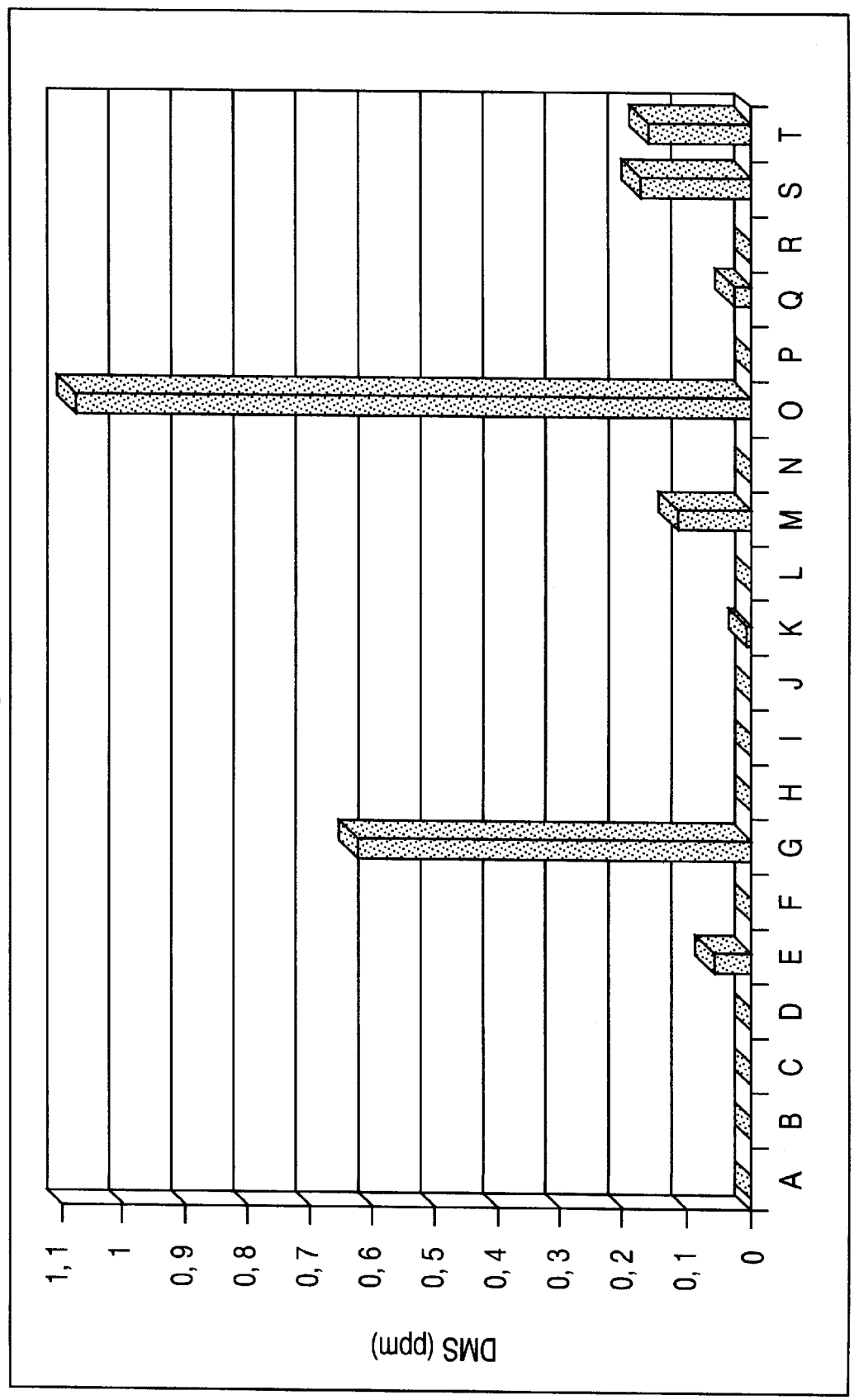
Figure 14:
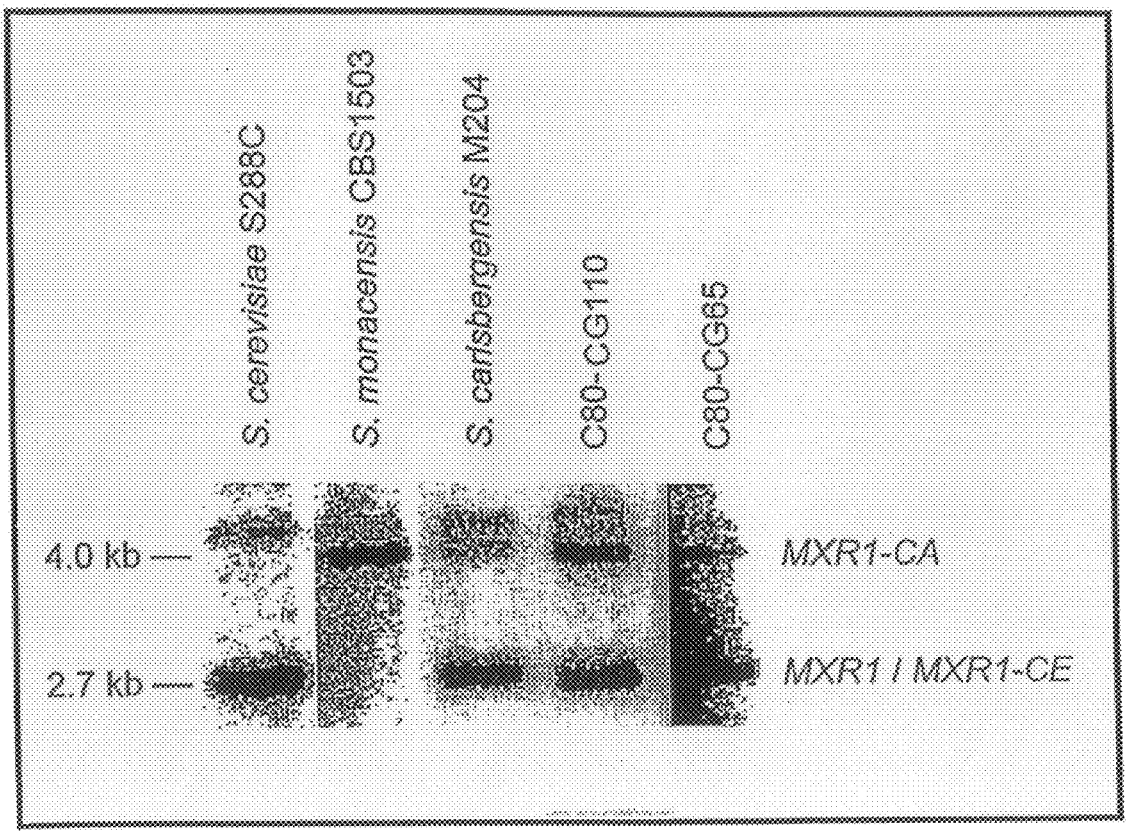
Figure 15:
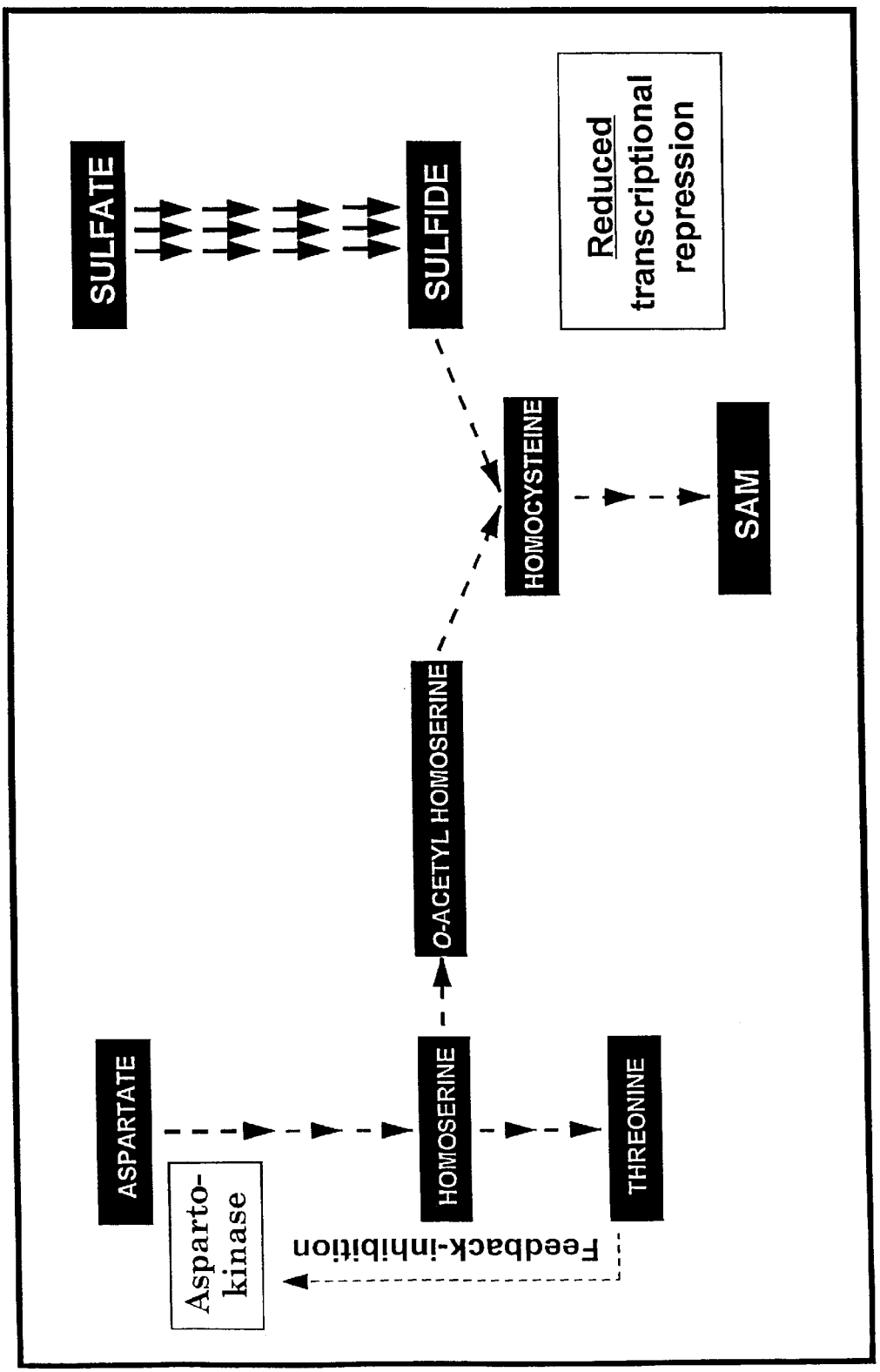
Figure 16:
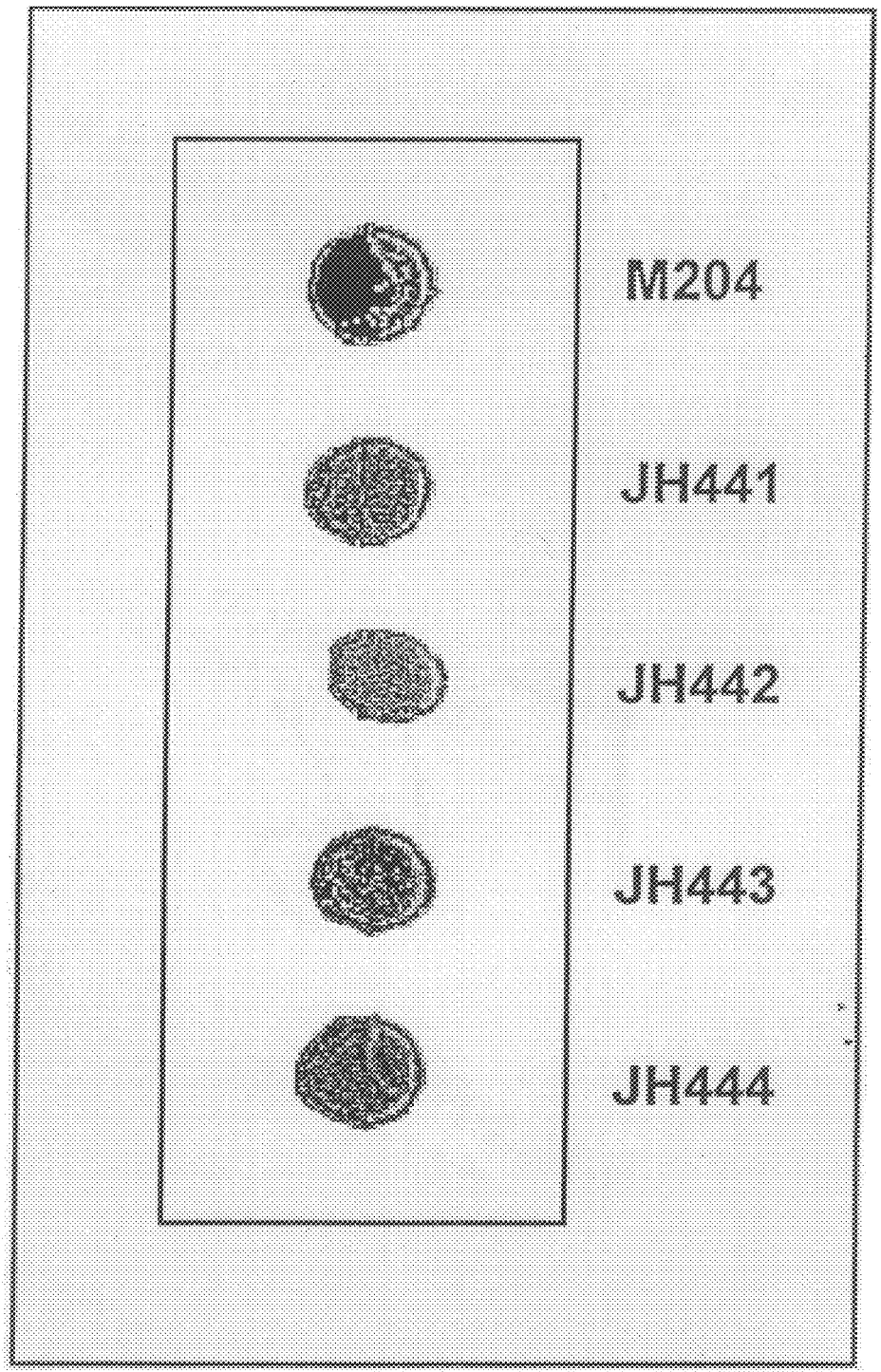
Figure 17:
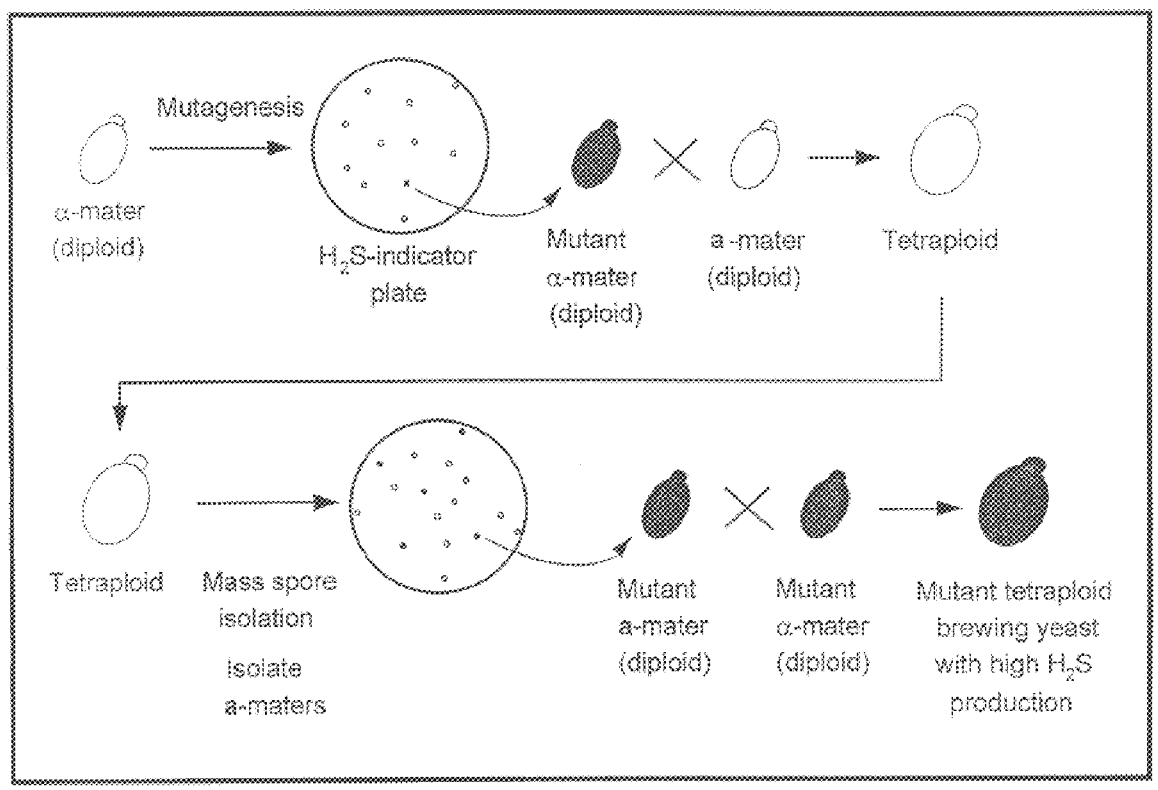
Figure 18:
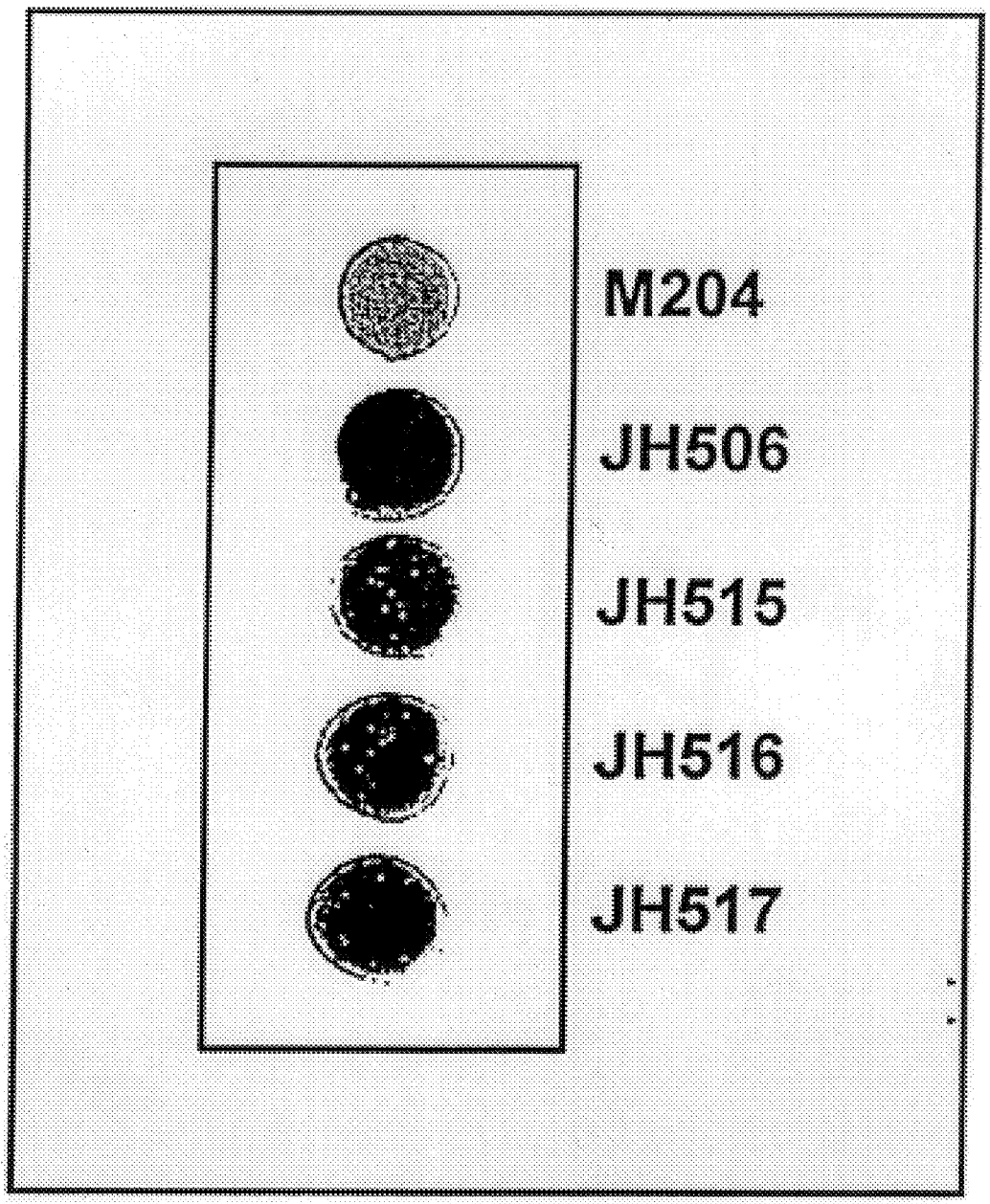
Figure 19:
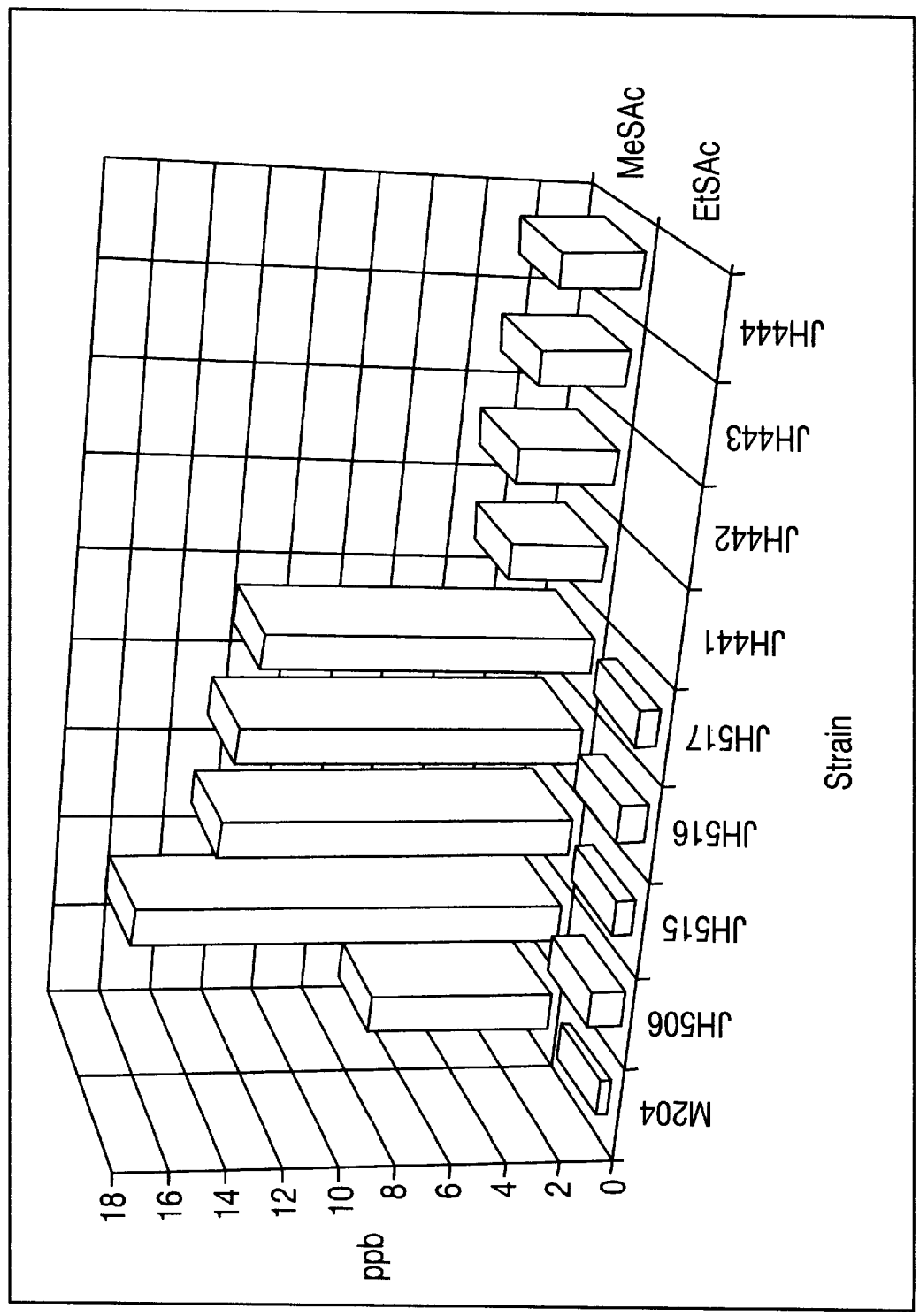
Figure 20:
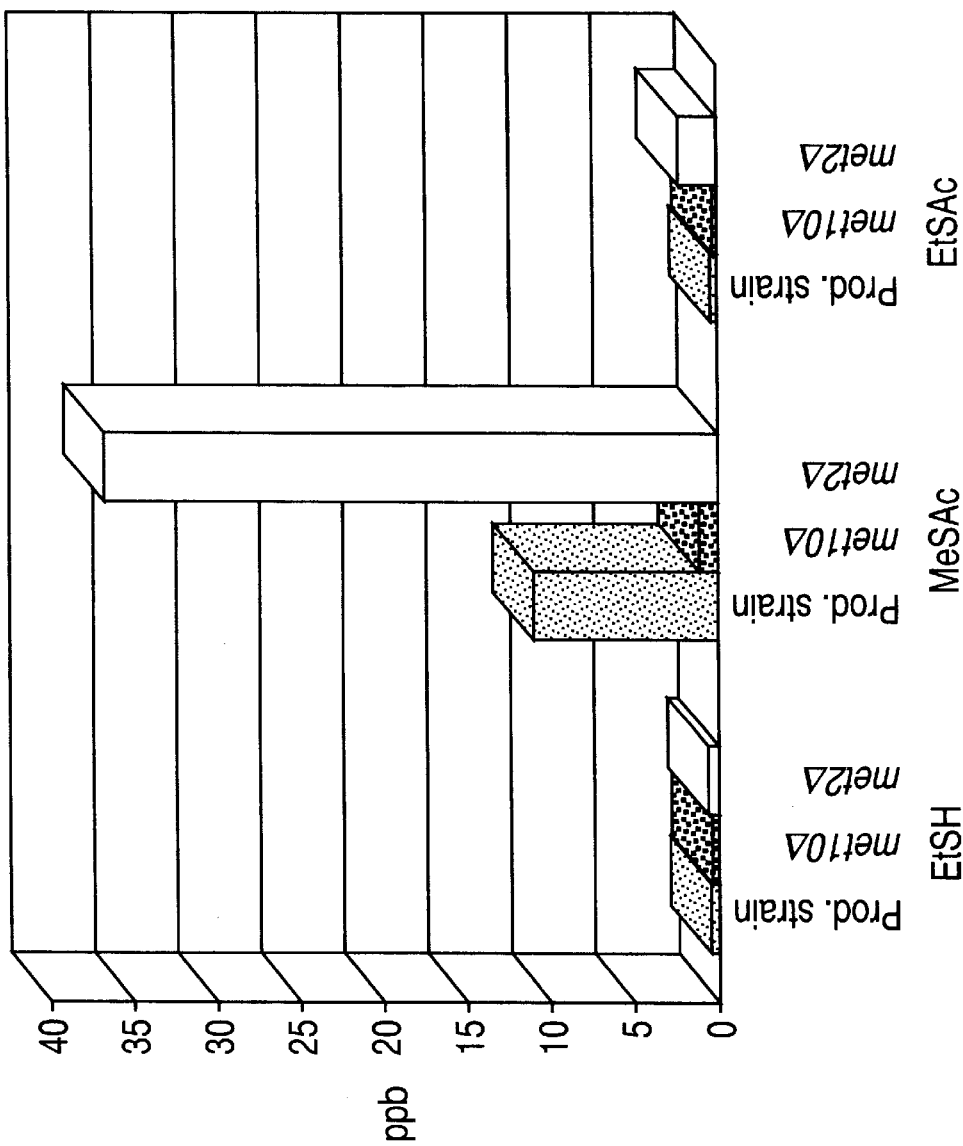
Figure 21:
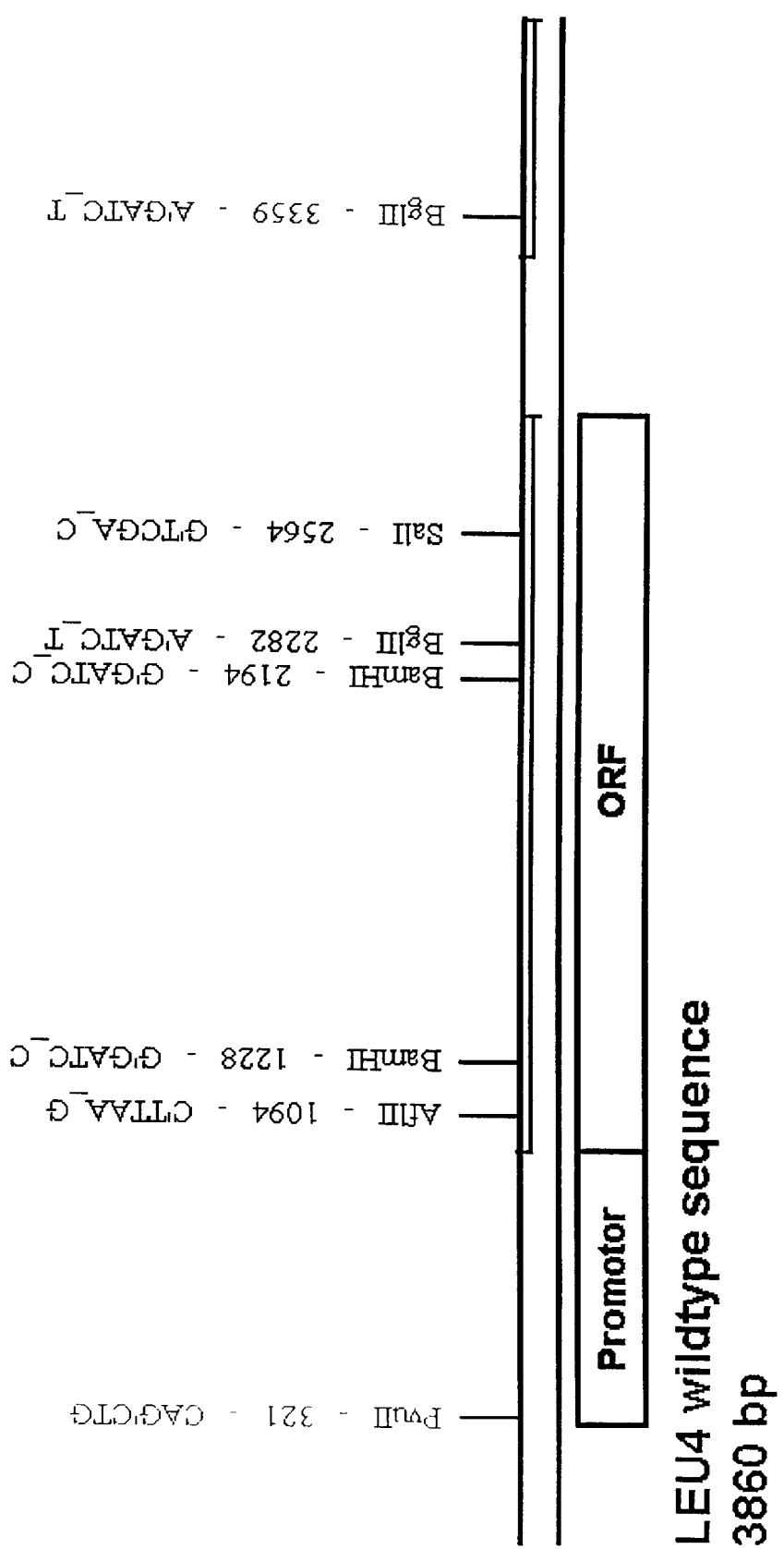
Figure 22:
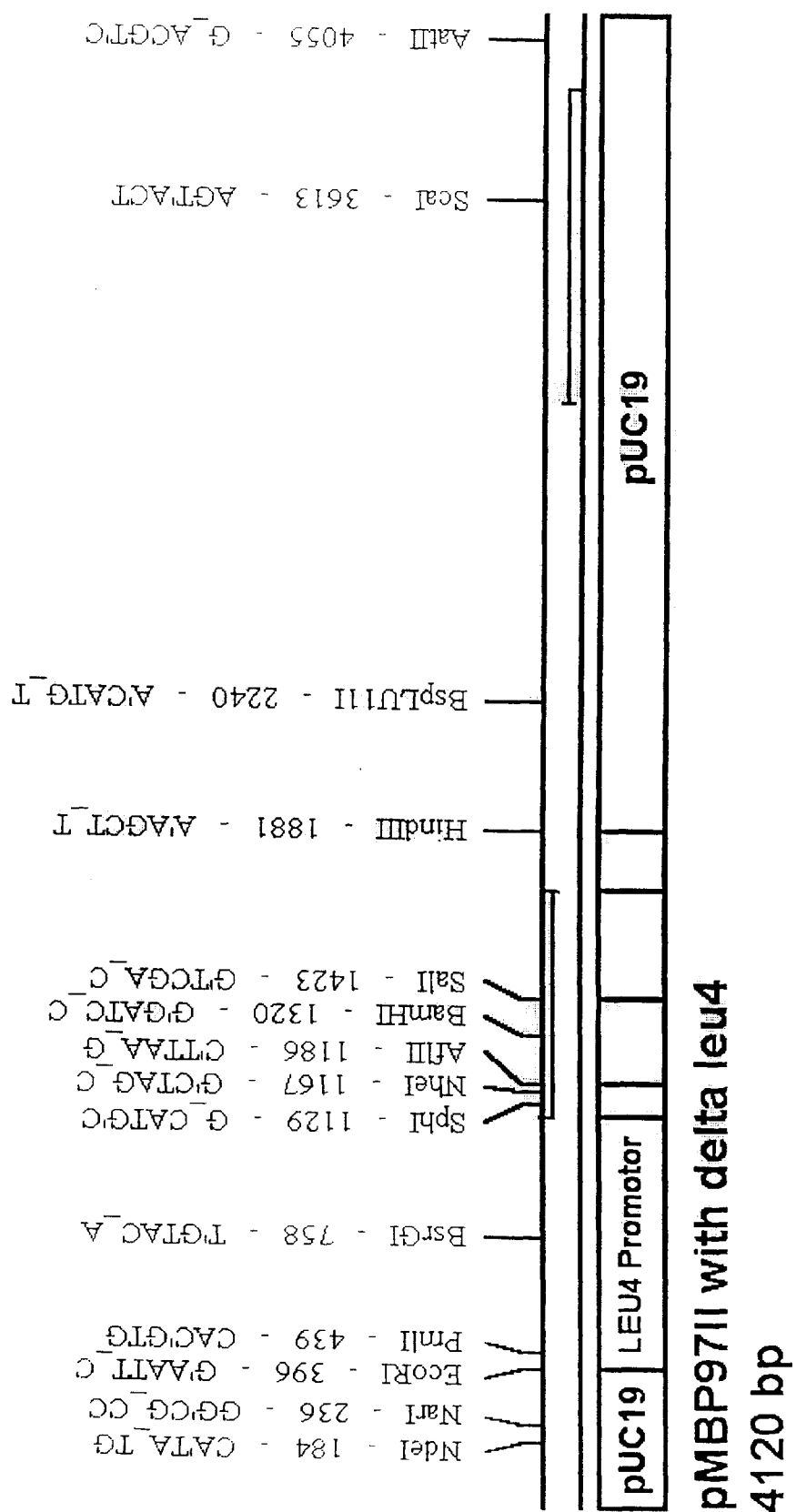
Figure 24:
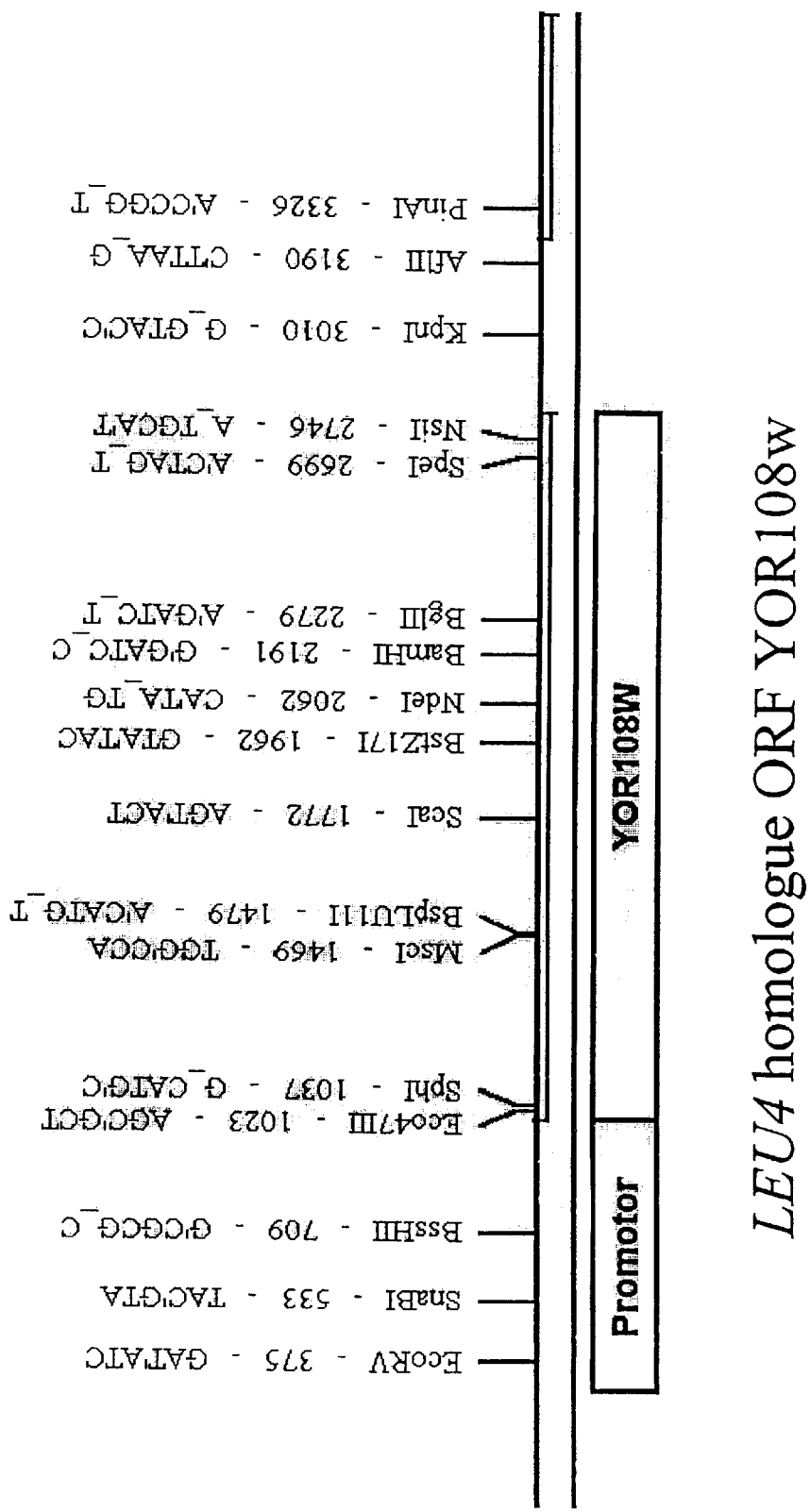
Figure 25:
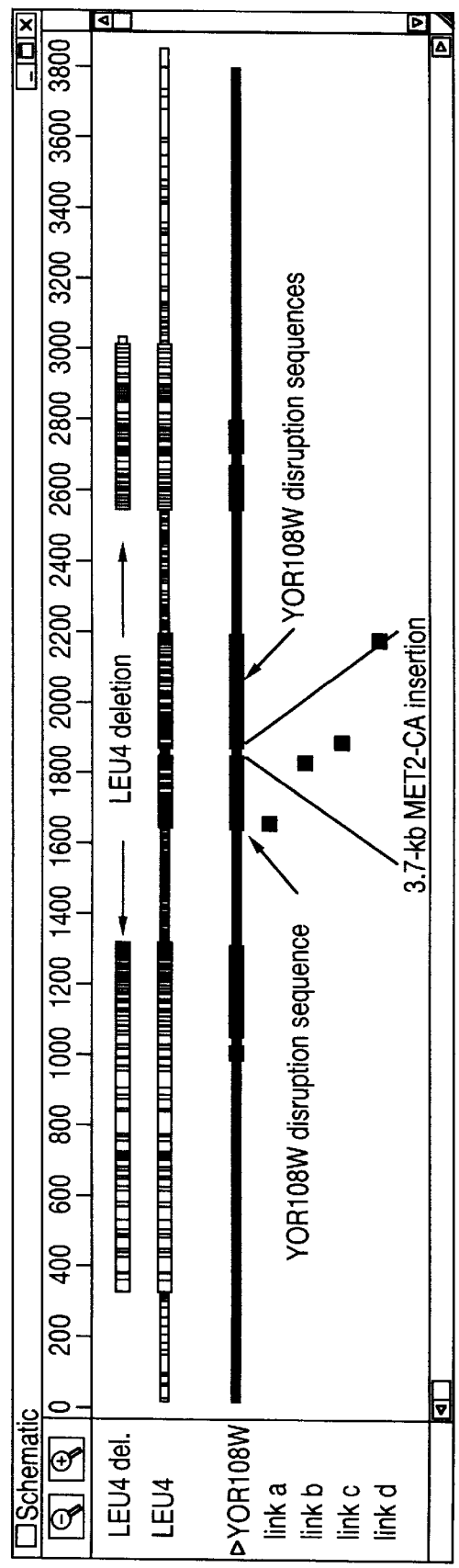
Figure 26:
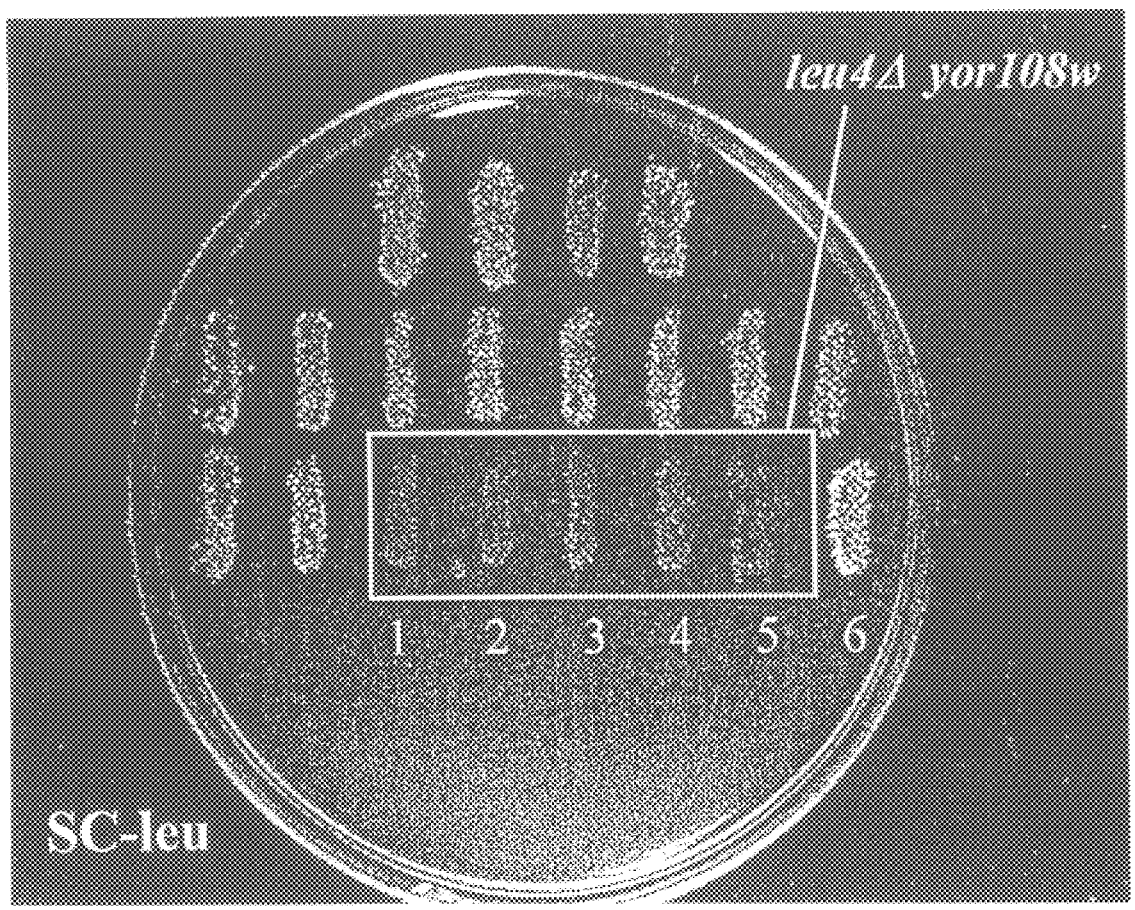

FIG. 6. illustrates Southern hybridizations of brewing yeast strains containing an inactivated allele of the *S. cerevisiae*-like MET14 gene. PFJ439 is C80-CG65 with pPF35 integrated at the MET14-CE locus, the Southern blot shows both the WT (wild-type) band and the Δ (deletion) band. PFJ442 is the C80-CG65 derived integration strain before loop-out, containing a gene conversion, therefore only the Δ-band is present. PFJ448-PFJ452 are loop-outs of PFJ442 being G418-sensitive and having only the Δ-band. As probe was used the XbaI-NdeI fragment from MET14;

FIG. 7 shows the fermentation profile of strain M204 (reference), PFJ501 and PFJ514 from 1st, 2nd and 3rd brew generations, respectively from a 50 L pilot fermentation. Gravity of the wort is calculated as % Plato;

FIG. 8 shows the number of cells from 50 L fermentation of strain M204 (reference), PFJ501 and PFJ514 from three brew generations;

FIG. 9 illustrates sequence homology between methionine sulphoxide reductase genes from different organisms and yeast ORF YER042w. EcPMSR, *Escherichia coli* peptide methionine sulphoxide reductase (Rahman et al., 1992); BtPMSR, *Bos taurus* peptide methionine sulphoxide reductase (Moskovitz et al., 1996); AtPMSR, *Arabidopsis thaliana* peptide methionine sulphoxide reductase (Genbank accession X97326); FaPMSR, *Fragaria x ananassa* (strawberry) peptide methionine sulphoxide reductase (Genbank accession Z69596);

FIG. 10 shows a one-step gene disruption approach employed for deletion of ORF YER042w in *S. cerevisiae* and confirmative PCR reaction;

FIG. 11 shows toxicity of ethionine sulphoxide (EthSO) in wild-type yeast (M1997) and in strain JH465 (ΔYER042w). 200 μl of a 0.1 M DL-ethioninesulphoxide solution were applied to the filter strips, and 50 μl of the yeasts in water suspension were applied to the ethioninesulphoxide-gradient. The plates were incubated at 30° C. for 4 days;

FIG. 12 illustrates growth in liquid culture (YPD or SD media) of a wild-type yeast strain and strain JH465;

FIG. 13 illustrates production of DMS from DMSO added to liquid growth media or already present in brewer's wort. A: M1997, SD; B: JH465, SD; C: M1997, SD+1 ppm DMSO; D: JH465, SD+1 ppm DMSO; E: M1997, SD+10 ppm DMSO; F: JH465, SD+10 ppm DMSO; G: M1997, SD+100 ppm DMSO; H: JH465, SD+100 ppm DMSO; I: M1997, MP; J: JH465, MP; K: M1997, MP+1 ppm DMSO; L: JH465, MP+1 ppm DMSO; M: M1997, MP+10 ppm DMSO; N: JH465, MP+10 ppm DMSO; O: M1997, MP+100 ppm DMSO; P: JH465, MP+100 ppm DMSO; Q: M1997, wort (autoclaved); R: JH465, wort (autoclaved); S: M1997, wort (fresh); T: JH465, wort (fresh);

FIG. 14 shows alleles of *S. cerevisiae* YER042w in *S. carlsbergensis*, *S. monacensis* and the allodiploid maters of *S. carlsbergensis*, C80-CG110 and C80-CG65;

FIG. 15 is a schematic showing of feed-back inhibition of threonine on its own biosynthetic pathway and its supposed effect on the sulphur metabolism in Saccharomyces yeasts;

FIG. 16 illustrates assay for hydrogen sulphide production on BIG-YNB plates with selected strains with reduced hydrogen sulphide production (strains, JH442, JH443 and JH444). Strain M204 was used as the reference *S. carlsbergensis* production strain;

FIG. 17 is an outline of the strategy used to make mutants of allotetraploid brewing yeasts with enhanced hydrogen sulphide production;

FIG. 18 illustrates assay for hydrogen sulphide production on BIG-YNB plates with selected strains with enhanced hydrogen sulphide production (strains JH506, JH515, JH516 and JH517). Strain M204 was used as the reference *S. carlsbergensis* production strain;

FIG. 19 shows production of methylthioacetate, MeSAc (Strains M204, JH506, JH515, JH516, JH517, JH442, JH443 and JH444) or ethylthioacetate, EtSAc (Strains M204, JH506, JH515, JH516 and JH517). Numbers are means of three fermentation experiments;

FIG. 20 shows the production of ethanethiol (EtSH), methylthioacetate (MeSAc) and ethylthioacetate (EtSAc) from a reference production strain (Prod. strain), a strain with high hydrogen sulphide production (met2Δ) and a strain without hydrogen sulphide production (met10Δ);

FIG. 21 is a map of the LEU4 promoter and open reading frame (ORF). Relevant restriction sites are indicated. DNA sequences used for restriction maps and PCR amplifications were obtained from the Saccharomyces Genome Database (http://genome-www.stanford.edu/Saccharomyces/). Sizes are in bp. The shown map was made with pDRAW 1.0;

FIG. 22 is a map of PCR generated 1.5 kb leu4Δ fragment. The fragment is shown in the leu4Δ plasmid PMBP97II. The final loop-in plasmid contains an additional 3.7 kb HindIII fragment with MET2-CA from *S. carlsbergensis* (Hansen and Kielland-Brandt, 1994) as selection marker. The MET2-CA fragment was inserted at HindIII (at nt 1881). The plasmid was linearized with AflII. DNA sequences used for restriction maps and PCR amplifications were obtained from the Saccharomyces Genome Database (http://genome-www.stanford.edu/Saccharomyces/). Sizes are in bp. The shown map was made with PDRAW 1.0;

FIG. 23 shows the amino acid sequence (SEQ ID NO:42) of Leu4p. DNA and protein sequences used for restriction maps and PCR amplifications were obtained from the Saccharomyces Genome Database (http://genome-www.stanford.edu/Saccharomyces/). Amino acid residues marked in bold are deleted while residues in underlined italic have been altered;

FIG. 24 is a map of the LEU4 homologue ORF YOR108w on chromosome XV. Useful restriction sites are indicated. DNA sequences used for restriction maps and PCR amplifications were obtained from the Saccharomyces Genome Database (http://genome-www.stanford.edu/Saccharomyces/). Sizes are in bp. The shown map was made with pDRAW 1.0;

FIG. 25 shows nucleotide homology maps of leu4Δ, LEU4 and ORF YOR108w. Disruption linkers for the LEU4 homologue ORF YOR108w as well as MET2-CA insertion points are indicated. DNA sequences used for restriction maps and PCR amplifications were obtained from the Saccharomyces Genome Database (http://genome-www.stanford.edu/Saccharomyces/). Sizes are in bp. The shown alignment was made with MACAW 2.0.5;

FIG. 26 shows a SC-leucine (SC-leu) medium plate containing LEU4$^{fbr}$, LEU4, leu4Δ and leu4Δ yor108w double mutants. Colonies designated 1, 2, 3, 4 and 5 are the leu4Δ yor108w double mutants MBP97-51, MBP97-52, MBP97-53, MBP97-54 and MBP97-55.

Figure 27:
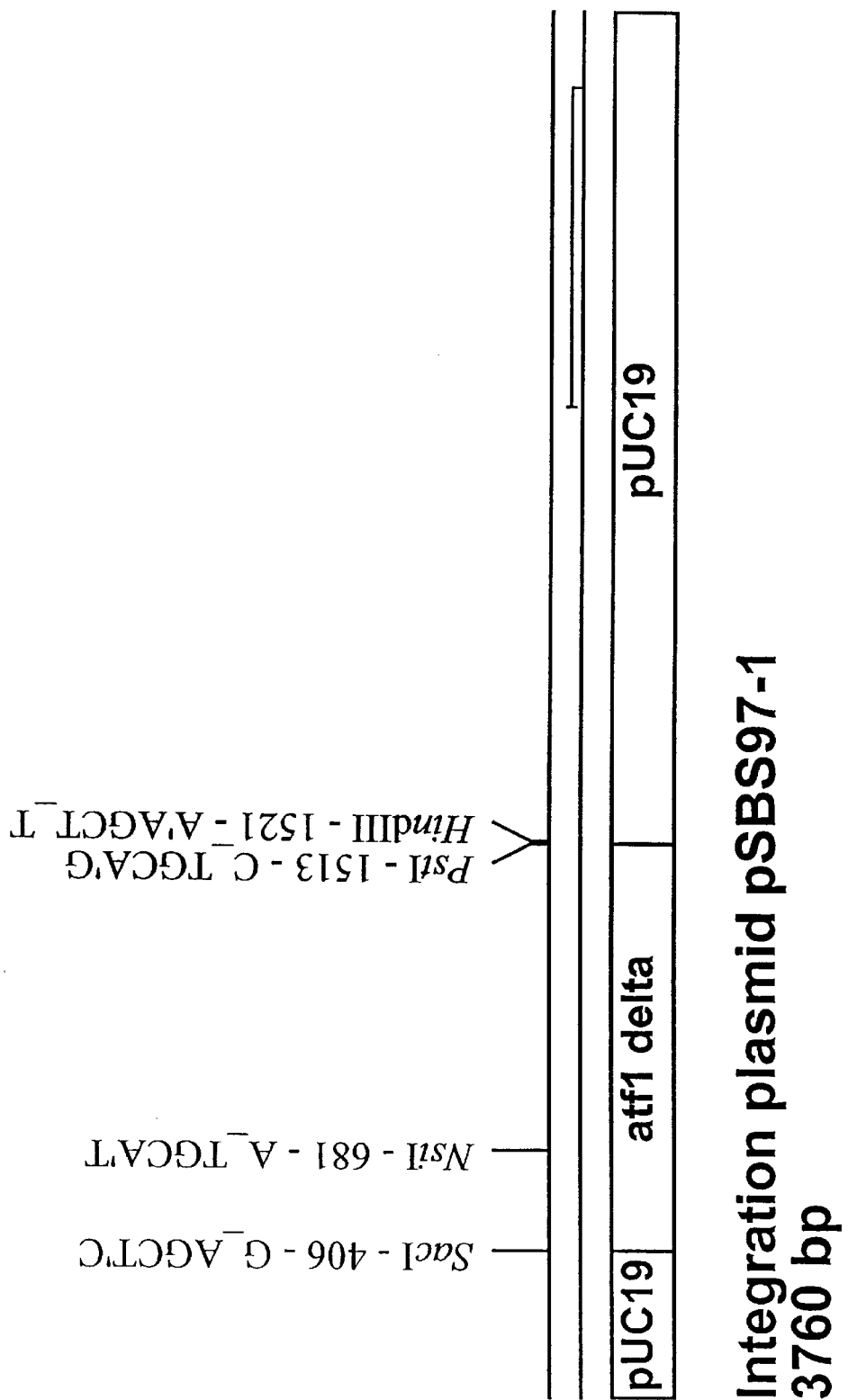
Figure 28:
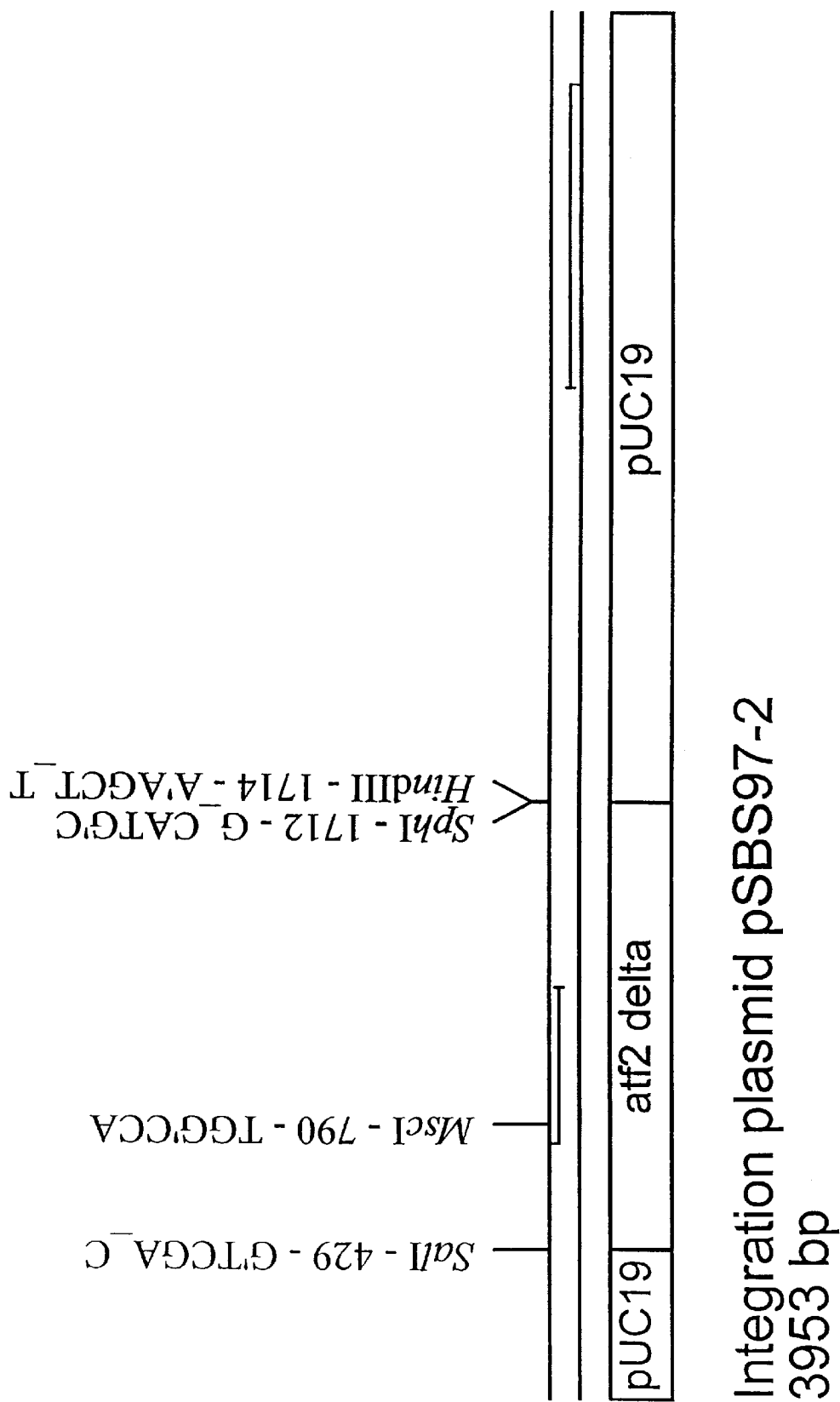
Figure 29:
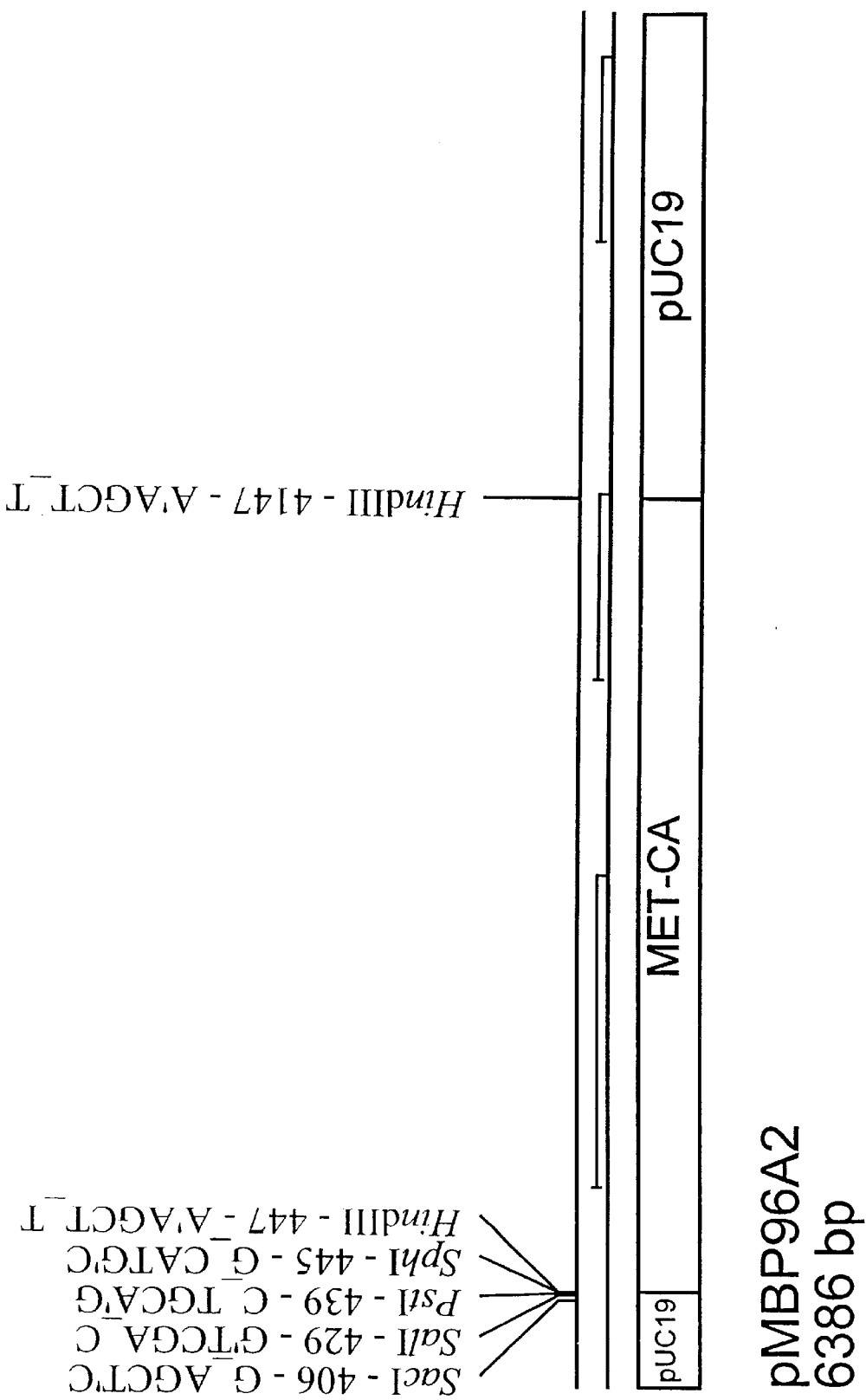
Figure 30:
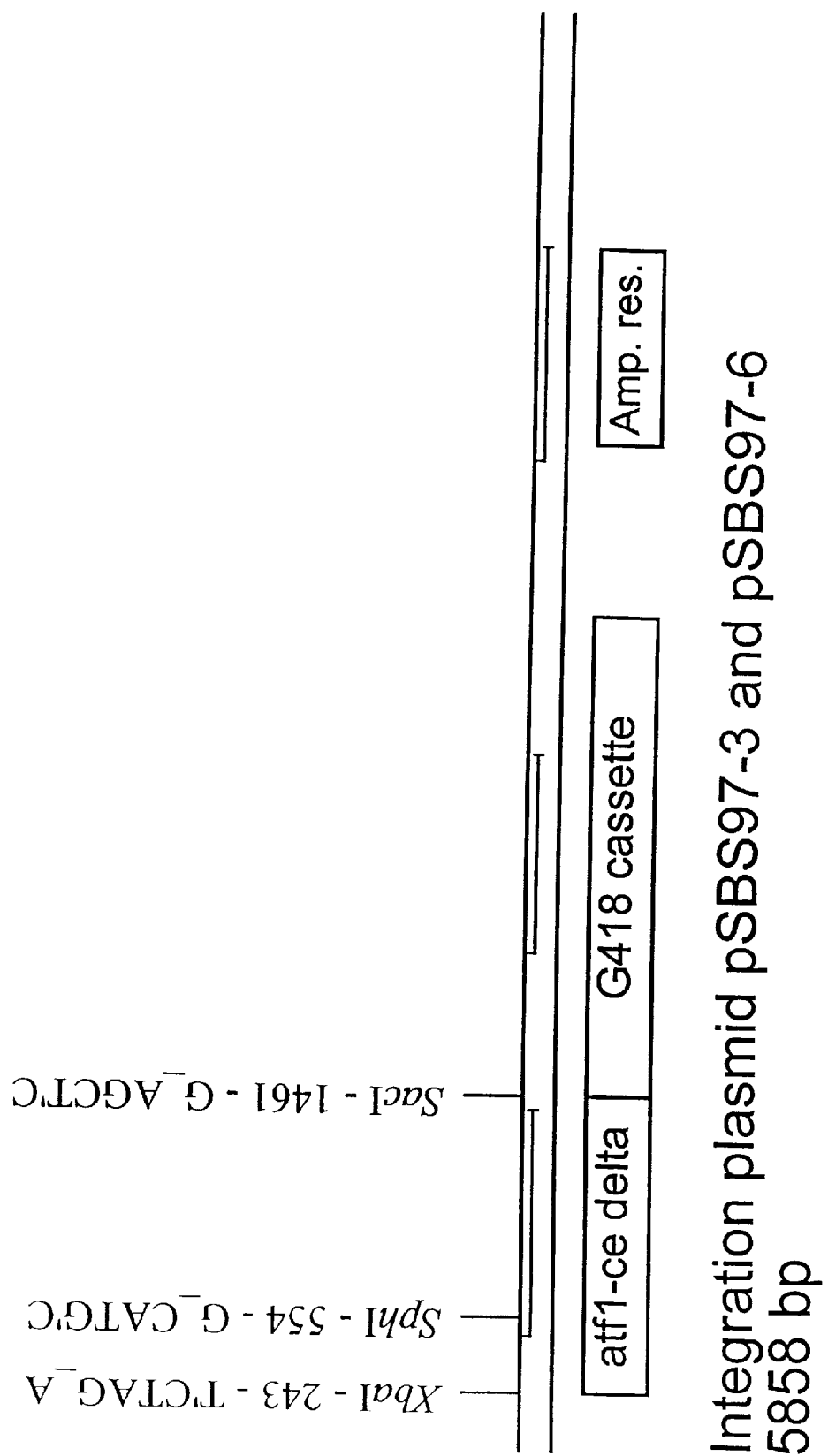
Figure 31:
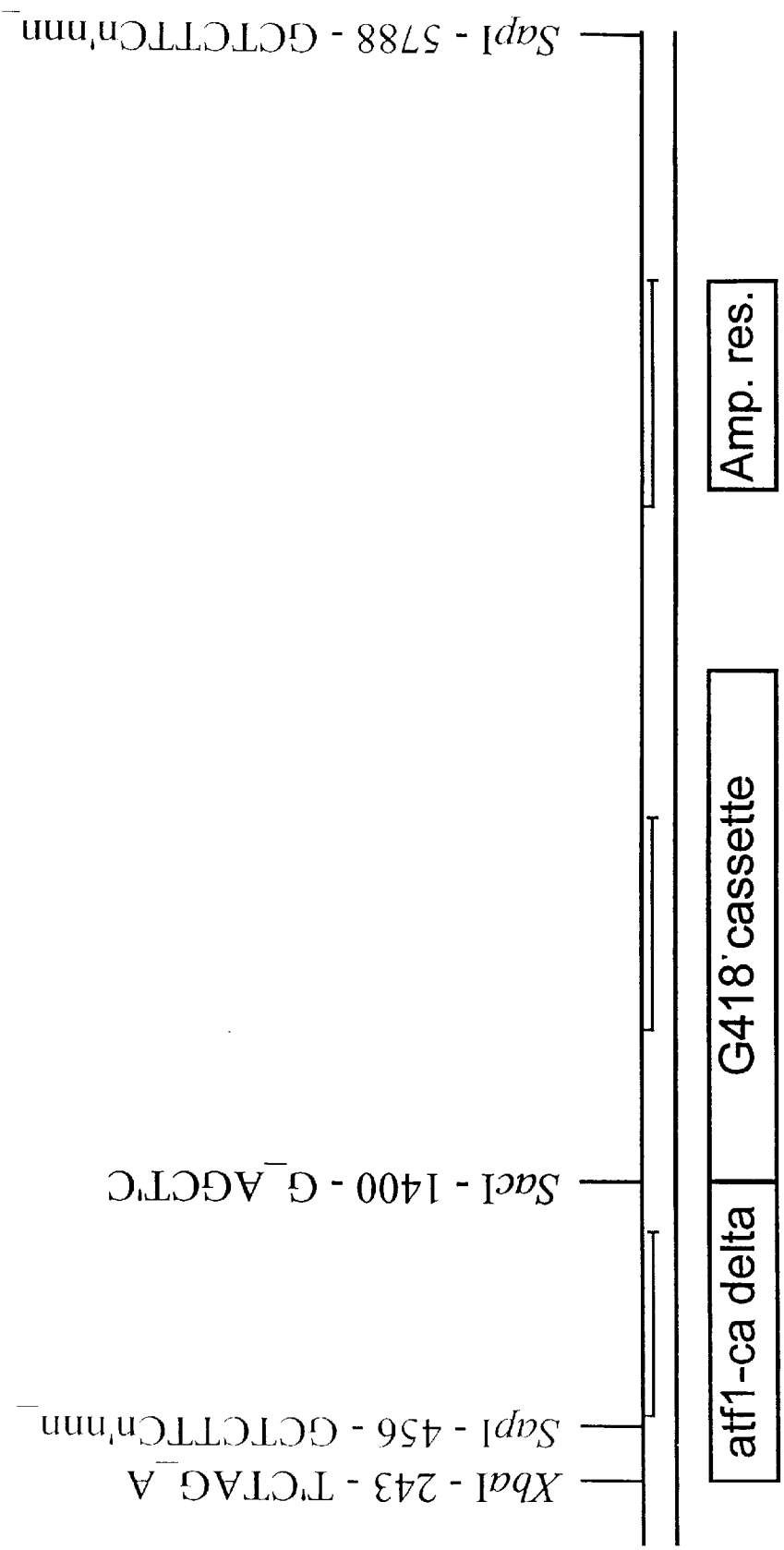
Figure 32:
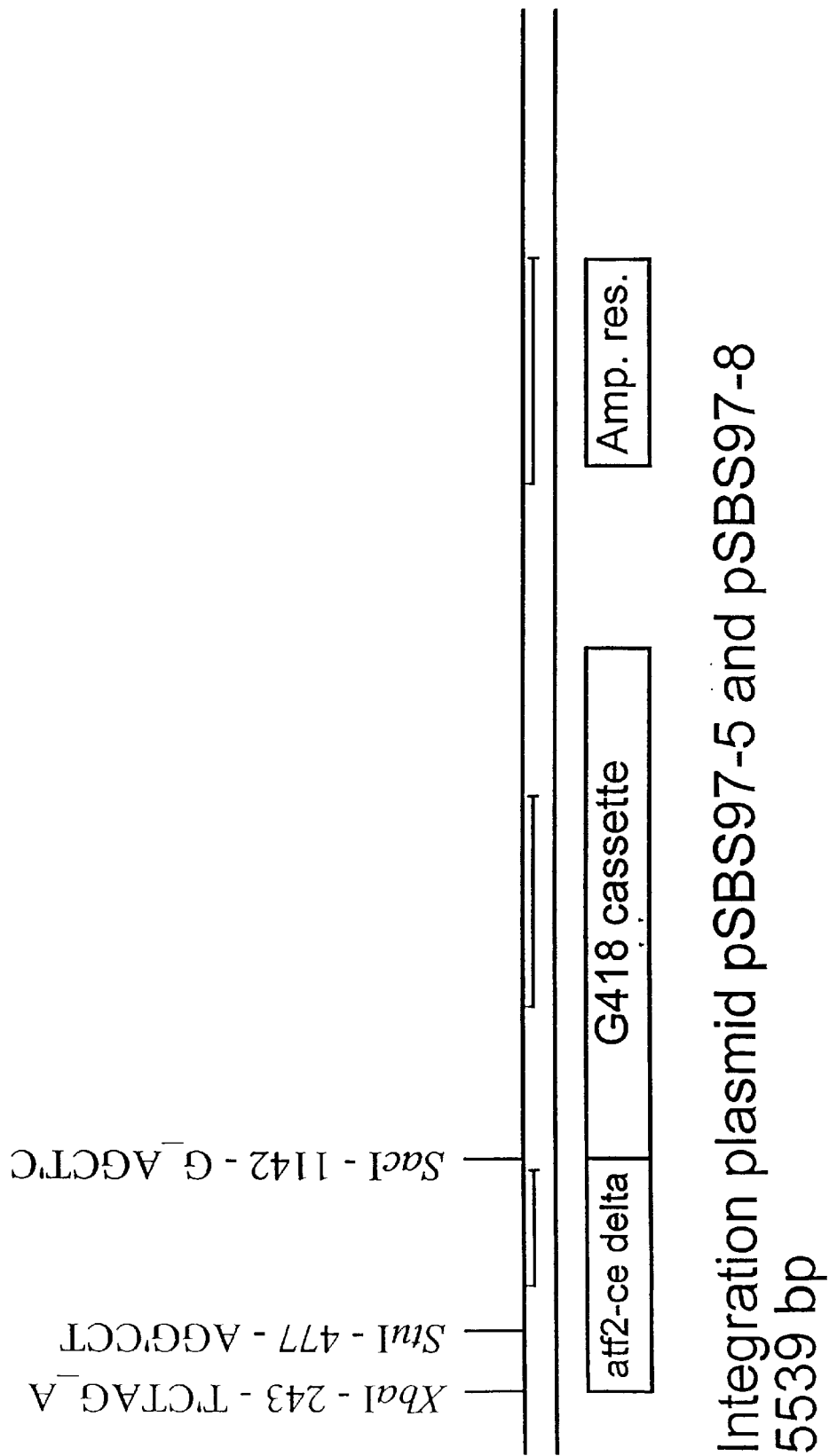
Figure 33:
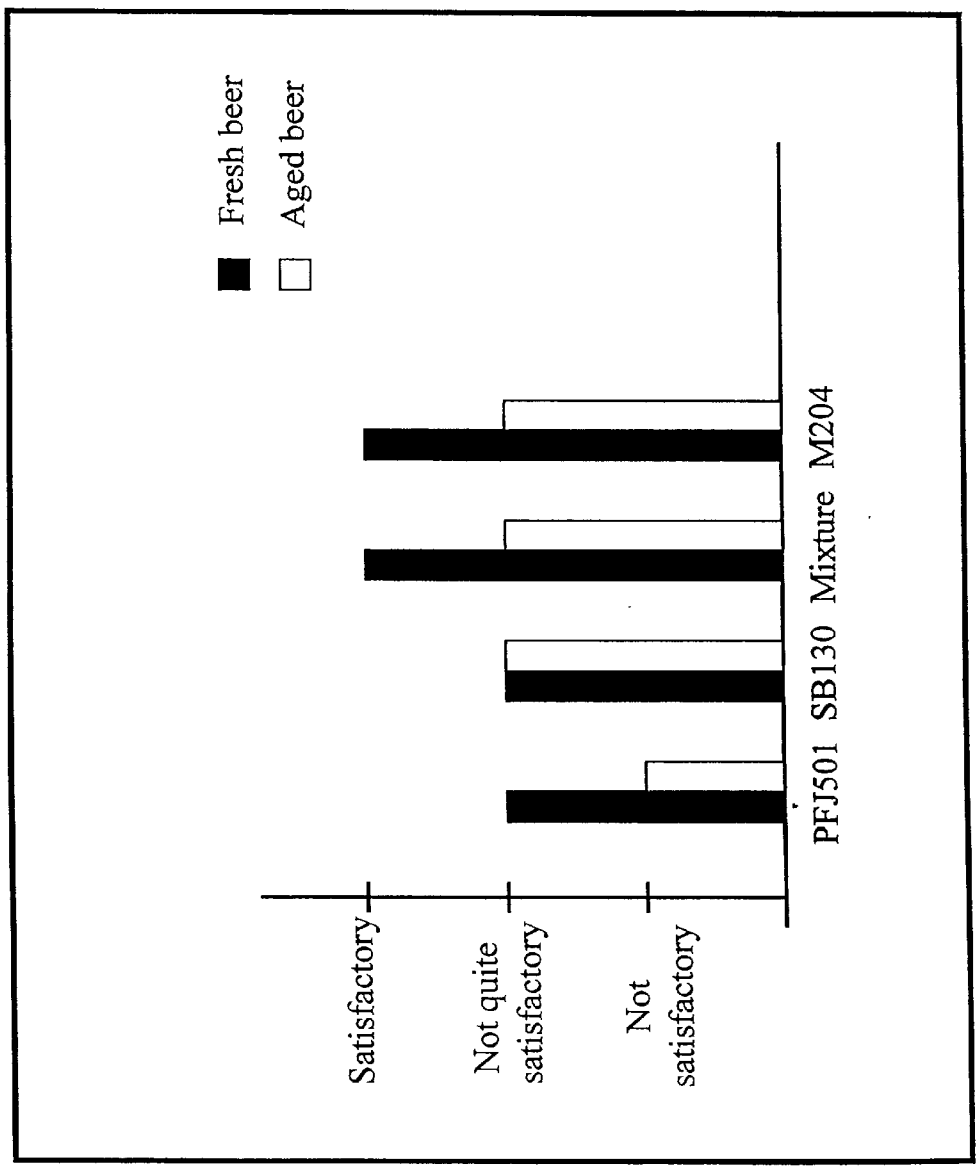

FIG. 27 is a map of part of the integration plasmid pSBS97-1 shown with selected restriction sites. The atf1Δ PCR fragment was ligated into the SacI-PstI sites of pMBP96A2 (see FIG. 29). Besides the indicated pUC19, this plasmid contained an additional 3.7 kb HindIII fragment (at nt 1521) comprising the MET2-CA gene (Hansen and Kielland-Brandt, 1994) as selection marker. Prior to integration, the plasmid was partially digested with NsiI;

FIG. 28 is a map of part of the integration plasmid pSBS97-2 shown with selected restriction sites. The atf2Δ PCR fragment was ligated into the SalI-SphI sites of pMBP96A2 (see FIG. 29). Besides the indicated pUC19, this plasmid contained an additional 3.7 kb HindIII fragment (at nt 1521) comprising the MET2-CA gene (Hansen and Kielland-Brandt, 1994) as selection marker. Prior to integration, the plasmid was linearized with MscI;

FIG. 29 shows the plasmid pMBP96A2 constructed by inserting a 3.7 kb HindIII-fragment comprising the MET2-CA gene from *S. carlsbergensis* (Hansen and Kielland-Brandt, 1994) into the HindIII site of pUC19 (Yanish-Perron et al., 1985). The MET2-CA gene encodes a homoserine acetyl transferase;

FIG. 30 is a map of the integration plasmids pSBS97-3 and pSBS97-6 shown with selected restriction sites. The atf1-ceΔ PCR fragments were ligated into the XbaI-SacI sites of pCH216 (Hadfield et al., 1990). The only difference between the two plasmids being that the template for the PCR fragment in pSBS97-3 was genomic DNA from C80-CG65 and the template for pSBS97-6 was genomic DNA from C80-CG110. Prior to integration, the plasmids were linearized with SphI;

FIG. 31 is a map of the integration plasmids pSBS97-4 and pSBS97-7 shown with selected restriction sites. The atf1-caΔ PCR fragments were ligated into the XbaI-SacI sites of pCH216 (Hadfield et al., 1990). The only difference between the two plasmids being that the template for the PCR fragment in pSBS97-4 was genomic DNA from C80-CG65 and the template for pSBS97-7 was genomic DNA from C80-CG110. Prior to integration, the plasmids were linearized by partial digestion with SapI;

FIG. 32 is a map of the integration plasmids pSBS97-5 and pSBS97-8. The atf2-ceΔ PCR fragments were ligated into the XbaI-SacI sites of pCH216 (Hadfield et al., 1990). The only difference between the two plasmids being that the template for the PCR fragment in pSBS97-5 was genomic DNA from C80-CG65 and the template for pSBS97-8 was genomic DNA from C80-CG110. Prior to integration, the plasmids were linearized with StuI, and FIG. 33 shows the results of a sensory comparative test of batches of beer produced by the following *S. carlsbergensis* strains: PFJ501 having a reduced sulphite production (inactivated in all four MET14 genes), SB130 having increased sulphite production (inactivated in all four MET10 genes coding for sulphite reductase), and strain M204, an industrial lager strain. "Mixture" indicates a composite beer made by mixing the PFJ501 and SB130 batches.

EXAMPLE 1

Construction of *S. carisbergensis* brewer's yeast without production of sulphite 1.1. Summary of the experiments Sulphite, being an antioxidant and flavour stabilizer, plays a key role in preservation of beer taste. In order to be able to control the amount of sulphite in a final beer, it was decided to make a brewer's yeast being deficient with respect to sulphite production. By combining beer from low and high sulphite containing beer batches, it would be possible to make beer with a predetermined amount of sulphite. Furthermore, due to a reduced content of the yeast-derived sulphur compounds, the low-sulphite producing yeast strain would be an appropriate basis for construction of a yeast strain which could be used to produce a taste-neutral beer. Such a beer could potentially form the basis for combination with other beer batches.

*Saccharomyces carlsbergensis* brewer's yeast was inactivated in all four copies of the MET14 gene by disruption combined with classical mutagenesis. Beer produced with this yeast contained no measurable sulphite when bottled and was quite satisfactory with respect to brewing characteristics.

Figure 1:
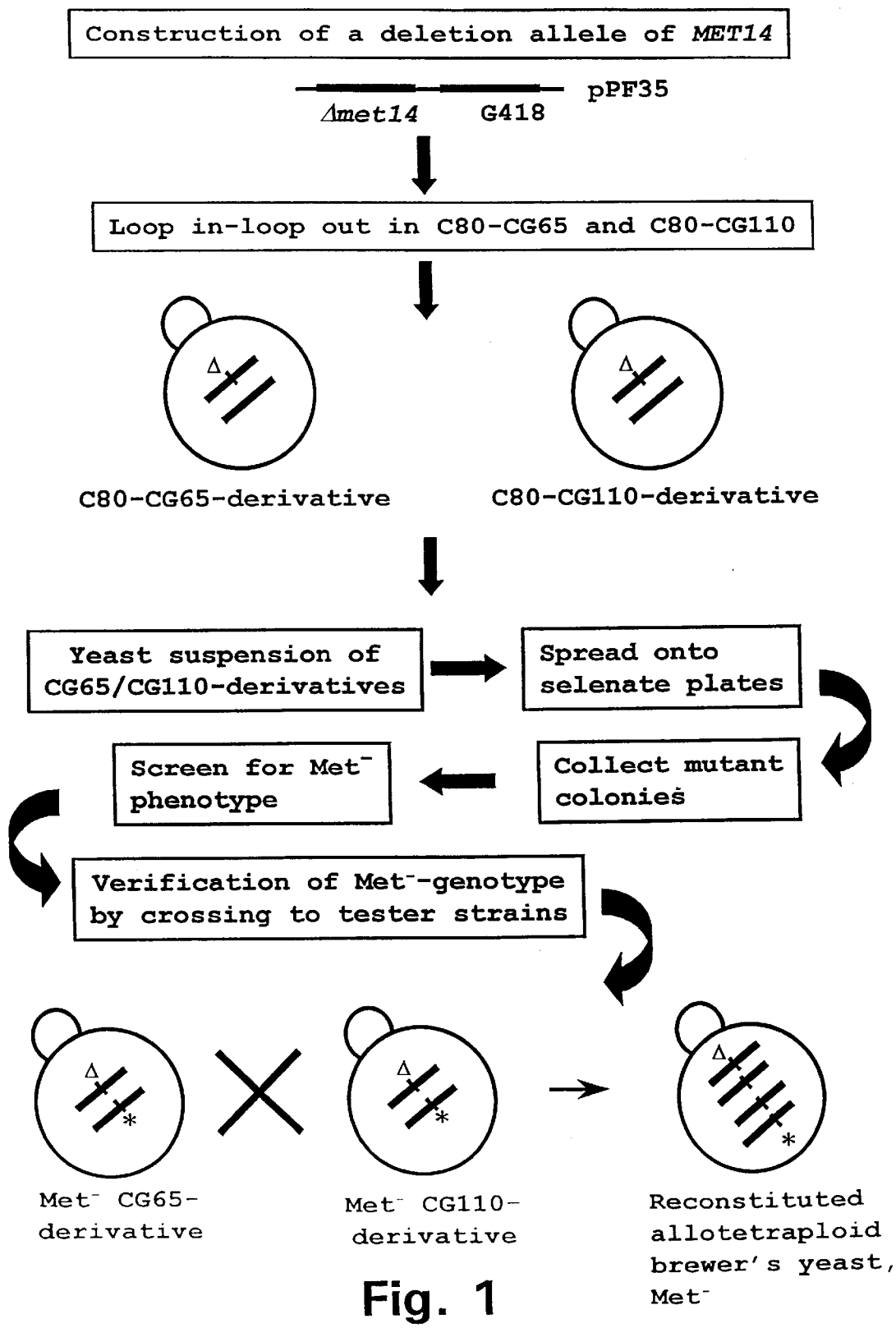
FIG. 1 is a flow diagram of the different steps involved in the construction of a Met⁻ brewer's yeast.

*Saccharomyces carlsbergensis* brewer's yeast is presumably allotetraploid, having two copies of each of two divergent alleles of the genes investigated so far, as reviewed by Kielland-Brandt et al., 1995. In the following is described the construction of *S. carlsbergensis* brewer's yeast strains impaired in their sulphite production by inactivation of all four copies of MET14 (encoding APS kinase, EC 2.7.1.25) using targeted genetical disruption as well as classical breeding methods (FIG. 1). The resulting strains were evaluated with respect to brewing performance. Levels of sulphite and trans-2-nonenal (t2n) were determined, and the beer was evaluated by a trained taste panel.

1.2. Materials and methods
Strains and media

Strains are presented in Table 1.1. Synthetic sulphur-free B-medium was made according to Cherest and Surdin-Kerjan (1992), but modified by the addition of 10 mM ammonium sulphate or 0.2 mM DL-homocysteine thiolactone. YPD complex medium (1% yeast extract, 2% peptone, 2% glucose) or synthetic complete medium (SC, Sherman, 1991) was used for all experiments, except the 50 L-scale fermentations, where brewer's wort with a gravity of 14.5% Plato was used. Geneticin (G418) was added (30 g/L) to YPD plates for selection of transformants of brewer's yeast and the following screening of transformants. 5 mM of sodium selenate was added to B-medium plates for the selection of selenate-resistant yeast strains.

TABLE 1.1

Strains of Saccharomyces used in the experiments.

| Strain | Mating type | Genotype | Ploidy | Origin |
|---|---|---|---|---|
| M204 | nm | | 2 + 2 | Lager production strain |
| C80-CG65 | a | | 1 + 1 | Meiotic segregant of M204 |
| C80-CG110 | α | | 1 + 1 | Meiotic segregant of M204 |
| T224 | nm | | 2 + 2 | Lager production strain |
| CBS1503** | nm | | 1 | CBS |
| PFJ445 | a | deficient of chr. XI* | 1 + 1 | Derivative of C80-CG65 |
| PFJ448 | a | met14-ca-MET14-CE | 1 + 1 | Derivative of C80-CG65 |
| PFJ449 | a | " | 1 + 1 | " |
| PFJ450 | a | " | 1 + 1 | " |
| PFJ451 | a | " | 1 + 1 | " |
| PFJ452 | a | " | 1 + 1 | " |
| PFJ457 | a | met14-ca-met14*-ce | 1 + 1 | Derivative of PFJ450 |
| PFJ458 | a | " | 1 + 1 | Derivative of PFJ449 |
| PFJ459 | a | " | 1 + 1 | " |
| PFJ460 | a | " | 1 + 1 | " |
| PFJ461 | a | " | 1 + 1 | Derivative of PFJ451 |
| PFJ462 | a | " | 1 + 1 | " |
| PFJ463 | a | " | 1 + 1 | " |
| PFJ464 | a | " | 1 + 1 | " |
| PFJ465 | a | " | 1 + 1 | Derivative of PFJ452 |
| PFJ466 | a | " | 1 + 1 | " |
| PFJ467 | α | met14-ce MET14-CA | 1 + 1 | Derivative of C80-CG110 |
| PFJ468 | α | " | 1 + 1 | " |
| PFJ530 | α | met14-ce met14*-ca | 1 + 1 | Derivative of PFJ468 |
| PFJ501 | nm | met14-ce/met14-ce met14*-ca/met14*-ca | 2 + 2 | Cross between PFJ459 and PFJ530 |
| PFJ502 | nm | met14-ce/met14-ce met14*-ca/met14*-ca | 2 + 2 | Cross between PFJ460 and PFJ530 |
| PFJ506 | nm | met14-ce/met14-ce met14*-ca/met14*-ca | 2 + 2 | Cross between PFJ461 and PFJ530 |
| PFJ509 | nm | met14-ce/met14-ce met14*-ca/met14*-ca | 2 + 2 | Cross between PFJ462 and PFJ530 |
| PFJ510 | nm | met14-ce/met14-ce met14*-ca/met14*-ca | 2 + 2 | Cross between PFJ462 and PFJ530 |
| PFJ514 | nm | Met14-ce/met14-ce Met14*-ca/met14*-ca | 2 + 2 | Cross between PFJ463 and PFJ530 |
| K396-22B | α | spo11 ura3 ade1 his1 leu2 lys7 met3 trp5 | 1 | S. Klapholz |
| X2928-3D(1C) | α | ade1 gal1 leu1 his2 ura3 trp1 met14 | 1 | |
| S288C** | α | MAL GAL2 | 1 | YGSC, R. K. Mortimer |

The genotype of all brewer's yeast strain are wild-type except for the MET14 locus as described. This strain seems to have lost the *S. cerevisiae*-like chr. XI after an integration attempt (P. F. Johannesen, unpublished). ** All strains are *S. carlsbergensis* derivatives except CBS1503 (*S. monacensis*) and S288C (*S. cerevisiae*). CBS: Centraal Bureau voor Schimmelcultures, Baarn, Netherlands; YGSC: Yeast Genetics Stock Centre, University of California, Berkeley, Calif., U.S.A. Abbreviations: 1+1, allodiploid; 2+2, allotetraploid; nm, non mater.

Yeast transformation

Transformation of yeast was carried out according to Schiestl and Gietz (1989). When transforming brewer's yeast the transformed cells (washed with Tris-EDTA buffer) were resuspended in 100 μl of YPD medium and left at room temperature over night allowing the cells to recover and express the neomycin phosphotransferase gene before plating on selective medium.

Extraction of genomic DNA

Genomic DNA was extracted from cells mechanically broken by use of glass beads according to Hoffman and Winston (1987). DNA was extracted from 10 ml yeast cultures. For Southern analysis 10 μg DNA solution was used.

Southern blot hybridization

Genomic DNA was digested with appropriate restriction enzymes and separated on 1% agarose gels. DNA was transferred to Hybond-N nylon membranes by capillary blotting. Covalent binding of the DNA to the filter was mediated by UV-irradiation. The filters were hybridized with suitable $^{32}$P-labelled DNA-probes at high stringency (65° C., washed with 0.1×SSC). The signals were detected by using a PhosphorImager (Molecular Dynamics, Sunnyvale, Calif.).

Sequencing

DNA for sequencing was prepared using the Wizard® Plus Mini-preps DNA Purification System (Promega). Sequence reactions were made according to protocols from the manufacturer using PRISM™ AmpliTaq® FS Dye Terminator Cycle Sequencing kit (Applied Biosystems), in a Perkin Elmer PCR machine. The sequencing reactions were processed in an Applied Biosystems 373A DNA Sequencer, according to the 373A User's manual.

PCR

Synthesizing the MET14 gene using S. monacensis DNA as template and homoeologous primers designed from S. cerevisiae chromosome XI, required low stringency in the PCR reaction: 50–100 ng genomic DNA, 0.2 mM of each dNTP, 1.0 μM of each oligoprimer, reaction buffer including up to 4 mM magnesium chloride, 2.5 u Taq-polymerase (Perkin-Elmer), millipore water up to 100 μl. Denaturation was at 94° C. for 1 min., annealing at 45–60° C. for 2 min. (Generally a product was only seen at the lowest temperatures), extension at 72° C. for 3 min., and 25–30 cycles were run. All reactions were started by an initial denaturation at 94° C. for 4 min. and terminated by an extension at 72° C. for 10 min. Amplification of the S. carlsbergensis-specific MET14 gene for sequencing was accomplished by using Expand™ High Fidelity PCR System (Boehringer Mannheim), a mixture of Taq-polymerase and Pwo-polymerase the last having proof-reading potency. Reaction conditions differed from the above as follows: 2.5 mM magnesium chloride in the buffer, annealing at 52° C. for 2 min., extension at 72° C. for 3 min., and only 20 cycles were run. A Stratagene Robocycler® Gradient 40 Temperature Cycler was used for all PCR reactions.

Reconstitution of allotetraploid brewer's yeast from allodiploid maters

Crossing of the allodiploid maters to reconstitute an allotetraploid brewer's yeast was performed according to Gjermansen and Sigsgaard (1981) with some modifications. Small amounts of cells were mixed on a YPD plate. The strains were allowed to mate for 24 hours at room temperature followed by inoculation into YPGal medium (1% yeast extract, 2% peptone, 2% galactose (Hansen and Kielland-Brandt, 1996b) as carbon source) and left for 2 days of growth at room temperature. Some of the cultures were spread for single colonies on YPGal plates. Hybrids showed a markedly better growth compared with the two allodiploid maters on this carbon source. Hybrids can be isolated as well-growing yeast colonies.

Fermentation at 50 L scale

After propagation, yeast was inoculated in brewer's wort at $1.5 \times 10^7$ cells/ml in 50 L fermentation vessels. Fermentation was performed at 13° C. The yeast was harvested after 10 days and the beer was left in the vessels for a period of 8–12 days of lagering. The harvested yeast was used for the subsequent brewing generations.

Other analyses

Either the supernatant from centrifuged samples or bottled beer were assayed for total $SO_2$ using headspace with Sulfur Chemiluminescence Detector (SCD)™ (Lowe and Dreyer, 1997). Acetaldehyde was measured by gas liquid chromatography. Trans-2-nonenal was measured by GC-MS. Beer gravity was determined using an Anton Paar DMA 46 density meter (Anton Paar K. G., Graz, Austria).

1.3. Results (i) Evaluation of the content of MET14 gene alleles in S. carlsbergensis In order to determine the content of MET14 genes in S. carsbergensis brewer's yeast a Southern analysis was made using genomic DNA from different Saccharomyces yeasts. Genomic DNA from S288C (haploid standard S. cerevisiae laboratory strain), CBS1503 (S. monacensis), C80-CG65 (allodiploid a-mater of S. carlsbergensis production yeast), C80-CG110 (allodiploid α-mater of S. carlsbergensis production yeast) and T224 (allotetraploid production yeast) were used in the analysis.

Figure 2:
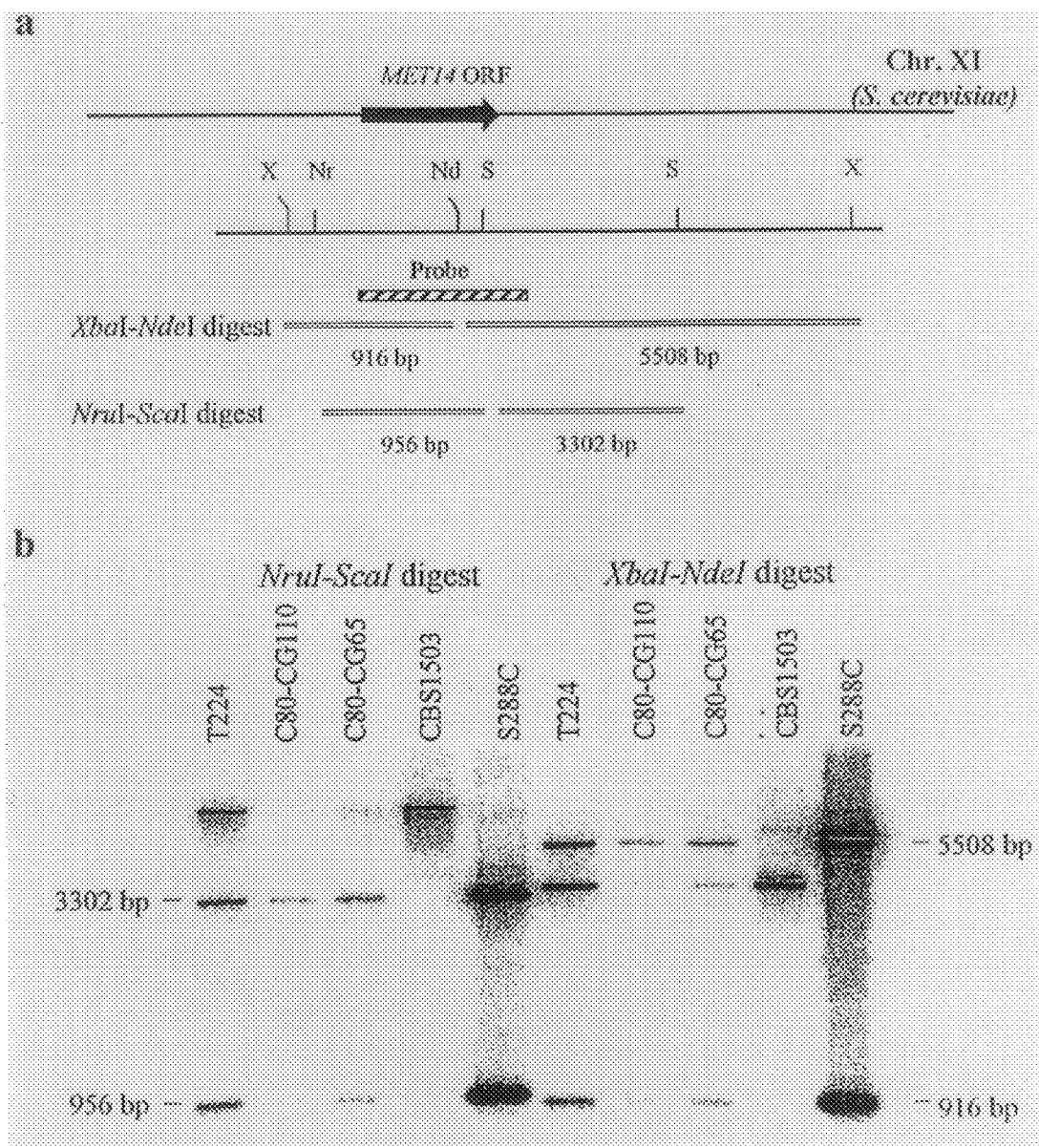
FIG. 2a is a schematic illustration of the restriction map of the *S. cerevisiae* MET14 genomic region and the expected sizes of fragments that will be visualized in a Southern analysis employing the depicted restriction endonucleases.
FIG. 2b shows a Southern blot with DNA from T224, allotetraploid brewer's yeast, C80-CG65 and C80-CG110, allodiploid brewer's yeast, CBS1503, *S. monacensis* and S288C, *S. cerevisiae;*

DNA was digested with two different combinations of restriction enzymes, NruI+ScaI and XbaI+NdeI. The Southern blot was hybridized using a 1150 bp fragment of the MET14 as a probe (FIG. 2). A distinct pattern of bands was seen in both S. cerevisiae and S. monacensis, whereas in T224, C80-CG65 and C80-CG110 a pattern which is a combination of those with S. monacensis and S. cerevisiae was seen. This shows that the T224 production yeast as well as the two allodiploid maters contain two different alleles of MET14 (one hereinafter denoted MET14-CE) like the gene found in S. cerevisiae, and one (hereinafter denoted MET14-CA) like the MET14 gene found in S. monacensis.

(ii) Isolation of the S. cerevisiae-like MET14 gene from brewer's yeast

In order to be able to make a deletion allele of the S. cerevisiae-like MET14 gene, the MET14-CE gene was cloned from brewer's yeast. This was performed as it was assumed that the MET14-CE gene would not be exactly identical to the MET14 gene from S. cerevisiae, and as a deletion construct based on MET14-CE would make it possible not to introduce foreign DNA into the brewer's yeast.

The gene was cloned by complementation of a S. cerevisiae met14 strain using a S. carlsbergensis library (Casey, 1986). The complementation cloning has been described (Johannesen, 1994) and the resulting clone #42 (in an YRp17 vector, Botstein and Davis,1982) was mapped by restriction analysis. It turned out that the MET14 gene differed from the MET14-CE gene by at least the unique SalI site which is not present in the MET14-CE gene.

A ClaI-SalI fragment of approximately 2,400 bp from clone #42 was subcloned into vector pRS316 (Sikorski and Hieter, 1989). The ClaI site is in the MET14-CE insert whereas the SalI site is in YRp17 (276 bp of the vector sequence between the BamHI site and the SalI site are brought along). The resulting plasmid is pPF28, and the insert can be cut out with a ClaI-SalI restriction digest (FIG. 5).

(iii) Construction of a deletion allele of the MET14-CE gene.

A deletion allele of the S. cerevisiae-like MET14 gene was constructed, enabling inactivation of the MET14-CE gene in S. carlsbergensis brewer's yeast. Plasmid pPF28 contains an insert of about 2,400 bp including the S. cerevisiae-like MET14 gene in the pRS316 vector (Sikorski and Hieter, 1989). This plasmid was digested with HpaI and NruI, both cutting uniquely, thus deleting a piece of 471 bp covering the promoter region and the first part of the open reading frame of MET14-CE. The plasmid was religated, as both enzymes generated blunt ends, resulting in plasmid pPF33. The insert of pPF33 could be cut out with ClaI and SalI. This fragment was blunt end ligated into the integration vector pCH216 (Hadfield, 1994), opened in SacI and blunted. This vector contains the G418 (geneticin) resistance gene, usable for selection of transformation of brewer's yeast. The resulting plasmid, pPF35 (FIG. 5a), can be linearized by cutting with SacI in the MET14-CE coding region. Linearization of pPF35 will direct the integration preferentially to take place through the MET14-CE gene (according to Orr-Weaver et al., 1981).

(iv) Use of the deletion allele of the MET14-CE gene to inactivate the S. cerevisiae-like MET14 alleles present in the allodiploid maters C80-CG65 and C80-CG110

In order to obtain a brewer's yeast without sulphite production it was decided to inactivate all four copies of MET14 in this yeast. The strategy that was chosen was based on the capacity of the yeast to allow for homologous recombination between a deletion allele of a gene on a plasmid and the wild-type gene on the chromosome using the loop-in/loop-out method (Scherer and Davis, 1979). Each of the two allodiploid maters from the C80-CG65 and C80-CG110 strains of brewer's yeast presumably contains one copy of each version of MET14 (FIG. 2). Hybrids made from the two maters result in reconstituted allotetraploid brewer's yeast with a normal brewing performance (Gjermansen and Sigsgaard, 1981).

The MET14-CE genes in C80-CG65 and C80-CG110, respectively were disrupted using a deletion allele of the gene on plasmid pPF35 (FIG. 5a). Construction of this plasmid is described in the section above. Before transformation of C80-CG65 and C80-CG110 with pPF35, the plasmid was linearized by digestion with SacI in order to direct the integration to the MET14-CE locus (Orr-Weaver et al., 1981). Transformants were selected on YPD plates with geneticin. Geneticin resistant strains were picked and analyzed by Southern hybridizations to confirm correct integrations (data not shown). Genomic DNA was digested with XbaI and NdeI and the Southern blots were probed with a XbaI-NdeI fragment from MET14.

A secondary recombination event is necessary in order to loop-out the vector DNA and either the wild-type or deletion allele of MET14-CE. Two integration strains derived from each mater were selected for the loop-out procedure (Scherer and Davis, 1979). These were grown to stationary phase in 10 ml YPD medium without geneticin, 100 µl culture was reinoculated in 10 ml YPD and grown to stationary phase, and the procedure repeated once more. Approximately 20,000 cells from each culture were spread onto YPD plates and the colonies were replica-plated onto YPD supplemented with geneticin. Geneticin-sensitive colonies were isolated and analyzed by Southern hybridization to identify clones in which wild-type MET14-CE have been substituted with the deletion allele.

In one of the C80-CG65 transformants a gene conversion appeared to have taken place, resulting in two copies of the deletion allele on the chromosome, separated by the vector sequences. After successful loop-out of the vector sequences in this particular transformant, only the deletion allele could remain on the chromosome. Strains PFJ448, PFJ449, PFJ450, PFJ451 and PFJ452 are derivatives of this strain, all inactivated in the S. cerevisiae-like MET14 gene (FIG. 6). Strain PFJ467 and PFJ468 are the corresponding C80-CG110 derivatives, although they were made from a transformant containing both a wild-type and a deletion allele of MET14-CE (data not shown).

(v) Inactivation of the S. carlsbergensis-specific MET14 alleles in PFJ449, PFJ450, PFJ451, PFJ452 and PFJ468 by employing mutagenesis and resistance towards heavy metal ions To inactivate the S. carlsbergensis-specific MET14 alleles in PFJ449, PFJ450, PFJ451, PFJ452 and PFJ468, respectively, a "shortcut" strategy was used, taking advantage of the toxicity of certain sulphate analogs. It has been shown (Breton and Surdin-Kerjan, 1977) that mutant strains of S. cerevisiae that are resistant to selenate and chromate (sulphate analogs) are mainly mutants in the MET3 gene, but some are also in MET14 or MET16. The strains described in the previous section only contain one active copy of MET14 (MET14-CA), due to deletion of the other (MET14-CE). When screening for mutants from these strains on selenate medium, we expected only to find met14-ca mutants, as probably two MET3 and MET16 genes are present in the allodiploid maters.

The five strains PFJ449, PFJ450, PFJ451, PFJ452 and PFJ468 were cultured to stationary phase in YPD medium, cells were washed in water and aliquots of 200 µL culture were spread onto plates with B-medium and 5 mM sodium selenate. The yeast was mutagenized using UV irradiation corresponding to about 50% killing. Mutants were isolated after 5–8 days growth at 20° C. Only mutants that were methionine auxotrophs were kept, as only these could be possible met14-ca strains. Such auxotrophs were then test-crossed to S. cerevisiae strains carrying mutations in either MET3 or MET14. Complementation of the methionine requirement was seen with the mutant met3-strain, but not in the crosses involving the mutant met14 strain. Ten strains having a C80-CG65 background were isolated: PFJ457, PFJ458, PFJ459, PFJ460, PFJ461, PFJ462, PFJ463, PFJ464, PFJ465 and PFJ466. Only one C80-CG110 derivative was isolated, viz. PFJ530. The strains were also tested for reversion to methionine prototrophy and they showed a low degree of reversion. The nature of the mutations obtained via selection on selenate medium are unknown, and might not lead to complete inactivation of the MET14-CA genes. Therefore, it would be suitable to produce mutants, in which all MET14 genes are inactivated in a defined manner by recombinant methods.

(vi) Isolation and characterization of the S. monacensis MET14 gene

As described above, S. carlsbergensis brewer's yeast contains two different alleles of MET14 of which the S. cerevisiae-like allele has been characterized previously (Korch et al., 1991). In order to inactivate all MET14 gene activity in a S. carlsbergensis brewer's yeast, it was necessary to isolate and characterize the S. carlsbergensis-specific MET14 gene as well. For unknown reasons, it was not possible to isolate this gene by genetic complementation of an S. cerevisiae met14 mutant strain with an S. carlsbergensis gene library (Casey, 1986). Although 500,000 transformed colonies were screened only the S. cerevisiae-like allele was found.

Instead, the sequence information from S. cerevisiae was used to design oligoprimers which enabled PCR amplification of the *S. monacensis* MET14 gene from *S. monacensis* DNA template (FIG. 3). This strategy relied on two assumptions: i) that the *S. carlsbergensis*-specific MET14 gene is homologous to the only MET14 gene found in *S. monacensis*, and ii) that the gene order in the *S. cerevisiae* and the *S. monacensis* MET14 regions is conserved and the DNA sequences sufficiently related to allow annealing of the *S. cerevisiae*-derived primers to the *S. monacensis* DNA.

Fragment B (FIG. 3) was amplified using oligoprimers #3 and #4 (Table 1.2.) based on the sequence of the *S. cerevisiae* MET14 open reading frame. Likewise, fragment A and C (FIG. 3) were synthesized using oligoprimers #1, #2, #5 and #6 (Table 1.2), also designed by using the sequence information from *S. cerevisiae* chromosome XI. After sequencing of the 3'- and 5'-ends (fragments A and C) of the *S. monacensis* MET14 gene, oligoprimers were designed from the nucleotide sequence of these regions, showing only a low degree of homology to the same regions in the *S. cerevisiae*-like MET14 gene. As template for the synthesis of the full-length *S. carlsbergensis*-specific MET14 gene a derivative of C80-CG65, PFJ445 was used. This strain appears to be deficient of the entire *S. cerevisiae*-like chromosome XI (data not shown) on which MET14-CE is found, and only to contain the *S. carlsbergensis*-specific Chr. XI. PCR amplification using the *S. monacensis*-derived oligoprimers #7 and #8 resulted in a fragment of 1160 bp containing the MET14-CA gene. Three individual pools of PCR fragments were amplified. DNA fragments from each of these were inserted into the pUC18 vector giving rise to three individual clones pPF50, pPF51 and pPF52. The inserts in all three clones have been sequenced and compared in order to eliminate possible errors due to the PCR reaction. The three individual sequences was completely identical. The resulting MET14-CA sequence is shown in FIG. 4.

enzymes. This resulted in plasmid pPF55. The 3'-end piece of DNA was inserted as an XbaI-HindIII fragment of 761 bp into pPF55 digested with the same enzymes, giving rise to plasmid pPF56. The entire deletion allele of MET14-CA can be released from pPF56 using EcoRI and HindIII. The EcoRI-HindIII fragment from pPF56 was blunted and subcloned into pCH216 digested with EcoRV, resulting in plasmid pPF58 (FIG. 5b). pPF58 can be linearized by a partial digest with XmnI, which cuts once in the coding region of MET14-CA and once in the vector sequence, and thus be used for integration directed to the wild-type MET14-CA gene.

(viii) Use of the MET14-CA gene to inactivate the *S. carlsbergensis*-specific T14 alleles present in the allodiploid maters C80-CG65 and C80-CG110

To obtain a genetically completely defined brewer's yeast with no sulphite production, the *S. carlsbergensis*-specific MET14 alleles can be disrupted in a similar way as described above for the *S. cerevisiae*-like MET14 allele. The deletion allele of the *S. carlsbergensis*-specific MET14 gene on plasmid pPF58 (see above, FIG. 5) was used to disrupt the corresponding wild-type MET14-CA gene on the chromosome of the strains PFJ448 (C80-CG65 derivative) and PFJ467 (C80-CG110 derivative).

(ix) Evaluation of brewing performance and sulphite production of met14 mutants of *S. carlsbergensis* brewing yeast by fermentation at 50 L scale Methionine auxotrophic allotetraploid hybrids were constructed by hybridization of individual allodiploid met14 mutants of opposite mating types (see the Materials and methods section). Thus, a and α strains were crossed, e.g. PFJ459 was crossed with PFJ 530, resulting in strain PFJ501 and PFJ463 was crossed with PFJ530 to obtain strain PFJ514. A total of six met14 tetraploid strains were constructed, namely PFJ501, PFJ502, PFJ506, PFJ509,

TABLE 1.2.

Oligoprimers (SEQ ID NOS:1–12) used for amplification of fragments A–D in FIG. 2

| Oligoprimers | Sequence |
| --- | --- |
| #1: MET14-oli12 | 5'-GCTCTAGAGCATTGGAGTTGGTTATGCG-3' |
| #2: MET14-oli7 | 5'-GCGGATCCCCGACCAGAAGACGGTTGAAGAATGTGC-3' |
| #3: MET14-oli3 | 5'-GCGGATCCGCACATTCTTCAACCGTCTTCTGGTCGG-3' |
| #4: oligo #4 | 5'-GCTCTAGAATGGCTACTAATATTACT-3' |
| #5: MET14-oli6 | 5'-GCTCTAGAAGTAATATTAGTAGCCAT-3' |
| #6: MET14-oli7 | 5'-GCGGATCCTGTTCATGATTTCCGAAC-3' |
| #7: Mona-oli23 | 5'-GCGGATCCGGAGTCGGTACTAAATATC-3' |
| #8: Mona-oli20 | 5'-GCGGATCCGAAAGGTGGCCTATC-3' |
| #9: Mona-oli29 | 5'-GCGAATTCCCATCGCAAACTGGGG-3' |
| #10: Mona-oli30 | 5'-GCGGATCCGTCGAGAACATCTGCG-3' |
| #11: Mona-oli31 | 5'-GCTCTAGAGCTTGTGCACTGGAAC-3' |
| #12: Mona-oli32 | 5'-GCAAGCTTCTCTCATGGAATCCTG-3' |

(vii) Construction of a deletion allele of the *S. carlsbergensis* MET14 gene

A deletion allele of the *S. carlsbergensis*-specific MET14 gene was made by PCR, taking advantage of the sequence information obtained from sequencing of the MET14-CA gene. Two pieces of DNA was synthesized from the 3'- and 5'-ends of MET14-CA leaving a gap of 208 bp, covering the most down-stream part (position -85) of the promoter and the first part (position +124) of the open reading frame. The two pieces were ligated into pUC19 in two steps. The 5'-end fragment of the gene (348 bp) was inserted as an EcoRI-BamHI fragment into pUC19 digested with the same PFJ510 and PFJ514 (see Table 1.1). Fermentation of brewer's wort with strains PFJ501 and PFJ514 were performed at 50 L scale using the production strain M204 as a reference strain. All strains were tested in three successive fermentation generations. The production of sulphite and the attenuation were followed during the fermentation and after bottling, the beer was analyzed for aroma compounds.

Sulphite production was markedly reduced during fermentation compared to the reference strain, but not completely eliminated (data not shown). Though, after bottling no measurable sulphite was present in the beer from strain PFJ501 and PFJ514 compared to 8–13 ppm sulphite in beer from the reference strain (Table 1.3). The attenuation from PFJ501 and PFJ514 was slightly delayed compared to the reference strain, although the three strains reached approximately the same gravity level at the end of fermentation (FIG. 7). This occurred in spite of the fact that the cell number was usually somewhat lower for PFJ501 and PFJ514 as compared to M204 during fermentation (FIG. 8). The bottled beer was assessed by a trained taste panel before and after forced aging. Before aging, the non-sulphite beers were found to be comparable to the reference beer, but after forced aging (7 days at 37° C.) the non-sulphite beers were heavily oxidized, while the reference beer was still satisfactory. This correlates nicely with the t2n measurements of the low-sulphite beers before and after aging, where a 3–5 fold increase were seen compared to the reference beer (Table 1.3). Another significant difference between non-sulphite beer and the reference beer was that after bottling the acetaldehyde content of the non-sulphite beer was only about 50% relative to that of the reference beer (Table 1.3).

The reconstituted brewer's yeast strains PFJ501 and PFJ514 that were inactivated in all four copies of MET14 (by the combination of recombinant genetics and UV-mutagenesis) were tested at 50 L scale. The strains showed a final attenuation comparable to the reference strain M204, although the number of cells in suspension was a little lower during fermentation as compared to the reference. There are no serious faults with respect to technical abilities of the two strains. At bottling no sulphite was detectable in the beer, even though low amounts of sulphite were detectable during fermentation (1–3 ppm). This could be due to a leaky MET14-CA mutation or to reduction of thiosulphate (which might take place in wort (Thomas et al., 1992)).

The fresh beer from strain PFJ501 and PFJ514 was assessed as "satisfactory" or "not quite satisfactory". However, after forced aging (7 days at 37° C.) this beer was generally assessed as being "not satisfactory" due to heavy oxidation. This corresponds nicely with the found values of

TABLE 1.3.

Levels of acetaldehyde, sulphite and trans-2-nonenal in bottled beer from fermentation with non-sulphite yeasts in 50 L pilot scale. * trans-2-nonenal were measured (ppb) before and after forced aginq at 37° C. for 7 days

|  | M204 | | | PFJ501 | | | PFJ514 | | |
| --- | --- | --- | --- | --- | --- | --- | --- | --- | --- |
|  | 1.gen | 2.gen | 3.gen | 1.gen | 2.gen | 3.gen | 1.gen | 2.gen | 3.gen |
| Acetaldehyde, ppm | 4.01 | — | 2.04 | 1.75 | — | 1.05 | 1.09 | — | — |
| Sulfite, ppm | 13 | 11 | 8 | 0 | 0 | 0 | 0 | 0 | 0 |
| trans-2-nonenal, fresh beer* | 0.04 | — | 0.03 | 0.05 | — | 0.07 | 0.05 | — | 0.07 |
| trans-2-nonanal, aged* | 0.04 | — | 0.17 | 0.16 | — | 0.30 | 0.14 | — | 0.39 |

1.4. Discussion

By Southern analysis it was verified that S. carlsbergensis brewer's yeast contains two divergent alleles of the MET14 gene. This is in accordance with several earlier observations, as reviewed by Kielland-Brandt et al., 1995. These alleles are designated MET14-CE (S. cerevisiae-like) and MET14-CA (S. carlsbergensis-specific). The MET14-CE in allodiploid maters of brewing yeast was inactivated by replacing the wild-type alleles with inactive deletion alleles. The MET14-CA genes in the same strains were inactivated by selection for UV-induced mutants resistant to selenate. Although auxotrophic met14 mutants of tetraploid brewing yeast could be constructed by crossing of diploid met14 mutants, such strains were found to revert to prototrophy at a low frequency. Thus, it was decided to isolate MET14-CA in order to inactivate this gene by recombinant gene techniques. Furthermore, the inactivation of MET14 genes in this yeast revealed that it harbours two copies of each divergent allele. Several S. carlsbergensis-specific genes (see e.g. Hansen and Kielland-Brandt, 1994; Hansen et al., 1994) have been isolated by complementation with an S. carlsbergensis gene library (Casey, 1986), though we were not able to find MET14-CA by complementation in an S. cerevisiae met14 strain. Instead, the MET14-CA gene was amplified by PCR under low-stringency conditions, using oligoprimers based on the S. cerevisiae MET14 sequence and template DNA from S. monacensis. Three individual PCR fragments were isolated in order to minimize the impact of any errors in the nucleotide sequence introduced during PCR amplification. Utilizing the sequence information, an inactive deletion allele of MET14-CA was constructed.

t2n. Initially, the levels of t2n in PFJ501, PFJ514 and M204 were comparable, but after forced aging a dramatic increase in t2n content was seen in the non-sulphite beers. Another difference between PFJ501, PFJ514 and the reference strain is the acetaldehyde content in the bottled beers which was reduced by about 50% in the non-sulphite beers. This is presumably due to the absence of sulphite during fermentation, allowing for degradation of more acetaldehyde by the yeast.

A strategy for use of the low-sulphite producing strains for beer production would be mixing of two individual batches of beer, one produced using the low-sulphite yeast and the other using a high-sulphite producing yeast strain. A yeast strain with the latter characteristics have been constructed and described by Hansen and Kielland-Brandt (1996b). This strain of brewer's yeast was inactivated in all four copies of MET10 (encoding sulphite reductase) resulting in highly increased sulphite production (60–70 ppm). Under normal circumstances, the amount of sulphite produced is often not satisfactory and varying from brew to brew. This strategy would result in beer produced with a predetermined sulphite content, sufficient to stabilize the beer without the need for sulphite as an external additive. Due to the reduced production of taste active sulphur compounds ($H_2S$-derived in a wild-type), beer produced with the low-sulphite yeast will have a very weak sulphurprofile, and therefore be more "taste-neutral". This makes the low-sulphite yeast an appropriate starting point for construction of a yeast strain for production of a "basic beer", which in turn can be combined with different beer batches containing flavour compounds of interest.

EXAMPLE 2

Identification of the genes responsible for reduction of dimethylsulphoxide to dimethyl sulphide and construction of yeast strains inactivated in such genes

2.1. Summary of the experiment

Dimethylsulphide, DMS, is a sulphur compound of importance for the organoleptic properties of beer, especially some lager beers. Production of DMS during beer production occurs partly during wort production and partly during fermentation. Methionine sulphoxide reductases (EC 1.8.4.5 and 1.8.4.6) are enzymes responsible for reduction of oxidized cellular methionines. These enzymes have been suggested to be able to reduce dimethyl sulphoxide (DMSO) as well, with DMS as product.

A gene coding for an enzymatic activity leading to methionine sulphoxide (MetSO) reduction in Saccharomyces yeast has recently been identified.

It was confirmed that the *Saccharomyces cerevisiae* open reading frame YER042w indeed appears to encode an MetSO reductase, and the name MXR1 is proposed for the gene. An mxr1 disruption mutant does not have the ability to reduce DMSO to DMS but appears to have unchanged fitness under laboratory conditions. It is suggested that disruption of MXR1 in brewing yeasts would neutralize the contribution of the yeast to the DMS levels found in beer.

2.2. Materials and Methods

Strains of bacteria and yeast and microbiological methods

The following yeast strains were used: *S. cerevisiae* S288C (MATα mal gal2), M3750 (MATa SUC2 mal mel gal CUP1 ura3), M1997 (MATa SUC2 mal mel gal CUP1), JH465 (MATa SUC2 mal mel gal CUP1 ura3 YER042w::URA3), *S. carlsbergensis* M204 (Carlsberg production strain), *S. monacensis* CBS1503, C80-CG65 and C80-CG110 (spore segregants of Carlsberg production strain 244 (M204), Gjermansen and Sigsgaard, 1981).

*Escherichia coli* DH5α (Gibco BRL) was used for selection and propagation of plasmid DNA. SC (synthetic complete) and SD (synthetic dextrose) were prepared as described by Sherman (1991). MP medium was identical to SD medium, except that yeast nitrogen base without ammonium sulphate was used, and 2 g/L of proline was included to serve as nitrogen source. YPD medium contained 1% Difco Bacto yeast extract, 2% Difco Bacto peptone and 2% glucose. Sulphur-free B medium was prepared according to Cherest and Surdin-Kerjan (1992). Brewer's wort had a gravity of 14.5% Plato. Yeast was grown at room temperature, unless otherwise indicated. *S. cerevisiae* was transformed essentially according to Schiestl and Gietz (1989).

DNA manipulations

Plasmid DNA was prepared from *E. coli* according to Sambrook et al. (1989), or using Qiagen maxiprep columns (Qiagen Inc.). DNA manipulations were performed according to manufacturers of enzymes (Boehringer Mannheim, Promega or New England Biolabs). Polymerase chain reaction (PCR) was performed using Amplitaq polymerase (Perkin Elmer) and according to the manufacturer.

Fermentations for assaying DMS production

Yeast was inoculated from freshly grown plate cultures into 200 ml growth medium in 500 ml polypropylene Erlenmeyer flasks. Fermentation proceeded through a 10 day period at 30° C. (50 rpm shaking) in the flasks provided with fermentation locks containing water. Samples were taken through the side of the flasks with syringes into evacuated blood sampling tubes (Sigsgaard and Rasmussen, 1985). DMS was measured using gas liquid chromatography.

Southern analysis

Genomic yeast DNA was treated with restriction enzymes and separated on 1% agarose gels, transferred to Hybond-N membranes, covalently bound to the membranes by UV irradiation, and hybridized to $^{32}$P-labelled probes (random priming) at low stringency (50° C., wash in 1.033 SSC) essentially according to Sambrook et al. (1989). Signals were recorded in a Phosphor-Imager (Molecular Dynamics Inc.).

2.3. Results and Discussion (i) Sequence alignments

No DNA sequences with homology to microbial DMSO reductases (*Eschericia coli* and *Rhodobacter sphaeroides*) were found within the open reading frames of the complete genome of *S. cerevisiae*. However, when looking for a homologue to peptide methionine sulphoxide reductases (PMSR's) from mammals, plants and bacteria, *S. cerevisiae* ORF YER042w showed high homology, as visualized in FIG. 9, employing the Macaw program (Schuler et al., 1991). Obviously, there appears to be different families of PMSR's, but the yeast homologue is very similar to all the other chosen PMSR's (*E. coli, Bos taurus, Arabidopsis thaliana* and *Fragaria ananassa*) at the majority of its length. It was concluded that yeast ORF YER042w was a likely candidate for the gene for yeast PMSR, and the working hypothesis was that the same gene would be responsible for the enzymatic activity leading to reduction of DMSO to DMS during wort fermentation.

(ii) Disruption of ORF YER042w

It was decided to disrupt ORF YER042w in *S. cerevisiae* strain M3750. The one-step integration approach of Rothstein (1991) was employed to remove the middle part of YER042w and to insert a functional URA3 gene, thus deleting and disrupting the ORF at the same time. Oligonucleotide primers MSR1 (SEQ ID NO:13) (sequence 5'-GGTAAAGCTTGGCGAGTCGAGAAAGGAAATC-3', covering nucleotide position −703 to −683 relative to the start codon of ORF YER042w and containing at the 5'-end 4 arbitrary nucleotides [to allow recognition enzyme cleavage] followed by an HindIII restriction site) and MSR2 (SEQ ID NO:14) (sequence 5'-GGTATCTAGAA TCGATGGTTTTTGAAATAAGCGACGAC-3', covering nucleotide positions +3 to +24 and containing at the 5'-end 4 arbitrary nucleotides followed by an XbaI restriction site and a ClaI site) were used to PCR amplify a 753 bp DNA fragment of ORF YER042w using *S. cerevisiae* S288C genomic DNA as template for the reaction.

Oligonucleotide primers MSR3 (SEQ ID NO:15) (sequence 5'-GGTAGGATCCCATTATCTGAGAGAAATGTAG-3', covering nucleotide positions +535 to +555 and containing at the 5'-end 4 arbitrary nucleotides followed by a BamHI site) and MSR4 (SEQ ID NO:16) (sequence 5'-GGTAGAATTCGTCGCCTGGTTAAAGGCTAAC-3', covering nucleotide positions +1233 to +1253 and containing at the 5'-end 4 arbitrary nucleotides followed by an EcoRI restriction site) were used to PCR amplify a 739 bp DNA fragment. The 739 bp DNA fragment was restriction digested with BamHI and EcoRI and the cut DNA purified on an agarose gel. During this process it was discovered that a previously overlooked EcoRI restriction site was present at position +1014 to +1019. This had the effect that the size of the digested DNA fragment was decreased to 489 bp.

This fragment was ligated into a pUC18 vector (Yanisch-Perron et al., 1985) that had been digested with BamHI and EcoRI and purified on an agarose gel, thus creating pJH118. The 753 bp DNA fragment was digested with HindIII and XbaI and ligated into pJH118 digested with the same enzymes, thus creating pJHll9. The *S. cerevisiae* URA3 gene from plasmid YEp24 (Bot-stein et al., 1979) was cut out with BamHI and ClaI, and ligated into the BamHI and ClaI restriction sites present between the two YER042w fragments in pJH119, thus creating pJH121.

The URA3-containing disruption cassette was cut out with PvuII and purified on an agarose gel. *S. cerevisiae* strain M3750 was grown in 50 ml YPD medium to early exponential phase ($OD_{600}$=1.0), and transformed with 10 µg purified disruption cassette DNA. The transformation mixture was spread onto SC-ura plates and allowed to grow for 5 days. Several hundreds uracil-prototrophic colonies were obtained, of which ten were pure-cultivated. Genomic DNA was prepared from these clones, and analytical PCR employing oligonucleotide primers MSR1 and MSR4 was performed. A DNA band of about 3.0 kb size was seen from all transformants and a band of about 2.0 kb from strain M3750. These sizes were those expected for disruptants and wild-type yeast, respectively. One disruptant, designated JH465, was chosen for further experiments. The disruption strategy and analytical PCR of strain JH465 aepicted in FIG. 10.

A sample of strain JH465 was deposited on Jul. 8, 1998 in accordance with the Budapest Treaty with the American Type Culture Collection (ATCC) under the Accession No. 74452.

(iii) Phenotype of disruption mutant

EthSO resistance

Ethionine sulphoxide (EthSO) is a putative analogue of MetSO. Strains M1997 and JH465 were both applied in water suspension onto an SC or an SC-met (SC medium without methionine) plate containing a pre-formed ethioninesulphoxide-gradient (FIG. 11). After four days of growth at 30° C. a clear inhibition zone of about 22 mm proximal to the filter strip was observed with strain M1997, an inhibition which was not seen when methionine was present in the medium (SC). Strain JH465, on the other hand, was clearly more resistant to EthSO on SC-met; very good growth was found up to 17 mm from the filter strip, and some growth was visible up to 5 mm from the strip. Under the conditions chosen, the enzymatic product of ORF YER042w probably converts EthSO into ethionine, a methionine analogue that is toxic to most organisms, including Saccharomyces yeast (Singer et al., 1978).

The same experiment was performed on MP plates (minimal medium containing proline as the only nitrogen source). Here, EthSO seemed more toxic to strain JH465, indicating that an alternative system for reduction of EthSO is induced under these conditions (data not shown).

(iv) Strain fitness

Strains M1997 and JH465 were grown from an $OD_{600}$ of 0.15 in YPD or SD media and followed by $OD_{600}$ until early stationary phase. There was no difference between the growth abilities of the two strains in either media (FIG. 12). The same strains were streaked onto solidified YPG (rich medium containing glycerol as carbon source, and NF media (minimal medium containing glycerol as only carbon source). There was no apparent difference in colony size after 1 week of growth at 30° C. on YPG, while on NF there seemed to be a slight decrease in colony size of strain JH465. It was concluded that the putative peptide methionine sulphoxide reductase encoded by ORF YER042w is not vital for growth under laboratory conditions.

(v) Growth with MeSO as sulphur source

Strains M1997 (wild-type) and JH465 were both applied as 20 µl of water suspension onto a plate with sulphur-free synthetic medium (B) containing at its center a filter disk with 200 µl 0.1 M methioninesulphoxide (MetSO). After three days incubation at 30° C. both strains could be seen to grow equally well on the inner part of the MetSO gradient. The experiment was repeated using liquid B medium that contains no sulphur source. M1997 and JH465 were grown for 12 hours with 0.02 mM L-methionine, washed in water and starved for 12 hours in B medium without any sulphur source at a dilution to $OD_{600}$ =0.01. During this period, the $OD_{600}$ increased to 0.13, most probably due to the endogenous glutathione stock (Elskens et al., 1991). At that point each culture was divided into three aliquots. To the first aliquot was added 5 µM L-methionine, to a second aliquot 5 µM L-methioninesulphoxide and to the third nothing was added, and $OD_{600}$ was followed for 9 hours. During this period the density of the wild-type culture with methionine as sulphur source increased by a factor 3.1, while the culture of the same strain with MetSO increased by a factor 3.4. The same factors for strain JH465 were 2.9 and 2.6, respectively. The experiment was repeated with basically the same results.

While it is quite difficult to explain why MetSO should be a better sulphur source than methionine, it is also clear that it is of some advantage for the yeast to have an active ORF YER042w, when it comes to utilization of methionine sulphoxide. The fact that strain JH465 do grow quite well on MetSO both on solid and in liquid media indicates that ORF YER042w is not the sole enzymatic activity capable of converting MetSO into methionine. These data and the fact that EthSO is still slightly toxic for JH465 (see above) could be explained if one assumes the existence of a low-affinity system for reduction of both compounds, and that this system has not been affected by the inactivation of ORF YER042w. This is in accordance with the results of Moskovitz et al. (1997), who showed that a yeast strain disrupted in the same gene had lost only 33% of its reductase activity against free MetSO. Possibly, this system could be the one that seems to be active in EthSO reduction under nitrogen-limited conditions (MP medium, see above) which should then have a very low background activity under nitrogen-abundant conditions.

(vi) Production of DMS from DMSO by strain JH465

The strains M1997 and JH465 were inoculated in liquid SD or MP medium containing 0, 1.0, 10 or 100 mg/L DMSO or in auto-claved or fresh wort. Inoculation was performed in 200 ml medium in 500 ml polypropylene Erlenmeyer flasks fitted with fermentation locks and left to grow for 1 week at 30° C. 10 ml samples were taken and the DMS content was measured. As can be seen from FIG. 13, quite significant amounts of DMS were formed in the fermentations with strain M1997 when DMSO had been added although only about 0.8% of the substrate was converted on a molarity basis. The same pattern could be seen using MP medium, but here about 1.4% was converted. The rather low conversion ratio of DMSO to DMS by this enzyme (4% in SD and 14% in MP medium) is in agreement with earlier observations (Anness, 1980; Anness and Bamforth, 1982). No conversion at all was performed by strain JH465, except for 0.001% in MP medium with 100 ppm DMSO. The last observation supports the notion that an alternative system that can reduce compounds as MeSO, EtSO and DMSO does get active under certain nitrogen-limiting conditions. However, this putative system can certainly not explain the rise in DMSO reduction by the wild-type yeast, when going from SD to MP medium (almost a doubling in the conversion ratio). This effect is rather an induction of the system encoded by ORF YER042w itself.

Brewer's wort assumingly having a natural content of DMSO, either autoclaved or fresh from production, was also inoculated with these strains, and the mixture allowed to grow under the same conditions as described above. A significant amount (0.02 ppm) of DMS was formed by strain M1997 from autoclaved wort while no DMS resulted from fermentation with the mutant strain in this medium. When using fresh wort, 0.169 ppm DMS was formed from the wild-type yeast and only 5.3% less by the mutant yeast. The increased level of DMS probably reflects the endogenous level of DMS present in brewer's wort. It should be noted that *S. cerevisiae* does not ferment brewer's wort very well, and consequently that these data do not reflect the situation in beer production.

It was concluded that yeast ORF YER042w is responsible for the enzymatic activity leading to DMS formation from DMSO. As it was furthermore verified that YER042w is responsible for at least part of the capability of *S. cerevisiae* to reduce methionine sulphoxide, the name MXR1 (peptide Methionine sulphoXide Reductase 1) is suggested for this gene.

(vii) Occurrence of a gene sequence homologous to *S. cerevisiae* ORF YER042w in a production strain of *S. carlsbergensis*

To verify the theory that a gene, or set of genes, in *S. carlsbergensis* brewing yeast corresponding to MXR1 is responsible for DMSO reduction during wort fermentation, the content of such sequences in this yeast was analyzed. Southern analysis at low stringency of digested genomic DNA from *S. carlsbergensis*, *S. monacensis*, *S. cerevisiae* and of two spore-clones of an *S. carlsbergensis* brewing yeast is shown in FIG. 14. The DNA, cut with BglII was hybridized with an *S. cerevisiae* MXR1 probe at low stringency to possibly allow the detection or nomoeologous genes present in the brewing yeast.

A lower band of 2.7 kb was observed in all strains except from *S. monacensis*, while an upper band of about 4.0 kb was observed in all strains except *S. cerevisiae*. An even higher molecular weight (and somewhat fainter) band was observed for all strains except *S. monacensis* and may represent a partial digestion of the MXR1 region. As 2.7 kb is the expected size for an MXR1-containing BglII-fragment (FIG. 10), and as the 2.7 kb bands were also present on high-stringency Southern hybridizations using the same filter (data not shown), these bands supposedly represents MXR1 (*S. cerevisiae*) or a gene basically identical to this, MXR1-CE (*S. cerevisiae*-like MXR1) (M204, C80-CG65 and C80-CG110). The bands of 4.0 kb were not seen in high-stringency Southern hybridizations (data not shown) and these bands probably represent a gene somewhat diverged from but functionally analogous to MXR1. This putative gene (present in *Saccharomyces monacensis* CBS1503, *S. carlsbergensis* M204, C80-CG65 and C80-CG110) was designated MXR1-CA (the *S. carlsbergensis*-specific MXR1 gene). *S. carlsbergensis* is a species hybrid containing a genome which is originally derived from two Saccharomyces species and two homoeologous alleles of a given gene is usually found in this hybrid organism (for a comprehensive description of the genetics of *S. carlsbergensis* brewing yeast see Kielland-Brandt et al., 1995). The results presented here is in perfect concord with this.

(viii) Conclusion

To conclude, it is suggested that *S. carlsbergensis* brewing yeast has two homoeologous genes for DMSO reduction, MXR1-CE and MXR1-CA, and that these two genes are responsible for the activities reducing DMSO to DMS during primary fermentation of brewer's wort.

To summarize, it was discovered that *S. cerevisiae* ORF YER-042w is responsible for the enzymatic activity that reduces DMSO to DMS, at least under nitrogen-rich conditions. There may, however, be another system able to fulfil the same task under certain nitrogen-limiting conditions. As the native function of ORF YER042w supposedly is reduction of peptide methionine sulfoxides, the name MXR1 (peptide Methionine sulphoXide Reductase) is suggested for this gene. The *S. carlsbergensis* brewing yeast appears to contain a gene almost identical to MXR1, MXR1-CE and in addition an analogous but diverged gene, MXR1-CA. As a *S. cerevisiae* strain without MXR1 activity does not seem to loose viability or vitality under laboratory conditions, it is contemplated that the inactivation of these genes in the brewing yeast is a suitable means of decreasing the amount of DMS formed during primary beer fermentation.

EXAMPLE 3

Construction of mutants of brewer's yeast with altered production of hydrogen sulphide: In vivo evidence for a direct link between formation of $H_2S$ and certain thiols and thioesters 3.1. Summary of the experiment Hydrogen sulphide is a brewing yeast-derived sulphur compound of great importance for the taste and flavour of beer. While it provides some of the character of very young beer and may be desired in low amounts to mask the impression of certain other flavour components, it is in general undesired at higher concentrations in beer. Furthermore, certain other taste-active sulphur components, like thiols and thioesters, may be derived from hydrogen sulphide. Here it is shown that it is possible, by classical breeding methods, to construct well-performing brewing yeasts with an altered production of hydrogen sulphide. Furthermore, evidence was found for a direct metabolic link between formation of hydrogen sulphide and of ethanethiol, methylthioester and ethylthioester.

3.2. Materials and methods

Strains of yeast and microbiological methods

The following yeast strains were used in the experiments: M204 (Carlsberg production strain), C80-CG65 (Mat a) and C80-CG110 (MAT α) (spore segregants of strain 244 (M204), see Gjermansen and Sigsgaard, 1981). JH 441, JH442, JH443, JH444, JH506, JH515, JH516, JH517 are all described in this study. SC (synthetic complete) and SD (synthetic dextrose) were prepared as described by Sherman (1991). MP medium is identical to SD medium, except that yeast nitrogen base without ammonium sulphate was used, and 2 g/L of proline was included to serve as nitrogen source. YPD medium contained 1% Difco Bacto yeast extract, 2% Difco Bacto peptone and 2% glucose. YP-galactose medium is identical to YPD medium, except that glucose has been substituted with galactose as carbon source. BIG-YNB medium was prepared according to Rikkerink et al. (1988) as modified by Thomas et al. (1992), and is basically a synthetic complete medium containing sodium sulphite and ammonium bismuth citrate. Brewer's wort had a gravity of 14.5% Plato. Yeast was grown at room temperature, unless otherwise indicated.

Mutagenesis

UV mutagenesis was performed by irradiating Petri dishes (YPD) containing spread yeast cultures. The time necessary to ensure 50% killing was determined empirically and found to be about 6 seconds for strain C80-CG110. Equipment used for UV irradiation was two Philips TUV 15W, G15T8 tubes in a steel cabinet placed about 20 cm above the Petri dishes irradiated. After irradiation, the plates were kept in the dark for 24 h.

Mating of yeast and screening for mating products

S. carlsbergensis spore segregants of different mating type were mated by overnight co-inoculation on the surface of a YPD plate at 20° C., basically according to Gjermansen and Sigsgaard (1981). Mating products were enriched for by inoculating a tiny amount of the cell mix into liquid rich medium containing as the carbon source galactose (Hansen and Kielland-Brandt, 1996b). After 6 days of growth at 20° C. some of the culture was streaked out to single colonies on solidified rich medium containing galactose as carbon source. Large and fast-forming colonies were picked and streaked in replicapattern onto YPD plates. After 4 days of growth these plates were replica-plated to sporulation medium and the plates left at 20° C. for 8 days. The plates were then illuminated with UV light of 302 nm (Briza et al., 1986), and emission of visible light were taken as evidence for spore formation and such clones were assumed to be mating products.

Random spore isolation

Brewing yeast was sporulated by streaking in a thin layer on solid sporulation medium and the plates incubated at 20° C. for 6 to 14 days as necessary for spore formation. Spore formation in the culture was detected by malachite green staining (Schaeffer and Fulton, 1933; Gjermansen and Sigsgaard, 1981) and the culture enriched for ascospores and these isolated according to Gjermansen and Sigsgaard (1981). Spore clones were identified by the lack of ability to emit visible light after growth on sporulation medium and illumination with UV light of 302 nm. Spore clones of mating type a was identified by replica plating streaks or colonies of the spores in question onto a YPD plate containing a growing "lawn" of strain C80-CG110 (Mat α). After 24 h growth at 20° C. this plate was further replica-plated onto sporulation medium and after one week of growth sporulation (as visualized with UV light) identified the involved spore-clone as one of mating type a.

Fermentation experiments

Yeast strains were propagated in brewer's wort at 13° C. by successive inoculations of larger and larger volumes of sterile brewer's wort: Ten ml were inoculated with $10^6$ yeast cells; after 7 days this culture was diluted with 300 ml wort which after yet 7 days were poured into 8 litres of wort. After fermentation for 12 days (with occasional stirring), the cultures were cooled to 7° C. and the yeast was allowed to settle for two days. Fourteen grams of wet yeast was then added to 2 litres of aerated brewer's wort in an EBC tube (EBC-Analytica Microbiologica, 1977). The temperature during the first 7 days of the fermentation was 13° C. after which it was lowered to 7° C. and kept there for the last 24 h to allow the yeast to settle to the bottom of the tubes. Samples were taken anaerobically each day through silicone membranes. Fermentation and sampling were performed automatically in the Multiferm system as described by Sigsgaard and Rasmussen (1985). All experiments were performed in duplo.

Chemical and other analyses

Yeast cell counts were performed using a Coulter Counter model ZB. Residual sugar extract of the beer was determined using gradient tubes (Atkin et al., 1947). Higher alcohols, esters, acetaldehyde, diacetyl, pentanedione and dimethylsulphide were measured using gas liquid chromatography. $SO_2$, methylthioacetate, ethanethiol and ethylthioacetate were measured in a Purge-and-Trap system using a chemiluminescence sulphur detector.

3.3. Results and Discussion (i) Construction of mutants of tetraploid brewing yeast with decreased production of hydrogen sulphide The level of not only methionine but also threonine in brewer's wort may influence the sulphur metabolism of the brewing yeast. Ramos-Jeunehomme et al. (1979) showed that threonine is taken up by the yeast rather much before methionine. That could possibly explain the high production of hydrogen sulphide often seen in the early period of the main fermentation (Nagami et al., 1980; Takahashi et al., 1980); threonine exerts feed-back control on its own formation at the point of conversion of aspartate (see FIG. 15). This means that a high threonine concentration will inhibit formation of O-acetylhomoserine, the binding partner for hydrogen sulphide. If at the same time, only diminutive amounts of methionine is present in the cell there will be a high formation of hydrogen sulphide. Only after the threonine has been used for further metabolism will the yeast cell be able to utilize the hydrogen sulphide surplus. It has been shown that yeast mutants that are resistant to hydroxynorvaline, a toxic threonine analogue, has an aspartokinase (EC 2.7.2.4) that is insensitive to threonine feed-back inhibition (Ramos and Calderon, 1992). O-acetyl homoserine formation in such mutants is consequently no longer controlled by the level of threonine.

As these mutations are dominant, it was decided to employ this as a strategy to make mutants of brewing yeast that would produce less than normal hydrogen sulphide. The brewing yeast was found to be quite insensitive towards hydroxynorvaline. In media containing ammonia ions hydroxynorvaline up to 100 mM was not toxic. However, in MP medium, where the only nitrogen source is proline, 100 mM hydroxynorvaline was toxic. Strain M204 was grown in MP medium to stationary phase at 20° C. and 50 μl of this culture added to 10 ml liquid MP medium containing 100 mM hydroxynorvaline. After one week of growth at slow shaking, only a very week growth could be seen. 50 μl of this culture was reinoculated in yet 10 ml MP with hydroxynorvaline and growth was continued for one more week. After this week significant growth could be seen and after one more inoculation the culture was dense after 48 hours. Cells from this culture were spread onto solid YPD medium, and single clones were assayed for hydrogen sulphide production by applying droplets of yeast in water suspension onto BIG-YNB plates. Hydrogen sulphide has the property of easily forming an insoluble brown sulphide with the bismuth in the BIG-YNB plates (Rikkerink et al., 1988; Thomas et al., 1992). The developed colour was observed after 8 days of growth. The outcome of this experiments was the mutant strains JH439 through JH452 and JH489 through JH505. The ability of these strains to tolerate increased concentrations of hydroxynorvaline was confirmed by re-inoculation of each strain, along with strain M204, into the medium used for the selection. The slightly lower hydrogen sulphide production on BIG-YNB plates of a selected range of these strains can be seen in FIG. 16.

A sample of S. carlsbergensis strain JH441 was deposited on Jul. 8, 1998 in accordance with the Budapest Treaty with the American Type Culture Collection (ATCC) under the Accession No. 74451.

(ii) Selection of allodiploid maters of S. carlsbergensis brewer's yeast with enhanced production of hydrogen sulphide The BIG-YNB plate assay for hydrogen sulphide production was employed directly in a screen for S. carlsbergensis mutants producing increased amounts of hydrogen sulphide. An exponentially growing culture of the allodiploid S. carlsbergensis strain C80-CG110 was diluted and spread onto BIG-YNB plates in a concentration suitable for obtaining about 1,600 colonies per plate. The yeast cells on 50 such plates were mutagenized using UV irradiation for a time period sufficient to ensure about 50% killing. Thus, it was expected to obtain about 800 surviving colonies on each plate. The plates were wrapped in aluminium foil and the yeast left to grow and develop colour for 8 days at 20° C. After the 8 days, 4 colonies had developed a brown colour significantly darker than the rest of the colonies. Yeast from these colonies were pure-cultivated by re-streaking on YPD medium. The four mutant yeast strains were designated JH341, JH342, JH343 and JH344.

(iii) Construction of allodiploid maters of mating type a containing the same genetic trait enhancing hydrogen sulphide production A similar approach was followed in an attempt to isolate the same type of mutants of the strain C80-CG65, an allodiploid S. carlsbergensis yeast of mating type a. However, no mutants were found. As an alternative strategy it was decided to transfer the mutations to yeasts with the opposite mating type by mating of the four original mutants with C80-CG65, followed by random spore isolation and screening for colonies of mating type a with dark brown colour on BIG-YNB medium. Each of the four mutants were mated with C80-CG65 and mating products were selected as described in the Materials and Methods section. The four yeast strains that resulted were designated JH477, JH478, JH479 and JH480, respectively.

To confirm the tetraploid nature and ability to sporulate of these strains they were streaked onto sporulation medium. After incubation for 8 days at 20° C. dityrosin formation, showing up as fluorescence when exciting the cells with UV light of 302 nm (Briza et al., 1986), was taken as evidence for spore formation. After sporulation for ten days on solid sporulation medium at 20° C., followed by random spore isolation, the petri dishes containing the spores were replicaplated onto BIG-YNB plates and the yeast strains were allowed to grow and develop colour for 7 days. Dark brown colonies were pure-cultivated and lack of dityrosine formation on sporulation medium along with ability to mate with strain C80-CG110 were taken as evidence that these strains were allodiploid and of mating type a.

Eleven of such strains derived from JH477 and containing the genetic trait from strain JH341 were designated JH481, JH482, JH483, JH484, JH485, JH486, JH487, JH518, JH519, JH520 and JH521, respectively. Four strains derived from JH579 and containing the genetic trait from strain JH343 were named JH522, JH523, JH524 and JH525, respectively. One strain, derived from JH580 and containing the genetic trait from strain JH344 was designated JH488.

(iv) Reconstitution of brewing yeast with enhanced hydrogen sulphide production

To construct tetraploid brewing yeast with enhanced hydrogen sulphide production the following crosses were made: JH341 were crossed with JH482, JH483, JH484, JH486, JHS18, JH519, JH520 and JH521 and hybrids selected for good growth on YP-galactose plates. The expected sporulation-proficient nature of these strains was confirmed as dityrosine formation on sporulation medium was evident. The strains were designated JH506 through JH517 and JH526 through JH540. JH343 were crossed with JH522, JH523, JH524 and JH525 and after confirmation of the tetraploid nature of these strains, they were named JH541 through JH560. The high-H$_2$S production phenotype of the tetraploid yeast strains was confirmed by applying droplets of aqueous suspensions of the different strains onto BIG-YNB medium and allowing growth for 4 days. FIG. 17 depicts the strategy for the making of these mutants and FIG. 18 illustrates hydrogen sulphide production of a selected range of these strains.

A sample of S. carlsbergensis strain JH506 was deposited on Jul. 8, 1998 in accordance with the Budapest Treaty with the American Type Culture Collection (ATCC) under the Accession No. 74453.

(v) Evaluation of strains with altered hydrogen sulphide production in Multiferm: Fermentation and sulphur profile To assess the fermentation capabilities and production of sulphur compounds by brewing yeast strains having altered production of hydrogen sulphide a range of these yeast strains was tested in trial fermentation in 2 L EBC fermentation tubes in Multiferm (Sigsgaard and Rasmussen, 1985). The outcome of these experiments are summarized in Table 3.1. An enhanced formation of 2-methyl-1-propanol is seen with the strains JH 441-JH444 while ethylacetate and acetaldehyde formation is especially increased with strain JH442. Apart from that the strains with decreased hydrogen sulphide formation appeared to perform quite normally during fermentation: levels of SO$_2$ and residual sugar in the beer were quite normal and yeast harvest and the amount of dead cells gave satisfactory values. The high formation of ethylacetate and acetaldehyde in strain JH442 suggests that the mutation or mutations present in this strain differ(s) somewhat from the other strains.

TABLE 3.1.

Fermentation characteristics of strains of brewing yeast with enhanced or decreased production of hydrogen sulphide

| Strain | 1-Pro | 1-But | 2M1p | 3M1b | 3Mba | Ibac | Etac | Acal | Da | Pd | DMS | SO$_2$ | Ext | DC | YH |
|---|---|---|---|---|---|---|---|---|---|---|---|---|---|---|---|
| M204 (I) | 19.1 | 1.3 | 16.4 | 102 | 3.5 | 0.11 | 31.5 | 4.8 | 0.27 | 0.15 | 0.06 | 8.5 | 2.7 | 9.5 | 20.2 |
| JH441 | 21.3 | 1.3 | 21.9 | 112 | 3.9 | 0.15 | 34 | 3.8 | 0.24 | 0.17 | 0.06 | 4.9 | 2.8 | 10.5 | 17.8 |
| JH442 | 23.9 | 2 | 21.5 | 101.5 | 4.9 | 0.2 | 48.2 | 7.1 | 0.25 | 0.19 | 0.08 | 8.2 | 2.8 | 9 | 21.3 |
| JH443 | 21.1 | 1.3 | 19.6 | 113.9 | 4.3 | 0.15 | 36.7 | 4.6 | 0.29 | 0.19 | 0.06 | 6 | 2.7 | 10 | 18.2 |
| JH444 | 20.4 | 1.2 | 19.0 | 104 | 4 | 0.14 | 35.3 | 4.7 | 0.3 | 0.2 | 0.06 | 5.8 | 2.7 | 10.5 | 18.5 |
| M204 (II) | 14.8 | 1 | 16.1 | 93.6 | 4.7 | 0.15 | 34.3 | 4.7 | 0.17 | 0.1 | 0.05 | 8.5 | 2.8 | 13.3 | 19 |
| JH506 | 15.9 | 0.9 | 27.2 | 101.1 | 3.0 | 0.18 | 26.4 | 6.8 | 0.06 | 0.05 | 0.07 | 14.2 | 2.9 | 16.7 | 19.1 |
| JH515 | 17.1 | 1.4 | 23.8 | 91.8 | 2.6 | 0.15 | 23.7 | 8.6 | 0.07 | 0.09 | 0.07 | 12.8 | 2.8 | 17.5 | 21.5 |
| JH516 | 16.7 | 1.2 | 24.4 | 92.2 | 2.5 | 0.15 | 23.3 | 7 | 0.07 | 0.08 | 0.07 | 12.8 | 2.8 | 15.8 | 22.1 |
| JH517 | 16.9 | 1.4 | 23.2 | 89.6 | 2.3 | 0.13 | 21.7 | 6 | 0.07 | 0.09 | 0.07 | 13 | 2.8 | 18.3 | 23.6 |

Abbreviations: 1-Pro: 1-Propanol; 1-But: 1-Butanol; 2M1p: 2-Methyl-l-propanol; 3M1b: 3-Methyl-1-butanol; 3Mba: 3-Methyl-butyl-acetate (isoamylacetate); Ibac: Isobutylacetate; Etac: Ethylacetate; Acal: Acetaldehyde; Da: Diacetyl; Pd: Pentadione; DMS: Dimethylsulphide; SO2: Sulphur dioxide; Ext: Residual sugar in the beer; DC: Dead cells at the end of fermentation; YH: Yeast harvest at the end of fermentation; Numbers are in mg/L except for Ext (%)

and DC (X×10⁹ cells/L). M204 (I) refers to the reference strains tested together with strains JH506 and JH515-JH517.

As for the strains with enhanced hydrogen sulphide production (JH506, JH515, JH516 and JH517) also these strains appeared to behave quite normally in fermentation. Also these strains had an enhanced production of 2-methyl-1-propanol and also the level of acetaldehyde was generally increased. In contrast, a decreased formation of ethylacetate was observed and very low values for the vicinal diketones (diacetyl and pentanedione). A striking feature of these strains is a significantly enhanced sulphite production ($SO_2$): 50 to 67%). This, however, is not unexpected, as sulphite is the precursor for hydrogen sulphide.

The beer from these fermentation trials were also assayed for formation of MeSAc and EtSAc. FIG. 19 depicts some of the results of these analyses. The strains having enhanced formation of hydrogen sulphide (JH506 and JH515-JH517) also showed a significantly increased formation of MeSAc as well as of EtSAc, while the strains with decreased hydrogen sulphide production (JH 441-JH444) had a decreased MeSAc production. This is evidence for a direct link between formation of hydrogen sulphide and the thioesters methyl- and ethylthioacetate.

(vi) Further evidence from fermentation at 50 L scale with met2Δ, met10Δ and met14 strains: sulphur profile and taste evaluation To further confirm the metabolic coupling between hydrogen sulphide and the thioesters MeSAc and EtSAc, the formation of these compounds and EtSH in strains of brewing yeast with well-described genetic alterations leading to elimination or a large increase of hydrogen sulphide production (Hansen and Kielland-Brandt, 1996a; 1996b) was investigated. In one of these strains all copies of the two types of the MET2 genes are inactivated. This has the effect that very high amounts of hydrogen sulphide are accumulated and secreted to the growth medium. The other strain has no MET10 activity. As MET10 encodes part of the sulphite reductase enzyme (Hansen and Kielland-Brandt, 1994), this strain cannot produce hydrogen sulphide at all. Beer from 50 L fermentation trials (Hansen and Kielland-Brandt, 1996a; 1996b) were subjected to analysis for the above mentioned thiols and thioesters. The results are depicted in FIG. 20. Clearly, a high hydrogen sulphide production is associated with an increase in the production of all the three sulphur compound whereas, when no hydrogen sulphide is produced, almost no production of these compounds takes place.

Thus, we have provided the first biological evidence, based on genetic alterations of brewing yeast directed towards up- or down-regulation of hydrogen sulphide production, of a direct metabolic link between formation of certain thiols and thioesters and the formation of hydrogen sulphide.

(vii) Conclusions

Using classical mutagenesis and cross-breeding mutant strains of S. carlsbergensis brewing yeast were constructed which had decreased or enhanced production of hydrogen sulphide. These yeast strains were subjected to trial fermentations and turned out to perform satisfactory in most respects. Analysis of sulphur components of the resulting beer showed that the yeast strains having decreased production of hydrogen sulphide also had a reduced production of methylthioacetate whereas the yeast strains with increased hydrogen sulphide production also showed increased formation of methyl- and ethylthioacetate. This is genuine biological evidence for a metabolic link between hydrogen sulphide and certain thioesters. Using brewing yeast strains with defined mutations resulting in either zero or extremely high hydrogen sulphide production, this relationship could be confirmed. These experiments furthermore showed that also formation of ethanethiol is hydrogen sulphide dependent.

To summarize, it has been demonstrated that it is possible to provide strains of brewing yeast by classical breeding methods having altered production of hydrogen sulphide and in this way change the production of certain thiols and thioesters that are important for the organoleptic character of beer.

EXAMPLE 4

Construction of Saccharomyces cerevisiae and Saccharomvces carlsbergensis strains having reduced or no production of higher alcohols and acetate esters The purpose of this experiment was to construct brewer's yeast mutants with lowered production of isoamyl alcohol and isoamyl acetate and to obtain finished beer produced by such mutants which has a reduced level of higher alcohols and their corresponding acetate esters or which does not contain such compounds. The following approaches were used for introducing modifications at two points in the pathway leading to higher alcohols and their corresponding acetates:

(a) Inactivation/modification of the isopropylmalate synthases in the leucine de novo synthesis pathway (encoded by LEU4, ORF YOR108w and THI3 (=ORF YDL080c) (This Example);

(b) Removal of the alcohol acetyl transferase activities encoded by ATF1-CE, ATF1-CA and ATF2 genes (Example 5).

Total removal of isopropylmalate synthase activity might not be desirable since the Leu3p-isopropylmalate complex is needed for positive regulation of at least the following genes: LEU1, LEU2, LEU4, ILV2 and GDH1 (Friden and Schimmel 1988, Hu et al. 1995).

4.1. Experimental (i) Materials and methods

In Tables 4.1 and 4.2 are shown the genotypes of relevant S. cerevisiae and S. carlsbergensis strains used in this study. Agar plates with synthetic complete medium (SC), rich high glucose media plates (PS) and defined minimal media plates synthetic complete (SC) and derivatives (SC without methionine (SC-methionine), SC without leucine (SC-leucine) for selection and genetic studies were made up according to Sherman, Fink and Hicks (1979). Selection for LEU4$^{fbr}$ clones was done on SC-leucine with the addition of 1 or 5 mM 5,5,5-triflouro-DL-leucine (SC-leucine+TFL). 5,5,5-triflouro-DL-leucine No. 12890 was obtained from Lancaster Synthesis Ltd.

Separation of chromosomal length DNA molecules was done in a BIO-RAD CHEF-MAPPER system. Chromosomal DNA was purified in FMC Incert agarose according to Schwartz and Cantor (1984) with the modification by Pedersen (1988) and chromosomal length DNA molecules were separated in FMC FastLane agarose. DNA sequences used for restriction maps and PCR amplifications were obtained from Saccharomyces Genome Database (http://genome-www.stanford.edu/Saccharomyces/).

E. coli strain XL1-blue (#200236) for transformation was obtained from STRATAGENE and newly synthesised PCR fragments and DNA fragments and plasmids were purified using a BIO-RAD Prep A Gene DNA Purification Kit 732-6010. Yeast transformations were done with the lithium acetate method according Schiestl and Gietz (1989) and Gietz et al. (1992).

The *S. carlsbergensis* specific MET2 allele is designated herein as MET2-CA (Hansen and Kielland-Brandt, 1994). The pUC19 vector containing the 3.7-kb HindIII MET2-CA insert is designated pMBP96A2. The 3.7 kb HindIII MET14-CA-containing fragment was subcloned from the plasmid p19-6 (Hansen and Kielland-Brandt, 1994). The plasmid pMBP96A2 was used for cloning of MET2-CA or as basis for the YOR108w disruption plasmid.

Construction of strains carrying inactive forms of LEU4 was done by the two-step deletion procedure by Scherer and Davis (1979) (loop-in/loop-out method). Inactivation of YOR108W was done by insertion of a plasmid with selected YOR108W sequences and the 3.7-kb HindIII MET2-CA fragment as selective marker.

Transformants containing the LEU4 deletion plasmid and the YOR108W were isolated on selective SC-methionine plates. Southern transfer of agarose gels were done onto Schleicher & Schuell BA85 0,45 mm Ref.-No. 401196. Probes were labelled and detected with the DIG DNA Labelling and Detection Kit (Boehringer Mannheim 1 093 657). Restriction endonucleases were obtained from either Boehringer Mannheim or Promega and used according to the manufacturer's specifications. PCR fragments were synthesised with the Expand™ High Fidelity PCR System (Boehringer Mannheim 1 732 650) according to specifications. PCR fragments were synthesised in a ROBOCYCLER Gradient 40 or 96 (STRATAGENE). The standard ROBOCYCLER program consists of the following steps and temperatures: 1 cycle at 94° C. for 4 minutes, 20–25 cycles of 1 minute at 94° C., 2 minutes at 60° C., 3 minutes at 72° C. and finally 1 cycle at 72° C. for 10 minutes before storage at 6° C.

TABLE 4.1.

Genotypes and sources of *S. cerevisiae* strains used in this study. TFLR = 5,5,5-trifluoro-DL-leucine resistant

| Strain | Genotype Mating type | | | | | Source |
|---|---|---|---|---|---|---|
| S288C | α | HIS4 | MET2 | LEU4 | YOR108W | |
| JH250 | α | HIS4 | met2Δ | LEU4 | YOR108W | Hansen and Kielland-Brandt 1994 |
| XK14-13C | a | his4 | MET2 | LEU4$^{fbr}$ | YOR108W | Baichwal et al. 1983 |
| MBP94-21 | a | his4 | met2Δ | LEU4$^{fbr}$ | YOR108W | This study |
| MBP97-1 | a | his4 | met2Δ | LEU4$^{fbr}$:: | [MET2-CA leu4Δ pUC19] YOR108W | This study |
| MBP97-4 | a | his4 | met2Δ | leu4Δ | YOR108W | This study |
| MBP97-5 | a | his4 | met2Δ | leu4Δ | YOR108W | This study |
| MBP97-7 | a | his4 | met2Δ | leu4Δ | YOR108W TFLR No. 1 | This study |
| MBP97-8 | a | his4 | met2Δ | leu4Δ | YOR108W TFLR No. 2 | This study |
| MBP97-9 | a | his4 | met2Δ | leu4Δ | YOR108W TFLR No. 3 | This study |
| MBP97-10 | a | his4 | met2Δ | leu4Δ | YOR108W TFLR No. 4 | This study |
| MBP97-11 | a | his4 | met2Δ | leu4Δ | YOR108W TFLR No. 1 | This study |
| MBP97-12 | a | his4 | met2Δ | leu4Δ | YOR108W TFLR No. 2 | This study |
| MBP97-13 | a | his4 | met2Δ | leu4Δ | YOR108W TFLR No. 3 | This study |
| MBP97-14 | a | his4 | met2Δ | leu4Δ | YOR108W TFLR No. 9 | This study |
| MBP97-51 | a | his4 | met2Δ | leu4Δ | yor108w :: [yor108w MET2-CA pUC19] | This study |
| MBP97-52 | a | his4 | met2Δ | leu4Δ | yor108w :: [yor108w MET2-CA pUC19] | This study |
| MBP97-53 | a | his4 | met2Δ | leu4Δ | yor108w :: [yor108w MET2-CA pUC19] | This study |
| MBP97-54 | a | his4 | met2Δ | leu4Δ | yor108w :: [yor108w MET2-CA pUC19] | This study |
| MBP97-55 | a | his4 | met2Δ | leu4Δ | yor108w :: [yor108w MET2-CA pUC19] | This study |
| MBP97-56 | a | his4 | met2Δ | leu4Δ | ?        ? | This study |

TABLE 4.2.

Genotypes and sources of *S. carlsbergensis* strains used in this study

| Strain | Genotype or type | Source |
|---|---|---|
| M204 | *S. carlsbergensis* lager strain | Carlsberg |
| C80-CG65 | Meiotic product from M204 | Gjermansen and Sigsgaard 1981 |
| C80-CG110 | Meiotic product from M204 | Gjermansen and Sigsgaard 1981 |
| JH268 1994 | C80-CG65 met2Δ | Hansen and Kielland-Brandt |
| JH334 1994 | C-80-CG110 met2Δ | Hansen and Kielland-Brandt |
| MBP97-15 | C80-CG110 met2Δ with "loop-in" of MBP97IIIB #1 | This study |
| MBP97-16 | C80-CG110 met2Δ with "loop-in" of MBP97IIIB #2 | This study |
| MBP97-17 | C80-CG110 met2Δ with "loop-in" of MBP97IIIB #3 | This study |
| MBP97-18 | C80-CG110 met2Δ with "loop-in" of MBP97IIIB #4 | This study |
| MBP97-19 | C80-CG65 met2Δ with "loop-in" of MBP97IIIB #3 | This study |
| MBP97-20 | C80-CG110 met2Δ "Loop-out No. 39A" | This study |
| MBP97-21 | C80-CG110 met2Δ "Loop-out No. 30A" | This study |
| MBP97-46 | C80-CG110 met2Δ "Loop-out No. 61A" | This study |
| MBP97-47 | C80-CG65 met2Δ with "loop-in" of pMBP97IIIB #5 | This study |
| MBP97-48 | C80-CG65 met2Δ with "loop-in" of pMBP97IIIB #9 | This study |

TABLE 4.2.-continued

Genotypes and sources of S. carlsbergensis strains used in this study

| Strain | Genotype or type | Source |
|---|---|---|
| MBP97-49 | C80-CG65 met2Δ with "loop-in" of pMBP97IIIB #24 | This study |
| MBP97-50 | C80-CG65 met2Δ with "loop-in" of pMBP97IIIB #25 | This study |

The 40-mer oligonucleotides (Tables 4.3 and 4.4) used as primers for PCR amplification of leu4Δ and yor108w disruption sequences were synthesised by DNA Technology (e-mail oligo-@DNAtech.aau.dk). Restriction sites necessary for insertion of the PCR fragments into the plasmid and AflII sites necessary for the linearization of the final plasmids are indicated in Tables 4.3 and 4.4. The used procedure is known as splicing by overlap extension. In this procedure, two DNA fragments containing sequences that are homologous with a designed fusion point are mixed in equimolar amounts, denatured, annealed and extended to a hybrid DNA fragment. The 1.5-kb leu4Δ fragment (FIG. 22) has been made by fusing the two primary 5' and 3' leu4 PCR fragments described below. The 5' fragment of leu4Δ was amplified with the primers "leu4 97-2 EcoRI" and "leu4 97-6 C DLT B SalI". This fragment covers the leu4 sequence from −700 to +320. The 3' fragment of leu4Δ was amplified with the primers "leu4 97-3 PvuII HindIII" and "leu4 97-5 B DLT C SalI". The most 3' fragment covers the leu4 sequence from +1563 to +2020. After PCR amplification the two leu4 fragments were mixed in equimolar amounts and extended for 4 to 10 cycles in the ROBOCYCLER without the addition outer primers. After 10 extension cycles the outer primers "leu4 97-2 EcoRI" and "leu4 97-3 PvuII HindIII" were added and the amplification was continued for another 20–25 cycles. The final 1.5 kb leu4Δ DNA fragment was purified using the Prep-A-Gene matrix. The leu4Δ DNA fragment was digested with EcoRI and HindIII, purified and ligated into the dephosphorylated EcoRI-, HindIII-linearized pUC19 vector (pUC19: Yanisch-Perron et al. 1985). The resulting plasmid was designated pMBP97II.

The 0.5-kb YOR108W disruption sequence was synthesised with the splicing by overlap extension procedure.

The 5' fragment was amplified with the primers "YOR108W Link A AflII" (SEQ ID NO:17) and "YOR108W Link B SalI" (SEQ ID NO:18) (Table 4.4). The fragment covers the YOR108W sequence from +639 to +848. The 3' fragment was amplified with the primers "YOR108W Link C SalI" (SEQ ID NO:19) and "YOR108W link D AflII" (SEQ ID NO:20). The 3' fragment covers the YOR-108W sequence from +871 to +1195. After PCR amplification the two yor108w primary fragments were mixed in equimolar amounts and extended for 10 cycles in the ROBOCYCLER without the addition outer primers. After 10 extension cycles the outer primers "YOR108W link C SalI" and "YOR108W link B SalI" were added and the amplification was continued for another 20–25 cycles. The final 0.5-kb yor108w DNA fragment was purified by the Prep-A-Gene matrix. The DNA fragment was digested with SalI, purified and ligated into the dephosphorylated SalI-linearized pUC19 vector (pUC19: Yanisch-Perron et al. 1985). The final plasmid was designated pMBP97VC. The plasmid pMBP-97VC was linearized with AflII before transformation into yeast.

TABLE 4.3.

Oligonucleotides used to construct the pMBP97II leu4Δplasmid and pMBP97IIIB leu4Δ loop-in/loop-out plasmid

| leu4 Δ oligonucleotides | Oligonucleotide sequence 5' to 3' direction |
|---|---|
| LEU4 97-2 Eco RI | AGT GAATTC TAC CTG TGT GAG CTG TGT GCC GGG TGC TAC C<br>　　　EcoRI |
| LEU4 97-3 PvuII Hind III | CAC ATT ACA GCT GAA GCT T GA GCA CTA GCC CTA GAT ATG G<br>　　　　　　　PvuII　　HindIII |
| LEU4 97-5 B DLT C SalI | CCT CTG CAT CAG TTT GTC TAG TCG ACG CCT ATC AAA CTT G<br>　　　　　　　　　　　　　　　SalI |
| LEU4 97-6 C DLT C SalI | AAG TTT GAT AGG CGT CGA CTA GAC AAA CTG ATG CAG AGG G<br>　　　　　　　　SalI |

TABLE 4.4.

Oligonucleotides used for the construction of ORF YOR108w disruption plasmid

| Oligonucleotides used for yor108w disruption | Oligonucleotide sequence 5' to 3' direction |
|---|---|
| YOR108W Link A AflII | ATC <u>CTT AAG</u> CTG TAG AAA TTT GTG AAG CTG TTA AAA AGG C<br>    AflII |
| YOR108W Link B SalI | AAT CT<u>G TCG ACA</u> GCG CAA CCA CGG TCA TTG TGA CAA TGC G<br>         SalI |
| YOR108W Link C SalI | CTT <u>GTC GAC</u> GCG CTG ATC GTG TAG AAG GTT GTC TAT TTG G<br>    SalI |
| YOR108W Link D AflII | CAG <u>CTT AAG</u> GAT CCA ATG GTA AGT ATG GAA TTC TCC ACC G<br>    AflII |

4.2. Inactivation/modification of the isopropylmalate synthase activities in the leucine de novo synthesis pathway (encoded by LEU4 and YOR108W)

(i) Inactivation of LEU4fbr

Inactivation of LEU4 was done by introduction of a PCR produced leu4Δ mutant into S. cerevisiae and S. carlsbergensis spore clones by the two-step deletion procedure by Scherer and Davis (1979). The oligonucleotides used to construct the leu4Δ deletion plasmid are shown in Table 4.3.

A map of the wild type LEU4 nucleotide sequence with selected restriction sites is shown in FIG. 21. A leu4 deletion mutant has been made by removal of the coding region from nucleotide (nt) +331 to nt +1563. The leu4Δ plasmid pMBP97II is shown in FIG. 22. The deleted part corresponds to a deletion of amino acid (aa) 111 to aa 521 seen in FIG. 23. Bold letters indicates deleted amino acid residues. The remaining residues are shown in ordinary font.

The selection system is based on the non-reverting met2Δ mutation (J. Hansen personal communication). The mutation met2Δ has been chosen as selection marker. The loop-in plasmid pMBP97IIIB is based on the plasmid pMBP97II but it contains an additional 3.7-kb fragment, inserted at the HindIII site, carrying the wild type MET2-CA gene isolated from S. carlsbergensis (Hansen and Kielland-Brandt, 1994). This wild type MET2-CA gene is used for selection of transformed colonies. The leu4 deletion was made in the strain MBP94-21 containing met2Δ together with the original LEU4$^{fbr}$ described by Baichwal et al. (1983). The strain MBP94-21 was constructed from a cross between JH250 (Hansen and Kielland-Brandt 1994) and XK14-13C (Baichwal et al 1983).

After transformation of MBP94-21 with pMBP97IIIB DNA linearized with AflII selection for transformants was done on SC-methionine selective plates. Incubation of cells was done at 27° C. Of the recovered colonies, one, MBP97-1, was chosen for the further experiments.

In order to pick up spontaneous loop-out of the selective plasmid together the adjacent wild type LEU4 gene, the strain MBP97-1 was serially transferred in liquid high glucose medium and grown to log phase to relax the selective pressure.

A suspension of cells from the third transfer was diluted and plated onto rich high glucose solidified medium plated at a concentration of 250–400 colonies on each of the 120 plates. After incubation for 4–5 days at 27° C. each plate was replica plated onto plates containing solidified SC-methionine and rich high glucose medium, respectively. Colonies which did not grow on SC-methionine plates were assumed to have loopedout the plasmid containing the wild type MET2-CA gene in the plasmid.

Two met2 loop-out clones were further tested to confirm that they contained the deleted version of LEU4. They were tested by replica plating to various drop-out plates including SC-leucine and SC-leucine+TFL. The loop-out clones designated MBP97-4 and MBP97-5 are both auxotrophs for methionine and sensitive to 5,5,5-trifluoro-DL-leucine (TFL), thus indicating that the original LEU4$^{fbr}$ was inactivated. PCR amplifications of the LEU4 regions in MBP97-4 and MBP97-5 showed that both clones contains the deleted version of LEU4$^{fbr}$.

(ii) Inactivation of the LEU4 homologue designated ORF YOR108w

The ORF YOR108w disruption vector pMBP97VB is based on the vector pUC19 (Yanisch-Perron et al. (1985) containing the 3.7-kb HindIII fragment carrying MET2-CA from S. carlsbergensis as selective marker. The sequences necessary for integration to the ORF YOR108w region are inserted into the SalI site of the pUC19 plasmid. The linkers and sequences necessary for integration are shown in Table 4.4 and FIGS. 24 and 25. Due to the high sequence homology between LEU4 and ORF YOR108w the integration linkers used in the disruption plasmid pMBP97VB are within the deleted area of leu4Δ (Table 4.4, FIGS. 24 and 25). This precaution will force all integration to happen at YOR108W.

To elucidate the effect of Yor108wp, an YOR108w disruption mutant designated yor108w was introduced in the leu4Δ strain MBP97-4. The leu4 yor108w double mutants MBP97-51, MBP97-52, MBP97-53, MBP97-54 and MBP97-55 exhibited leaky leucine auxotroph phenotypes (FIG. 26) but they appeared to require isoleucine and valine as well. Numbers 1,2,3,4 and 5 indicate colonies requiring leucine, whereas the colony designated 6 is growing relatively well on SC-leucine and SC-methionine. Colony number 6 was not investigated further.

A sample of S. cerevisiae strain MBP97-52 was deposited on Jul. 8, 1998 in accordance with the Budapest Treaty with the American Type Culture Collection (ATCC) under the Accession No. 74455.

Southern blot analysis of electrophoretic karyotypes, PCR amplifications and analysis of restriction endonuclease digested total DNA confirmed the inactivation of LEU4 and YOR108W giving rise to the leu4Δ and yor108w double mutants.

(iii) Inactivation of LEU4 in S. carlsbergensis

The LEU4 deletion plasmid pMBP97IIIB has been introduced to the two met2Δ spore clones JH268 and JH334 (Table 4.2). Its introduction to correct position in both their genomes was confirmed by PCR analysis, electrophoretic karyotype analysis and Southern analysis of digested total DNA. It was expected that the deletion plasmid had integrated at the cerevisiae-like LEU4-CE allele in the spore clones. Three loop-out clones from the first analyzed strains MBP97-19, MBP97-20 and MBP97-46 were identified on SC-methionine drop-out plates. Only one strain, MBP97-46, showed loop-out of the pUC19 sequence.

During Southern analysis of JH334 and JH268 at least one LEU4-CE and one LEU4-CA sequence was identified in each strain. There is at least one YOR108W-CE sequence present in the spore clones.

The strategy is to introduce the YOR108W disruption plasmid into the *S. carlsbergensis* specific LEU4 sequence and thereby producing a leu4 allodiploid heterozygous for met2-ceΔ met2-caΔ leu4-ceΔ and leu4-ca:: [MET2-CA yor108w pUC19]. The rationale is that LEU4 and YOR108W are almost identical in the chosen region for introduction of the disruption sequence. It is therefore assumed that the integration occurs equally frequent at LEU4 on chromosome XIV and YOR108W on chromosome XV. The localisation of the integrated disruption plasmid has been performed by Southern blot analysis of electrophoretic karyotype analysis.

(iv) Fermentation studies

*S. cerevisiae* LEU4$^{fbr}$, LEU4 and leu4Δ

*S. cerevisiae* reference and mutant strains were grown aerobically at 20° C. for five days in 50 ml PS medium. The cultures were inoculated with 1 ml culture at a density of 10$^7$ cells/ml. In Table 4.5 are shown GC-headspace analysis (cf. 5.5 (iii) GC-headspace analysis) of 3-methyl-l-butanol and 2-methyl-1-butanol together (MlB) the corresponding acetate esters (MBA), 2-methyl-1-propanol (2M1P) (same as isobutanol) and isobutylacetate (IBAC). As background values are used those for the unfermented rich high glucose growth medium.

The LEU4$^{fbr}$ containing strains (MBP94-21 and MBP97-1) produced very high amounts of MIB when compared to the LEU4 wild type strains (S288C and JH250. The two leu4Δ strains MBP97-4 and MBP97-5 produced an amount of MlB equivalent but not less than what is produced by LEU4 wild types (S288C and JH250).

TABLE 4.5.

GC-Headspace analysis of produced volatiles from *S. cerevisiae* reference strains and LEU4 mutants from the first fermentation trials in rich high glucose (PS) medium. Values are in ppm. M1B indicates the combined peak containing both 3M1B (isoamyl alcohol) and 2M1B (active amyl alcohol). MBA are corresponding esters 3MBA (isoamylacetate) and 2MBA (active amyl acetate)

| Strain | Genotype | M1B | MBA |
| --- | --- | --- | --- |
| PS medium | — | 0.16 | 0.01 |
| S288C | MAT α HIS4 MET2 LEU4 | 139 | 0.33 |
| JH250 | MAT α HIS4 met2 LEU4 | 105 | 0.07 |
| MBP94-21 | MAT a his4 met2 LEU4-fbr | 397 | 0.20 |
| MBP97-1 | MAT a his4 MET2 LEU4-fbr | 613 | 2.50 |
| MBP97-4 | MAT a his4 met2 leu4 "27A" | 129 | 0.27 |
| MBP97-5 | MAT a his4 met2 leu4 "41A" | 137 | 0.30 |
| MBP97-7 | MAT a his4 met2 leu4 TFL-R "27A-1-TFLR" | 178 | 0.31 |
| MBP97-8 | MAT a his4 met2 leu4 TFL-R "27A-2-TFLR" | 177 | 0.40 |
| MBP97-9 | MAT a his4 met2 leu4 TFL-R "27A-3-TFLR" | 185 | 0.61 |
| MBP97-10 | MAT a his4 met2 leu4 TFL-R "27A-4-TFLR" | 176 | 0.49 |
| MBP97-11 | MAT a his4 met2 leu4 TFL-R "41A-1-TFLR" | 151 | 0.11 |
| MBP97-12 | MAT a his4 met2 leu4 TFL-R "41A-2-TFLR" | 123 | 0.04 |

TABLE 4.5.-continued

GC-Headspace analysis of produced volatiles from *S. cerevisiae* reference strains and LEU4 mutants from the first fermentation trials in rich high glucose (PS) medium. Values are in ppm. M1B indicates the combined peak containing both 3M1B (isoamyl alcohol) and 2M1B (active amyl alcohol). MBA are corresponding esters 3MBA (isoamylacetate) and 2MBA (active amyl acetate)

| Strain | Genotype | M1B | MBA |
| --- | --- | --- | --- |
| MBP97-13 | MAT a his4 met2 leu4 TFL-R "41A-3-TFLR" | 123 | 0.04 |
| MBP97-14 | MAT a his4 met2 leu4 TFL-R "41A-9-TFLR" | 110 | 0.09 |

Leu4Δ and yor108w double mutants

In order to monitor the cell growth and the fermentation performed by the leu4 yor108w double mutation, the double mutant strain MBP97-52 was tested in three different liquid media. Six strains were grown in rich glucose medium (PS), SC and SC-leucine medium, respectively (Table 4.6). The following *S. cerevisiae* strains were used: S288C, JH250, MBP94-21, MBP97-1, MBP97-4 and MBP97-52 (Table 4.1). In the preliminary experiments, the double mutant leu4Δ yor108w still produced M1B in an amount equivalent to the LEU4 YOR108W wild type strains. It is, however, assumed that the majority of the recovered M1B originate from the leucine taken up by the yeast cell from the growth media, as MBP97-52 was unable to grow on synthetic complete medium without leucine (SC-leucine).

TABLE 4.6.

GC-Headspace analyses of produced volatiles from *S. cerevisiae* reference strains and leu4Δ yor108w double mutant strain MBP97-52 from the first fermentation trials in SC, SC-leucine and rich glucose medium (PS), respectively. Values are in ppm. M1B indicates the combined peak containing both 3M1B (isoamyl alcohol) and 2M1B (active amyl alcohol). MBA are corresponding esters 3MBA (isoamylacetate) and 2MBA (active amyl acetate)

| STRAIN | M1B SC | M1B SC-LEU | M1B PS | MBA SC | MBA SC-LEU | MBA PS |
| --- | --- | --- | --- | --- | --- | --- |
| S288C | 8,327 | 10,088 | 130,25 | 0,018 | 0,023 | 0,373 |
| JH250 | 7,726 | 8,363 | 123,431 | 0,017 | 0,02 | 0,307 |
| MBP94-21 | 65,619 | 45,908 | 314,811 | 0,041 | 0,031 | 0,713 |
| MBP97-1 | 60,482 | 49,432 | 371,279 | 0,044 | 0,065 | 0,962 |
| MBP97-4 | 9,223 | 5,343 | 126,604 | 0,019 | 0,015 | 0,258 |
| MBP97-52 | 24,36 | 0,972 | 186,26 | 0,025 | 0,013 | 0,383 |
| PS background | | | 1,71 | | | 0,014 |
| SC background | 0,42 | | | 0,014 | | |
| SC-LEUCINE background | | 0,168 | | | 0,013 | |

(v) Inactivation of an α-ketoisocaproate decarboxylase encoded by the open reading frame YDL080c.

The present invention contemplates to produce yeast strains where the Ydl080cp (Thi3p) enzyme is inactivated either by a deletion or by a gene disruption. The inactivation of YDL080C assumingly will give rise to reduced production of 3-methyl-1-butanol (isoamyl alcohol) and consequently reduced production of 3-methyl-1-butyl-acetate.

The gene is inactivated by a disruption plasmid pMBP98IA based on the vector pUC19. The vector is opened by HindIII and a 3.7-kb HindIII fragment containing MET2-CA is ligated into the opened vector. This plasmid is designated pMBP96A2. The SalI site in the remaining pUC19 multi-cloning site is opened and an approximately 500 bp SalI fragment is ligated into the plasmid. The 500-bp SalI fragment contains 250 bp of the region nt +1721 to +1971 and 250 bp of the region nt −249 to +1. The restriction enzyme AflII linearises the plasmid pMBP98IA.

It is also contemplated to use the ydl080 mutation in combination with mutations in any of the following genes LEU4, YOR108W, ATF1 and ATF2 in strains of any Saccharomyces species including the lager yeast strain S. carlsbergensis.

EXAMPLE 5

Lowered ester content in beer by inactivation of genes coding for alcohol acetyltransferases in Saccharomyces 5.1. Introduction Acetate esters are important flavour components in fermented beverages such as beer, wine and whisky. The acetate esters are produced by the yeast by metabolism of branched chain amino acids such as leucine, isoleucine and valine and are formed from higher alcohols and acetyl coenzyme A by alcohol acetyltransferases.

The aim of the present study was to inactivate the genes coding for the alcohol acetyltransferases in S. carlsbergensis lager yeast in an attempt to lower the content of the acetate esters isoamyl acetate and ethyl acetate in beer.

5.2. Materials and Methods

Genotypes of the yeast strains used in this study are shown in Tables 5.1 and 5.2. S. carlsbergensis lager yeast strains, C80-CG65(MATa) and C80-CG110(MATα) are spore clones of M204, an in-house Carlsberg lager yeast strain. Agar plates with rich medium high in glucose (PS-medium) or plates with synthetic complete medium (SC) or synthetic complete medium without methionine (SC-methionine) for selection were made according to Sherman (1991). For selection of G418-resistant transformants of S. carlsbergensis, G418 (geneticin) was used at a concentration of 30 μg/ml in YPD (1% yeast extract, 2% peptone, 2% glucose).

TABLE 5.1.

Genotypes and source of S. cerevisiae yeast strains

| Yeast strain | Mating type | Genotype or type | | | | | Source |
|---|---|---|---|---|---|---|---|
| S288C | α | HIS4 | MET2 | LEU4 | | ATF1 ATF2 | |
| JH250 | α | HIS4 | met2Δ | LEU4 | | ATF1 ATF2 | Hansen and Kielland-Brandt 1994 |
| XK14-13C | a | his4 | MET2 | LEU4$^{fbr}$(*) | | ATF1 ATF2 | Baichwal et al. 1983 |
| MBP94-21 | a | his4 | met2Δ | LEU4$^{fbr}$(*) | | ATF1 ATF2 | This study |
| SBS97-1 | a | his4 | met2Δ | LEU4$^{fbr}$(*) | | atf1Δ ATF2 | This study |

(*)5,5,5-trifluoro-DL-leucine (TFL) resistant mutant containing leucine feed-back resistant (fbr) α-isopropylmalate synthase.

TABLE 5.2.

Genotypes and source of S. carlsbergensis strains

| Yeast strain | Mating type | Genotype or type | | | Source |
|---|---|---|---|---|---|
| M204 | | S. carlsbergensis lager strain | ATF1-CE/ATF1-CA | ATF2-CE/* | Carlsberg |
| C80-CG65 | a | Meiotic segregant from M204 | ATF1-CE/ATF1-CA | ATF2-CE/* | Gjermansen and Sigsgaard 1981 |
| C80-CG110 | α | Meiotic segregant from M204 | ATF1-CE/ATFI-CA | ATF2-CE/* | Gjermansen and Sigsgaard 1981 |
| SBS97-3 | a | C80-CG65 | atf1-ceA/ATF1-CA | ATF2-CE/* | This study |
| SBS97-6 | α | C80-CG110 | atf1-ceA/ATF1-CA | ATF2-CE/* | This study |
| SBS97-7 | α | C80-CG110 | ATF1-CE/atf1-caΔ | ATF2-CE/* | This study |
| SB597-8 | α | C80-CG110 | atf1-ceA/atf1-caΔ | ATF2-CE/* | This study |

*It is not known whether S carlsbergensis strains have two forms of the ATF2 gene.

Plasmids were prepared from *E. coli* DH5α as described by Sambrook et al. (1989) or by use of "Wizard Plus Midipreps DNA Purification System" (Promega A7640). Plots of plasmids with restriction analysis were drawn using the program pDRAW (K. Olesen, personal communication [E-mail: kol@crc.dk]). Restriction endonucleases and DNA modifying enzymes were from Boehringer Mannheim, New England Biolabs or Promega and used in accordance with the manufacturers procedures. Oligonucleotides were obtained from DNA Technology, Aarhus, Denmark. All chemicals were of the highest purity available.

Yeast transformation was done by the lithium acetate method according to Schiestl and Gietz (1989) and Gietz et al. (1992). Genomic DNA was isolated in FMC Incert agarose according to the method of Schwartz and Cantor (1984) with the modification by Pedersen (1988). Separation of chromosomal length DNA molecules was performed in 1.3% FMC FastLane Agarose by pulsed field electrophoresis in a Bio-Rad CHEF MAPPER System. The buffer used was 0.5 ×TBE (0.044 M Trisborate, 0.001 M EDTA). Southern blotting of DNA in agarose gels was done after depurination (0.25 M HCl in 30 min.), denaturation (0.4 M NaOH+0.6 M NaCl in 60 min.) and neutralization (1.0 M Tris+1.5 M NaCl, pH 7.2 in 120 min.) of the gel to Hybond N nylon membrane from Amersham Life Science. The DNA was fixed to the membrane by UV crosslinking using a Stratagene UV Stratalinker 2400 and Southern blot DNA hybridization performed with a probe which was either labelled with α-$^{32}$P-dCTP (NEN Life Science Products) using the "Random Primed DNA Labeling and Detection Kit" (Boehringer Mannheim 1 004 760) or with digoxigenin-dUTP employing the "DIG DNA Labeling and Detection Kit" (Boehringer Mannheim 1 093 657). The labelling was performed according to the manufacturer's procedure.

Inactive forms of the ATF-genes were constructed by three PCR-reactions using a Perkin Elmer DNA Thermal Cycler or Stratagene RoboCycler Gradient 40 or 96. The Expand High Fidelity PCR System (Boehringer Mannheim 1 732 650) was used with genomic DNA as template and oligonucleotide primers homologous to sequences in the alcohol acetyltransferase genes (SEQ ID NOS:21–40) (Table 5.3). The DNA sequences were obtained from the Saccharomyces Genome database (http://genome-www.stanford.edu/Saccharomyces/) or the Genbank database (NCBI) (http://www.ncbi.nlm.nih.gov/). By PCR reactions two DNA fragments, designated PCR1 and PCR2, about 400 to 700 bp in length were synthesized. PCR1 was identical to a region upstream or the beginning of the alcohol acetyltransferase gene in question, whereas PCR2 was identical to a region downstream or the end of the gene in question. In a third reaction, a PCR fragment comprising an inactive ATF gene, leaving out 500 to 2,000 bp of the DNA coding for the transferase gene (see Table 5.4) was synthesized with restriction sites for cloning at the ends using PCR1 and PCR2. The procedure is known as splicing by overlap extension, as two PCR-fragments containing homologous sequences with a predetermined fusion point are mixed in equimolar amounts, denatured, annealed and extended to a hybrid PCR-fragment. The PCR-fragments were purified from agarose gels employing "Prep-A-Gene DNA Purification System" (Bio-Rad cat. no. 732-6010, USA).

TABLE 5.3.

Oligonucleotide primers used for synthesis of PCR fragments employed to delete part of the alcohol acetyl transferase genes

| Gene | PCR-fragment | Restriction site | oligonucleotide sequences | Position in sequence relative to initiation codon of gene |
|---|---|---|---|---|
| *S. cerevisiae* | | | | |
| ATF1 | PCR1 | SacI | 5'-AGG CTG AGC TCC TCC TGG AAT GTT AAG ACT TTC TC | −1219 → −1195 |
| | | | 5'-GGG TAG CAA AAC TGT CCA GAG C TCG TGC CAT CGG G | −640 → −661 |
| | PCR2 | | 5'-GCT CTG GAC AGT TTT GCT ACC CAT GTG CGA TCG TGC CAT CGG G | −661 → −640 and +1300 → 1320 |
| | | PstI | 5'-AGA TCT CTG CAGCTA ATC AAA TCA ATT AAT | +1833 → +1804 |
| ATF2 | PCR1 | SalI | 5'-GCA CGC GTC GAC CTA CAT TGA ACT CTG TAG GCC ACC G | −300 →−276 |
| | | | 5'-CTC CAT GAC TTC TCT GTA TTC TGG | +384 → +361 |
| | PCR2 | | 5'-CCA GAA TAC AGA GAA GTC ATG GAG CGG CTC CAA CGT TGG AGG TTC GC | +361 → +384 and +1125 → +1147 |
| | | SphI | 5'-GAG CAG CCA CGG CAT GCA TCG ACT | +1730 → +1707 |
| *S. carlsbergensis* C80-CG65 and C80-CG110 | | | | |
| ATF1-CE | PCR1 | XbaI | 5'-AGC TAG TCT AGA GTG TGA GGA CTA CTC ATT GGC TTG | −230 → −207 |
| | | | 5'-ACT GCA CTG TAC TCA GGT TGT TCA | +392 → +369 |
| | PCR2 | | 5'-TGA ACA ACC TGA GTA CAG TGC AGT CGC AGA TTG CCG CTC ACA ACT ACC | +369 → +392 and +1044 → +1067 |
| | | SacI | 5'-AGC TGC GAG CTC ACA CGA CAT AAT CAT ATT GTC G | +1629 → +1608 |
| ATF1-CA | PCR1 | XbaI | 5'-AGC TAG TCT AGA TTG AAC ATT GAT CAA TGT GAA | −249 → −229 |
| | | | 5'-CCA TCT TGC CGG TAA TAC AAT A | +315 →+294 |
| | PCR2 | | 5'-TGT ATT ACC GGC AAG ATG GCC ACT TAT TGC ACA TTA TCA T | +297 → +315 and +1240 → +1260 |

TABLE 5.3.-continued

Oligonucleotide primers used for synthesis of PCR fragments employed to delete part of the alcohol acetyl transferase genes

| Gene | PCR-fragment | Restriction site | oligonucleotide sequences | Position in sequence relative to initiation codon of gene |
|---|---|---|---|---|
| | | SacI | 5'-AGC TGC GAG CTC CAC TTA CTT ACC TTA CAC ACG TCG TT | +1822 → +1797 |
| ATF2-CE | PCR1 | XbaI | 5'-AGC TAG TCT AGA AGC GTA CTA CTC TAG CGA AGA GTA | +255 → +278 |
| | | | 5'-CAG TGT AGT CTC GAT CAT AGT CAA | +709 → +686 |
| | PCR2 | | 5'-TTG ACT ATG ATC GAG ACT ACA CTG GTC GAA TAC TAC TAT GAC CGC TT | +686 → +709 and +1213 → +1235 |
| | | SacI | 5'-TGT ACG AGC TCG GCC GAG CTA TAC | +1657 → +1634 |

Restriction sites incorporated in the oliganucleotides are underlined.

TABLE 5.4.

Nucleotides removed by inactivation of genes coding for alcohol acetyltransferases

| Gene | | Nucleotides deleted relative to initiation codon | Fragment deleted |
|---|---|---|---|
| ATF1 | (*S. cerevisiae*) | −639 → +1299 | 1938 bp |
| ATF2 | (*S. cerevisiae*) | +385 → +1124 | 740 bp |
| ATF1-CE | (*S. carlsbergensis* C80-CG65 and C80-CG110) | +393 → +1043 | 651 bp |
| ATF1-CA | (*S. carlsbergensis* C80-CG65 and C80-CG110) | +316 → +1239 | 924 bp |
| ATF2-CE | (*S. carlsbergensis* C80-CG65 and C80-CG110) | +710 → +1212 | 503 bp |

In *S. cerevisiae*, the selectional system was based on the non-reverting met2Δ mutation (J. Hansen personal communication). Integration plasmids pSBS97-1 (FIG. 27) and pSBS97-2 (FIG. 28) for ATF1 and ATF2, respectively, were constructed by ligation of the PCR fragments comprising the inactive forms of the ATF-genes (see above) into the SacI-PstI sites (ATF1) or SalI-SphI sites (ATF2) of pMBP96A2. The plasmid pMBP96A2 (FIG. 29) was produced from pUC19 (Yanisch-Perron et al., 1985) by inserting a 3.7 kb HindIII fragment including the *S. carlsbergensis* specific allele of MET2 (MET2-CA), which encodes a homoserine acetyltransferase (Hansen and Kielland-Brandt, 1994), into the HindIII site of pUC19. The MET2-CA gene thus conferred prototrophy for methionine in *S. cerevisiae* MBP94-21 (see Table 5.1) when this strain was transformed with either pSBS97-1 or pSBS97-2.

In *S. carlsbergensis*, integration plasmids were constructed by ligation of the PCR fragments comprising the inactive forms of the ATF-genes (see above) into the XbaI and SacI sites of the integration vector pCH216 containing a G418-resistance cassette as selective marker (Hadfield et al., 1990). In this way the integration plasmids pSBS97-3 and pSBS97-6 for ATF1-CE (FIG. 30), pSBS97-4 and pSBS97-7 for ATF1-CA (FIG. 31) and pSBS97-5 and pSBS97-8 for ATF2-CE (FIG. 32) were constructed. Genomic DNA from C80-CG65(MATa) was used as template for the synthesis of the inactive forms of the ATF-genes inserted into pSBS97-3, pSBS97-4 and pSBS97-5 while genomic DNA from C80-CG110(MATα) was used as template for the synthesis of the inactive forms of the ATF-genes inserted into pSBS97-6, pSBS97-7 and pSBS97-8.

5.3. Construction of haploid laboratory yeast with eliminated or reduced alcohol acetyltransferase activity.

To test the hypothesis that inactivation of alcohol acetyltransferase genes in yeast results in lowered amounts of esters in the fermented medium, inactive forms of ATF1 and ATF2 were introduced into the haploid laboratory yeast MBP94-21 by homologous recombination between deletion alleles and wild-type alleles of the genes. MBP94-21 is auxotrophic for methionine and overproduces isoamyl alcohol and isoamyl acetate (Table 5.1). The two-step loop-in/loop-out procedure of Scherer and Davis (1979) was employed to substitute the wild-type allele of each alcohol acetyltransferase gene in MBP94-21 with deletion alleles. The construction of the inactive forms of ATF1 and ATF2 and insertion into the integration plasmids is described above. The integration plasmid pSBS97-1 was linearized with NsiI (FIG. 27) while pSBS97-2 was linearized with MscI (FIG. 28) and MBP94-21 transformed with the linearized plasmids. As NsiI cuts twice in pSBS97-1, the DNA preparation was only partially digested. Transformants were selected as being able to grow on SC-methionine plates. To confirm that integration had taken place at the location of the wild-type alleles Southern blots and hybridizations with labelled linearized pUC19 DNA as probe were performed on agarose gels, where genomic DNA had been separated by pulsed field gel electrophoresis.

In order to loop-out the selective plasmid together with the adjacent wild type ATF-gene leaving only the inactive alcohol acetyltransferase gene on the chromosome, two integrants were grown to stationary phase 3 times in rich medium high in glucose content (PS-medium) with 100-fold dilution of each stationary culture into fresh PS-medium. Ten thousand to twenty thousand cells of the third stationary culture were screened for spontaneous loop-out of the vector DNA and the wild-type copy of the gene in question by plating on solid PS-medium (50–100 plates). After incubation for 4–5 days at 27° C. the colonies on each plate were replica-plated to two plates with SC-methionine and PS-medium, respectively. The colonies that were unable to grow on SC-methionine were picked and analyzed by Southern blots and hybridizations of genomic DNA digested with StuI or KpnI to identify those, where an inactive deletion allele had substituted the wild-type gene. In this way, mutant strains of MBP94-21 with inactive alcohol acetyltransferase genes were isolated.

5.4. Construction of *S. carlsbergensis* lager Yeast strains with eliminated or reduced alcohol acetyltransferase activity.

To test the hypothesis that inactivation of alcohol acetyltransferase genes in yeast results in beer with a lowered amount of the esters isoamyl acetate and ethyl acetate inactive forms of ATF1-CE, ATF1-CA and ATF2-CE were introduced into the spore clones C80-CG65 and C80-CG110 by homologous recombination between deletion alleles and wild-type alleles of the genes (the loop-in/loop-out technique) in a procedure similar to that described for *S. cerevisiae* laboratory yeast. The construction of the inactive forms of ATF1-CE, ATF1-CA and ATF2-CE is described above. The two-step integration procedure of Scherer and Davis (1979) as described above was employed. The integration plasmids were linearized with the restriction endonucleases SphI (pSBS97-3, pSBS97-6) (FIG. 30), SapI (pSBS97-4, pSBS97-7) (FIG. 31) or StuI (pSBS97-5, pSBS97-8) (FIG. 32), respectively. Since SapI cuts twice in pSBS97-4 and pSBS97-7, the DNA preparations were only partially digested.

The spore clone C80-CG65 was transformed with each of the linearized plasmids pSBS97-3, pSBS97-4 and pSBS97-5 while C80-CG110 was transformed with the linearized plasmids pSBS97-6, pSBS97-7 and pSBS97-8. Transformants were selected as being geneticin resistant. To confirm that integration had taken place at the location of the wild-type alleles, Southern blots and hybridizations were carried out. Loop-out of the vector DNA together with the wild type gene, leaving only one copy of the inactive alcohol acetyltransferase gene on the chromosome, was carried out as described for the laboratory yeast strain MBP94-21. Ten thousand to twenty thousand cells were screened by plating on PS-medium (50–100 plates) and after incubation 4–5 days at 20° C. the colonies were replica-plated onto two plates with solid YPD with geneticin and PS-medium, respectively. The colonies that had become sensitive to geneticin were picked and analyzed as described above by Southern blots and hybridizations to identify those, where an inactive deletion allele had substituted the wild-type gene. In this way, spore clones having one of the genes coding for alcohol acetyltransferase in an inactive form were isolated.

5.5. Fermentation studies (i) *S. cerevisiae* strains.

Liquid rich medium high in glucose content (10 ml PS-medium in 25 ml tube) was inoculated with the appropriate yeast strain and grown overnight at 30° C. 1–2 ml of this culture containing $10^7$ cells was used to inoculate 50 ml fresh medium in a 250 ml conical flask. The culture was incubated at room temperature for 5 days with agitation (90 rpm.). Yeast cells were sedimented overnight at 4° C. and the supernatant discarded. 50 ml fresh medium was added to the cells and 2. generation fermentation performed as above. 25 ml supernatant from the fermentation was delivered for GC-headspace analysis (see below) to determine the content of esters and alcohols. The results are shown in Table 5.5. The yeast strains carrying inactive alcohol acetyltransferase genes produced a reduced amount of acetate esters such as ethyl acetate and isoamyl acetate in comparison to the MBP94-21 strain.

TABLE 5.5

GC-headspace analysis of volatiles produced by *S. cerevisiae* yeast strains. Values are in ppm

| Compound | Yeast strain | |
|---|---|---|
| | MBP94-21 | SBS97-1 |
| Ethyl acetate | 2.60 | 1.75 |
| Isoamylacetate + active amylacetate | 0.21 | 0.12 |
| Isoamylalcohol | 290 | 257 |

(ii) *S. carlsbergensis* lager yeast strains.

Instead of rich medium high in glucose content (PS-medium) fermentation of brewers wort was performed as described for the laboratory yeast. Incubation at 20° C. was used in all cases.

(iii) GC-headspace analysis.

GC-headspace analysis was carried out on a Perkin-Elmer GC8500 with HS 101 headspace sampling and Turbochrome analytical software. A 50 m CP-WAX 52 CB capillary column (0.32 mm inner diameter and 1.20 μm film thickness) was temperature programmed: 60° C. for 1 min. −10° C./min. to 110° C.−110° C. for 4 min. −30° C./min. to 175° C.−175° C. for 4 min. −30° C./min. to 225° C.−225° C. for 1 min. The injection temperature was 140° C. and the detection temperature 250° C. The carrier gas was helium at 15.0 psi. Vials for the autosampler were filled with 5 ml supernatant of fermented medium together with 1.5 g NaCl, a magnet and 1 ml internal standard (n-pentylacetate).

(iv) Results

At present, the *S. cerevisiae* strain SBS97-1 where ATF1 is inactivated (see Tabel 5.1) has been isolated and loop-in of pSBS97-2 in *S. cerevisiae* MBP94-21 is correct. Preliminary fermentation with SBS97-1 to stationary phase in two generations has by GC-headspace analysis revealed 40% decrease in the content of isoamyl acetate compared to a similar analysis performed with *S. cerevisiae* MBP94-21 (Table 5.5).

The *S. carlsbergensis* lager yeast strains SBS97-6, where ATF1-CE is inactivated, and SBS97-7, where ATF1-CA is inactivated, have been isolated (Table 5.2). In the mutant strain SBS97-6 it has been attempted to substitute wild-type ATF1-CA with a deletion allele. Ten possible loop-out colonies have been investigated by restriction Southern analysis to identify correct loop-out mutant strains. Nine were found to have looped-out leaving the wild-type gene in the chromosome, while the last colony, SBS97-8 (Table 5.2), presumably had lost the chromosome carrying ATF1-CA. At present, two loopout colonies are investigated by Southern hybridizations for loop-out of ATF1-CE in C80-CG65. One of these presumably has lost the chromosome carrying ATF1-CE, resulting in the mutant strain SBS97-3 (Table 5.2).

When allodiploid spore clones of C80-CG65 and C80-CG110 having inactive alleles of both ATF1-CE and ATF1-CA (or having lost the chromosomes carrying these genes) are obtained, these will be crossed with each other to reconstitute allotetraploid lager yeast strains, which can be tested technologically in cylindroconical fermentation vessels.

A sample of *S. cerevisiae* strain SBS97-1 was deposited on Jul. 8, 1998 in accordance with the Budapest Treaty with the American Type Culture Collection (ATCC) under the Accession No. 74450.

EXAMPLE 6

Production of a composite beer by combining high- and low-sulphite containing batches of beer 6.1. Summary of the experiments A new approach has been made towards production of a beer containing satisfactory amounts of sulphite and at the same time having a normal beer flavour profile. Two independent beer batches were produced using two individual yeast strains, both genetically modified. One yeast strain, PFJ501, was inactivated in all four copies of the MET14 gene encoding the APS kinase (EC 2.7.1.25) (see Example 1), resulting in very low or absent sulphite production during fermentation. The other yeast strain, SB130, was inactivated in all four copies of the MET10 gene, encoding one subunit of the sulphite reductase enzyme (EC 1.8.1.2), (Hansen and Kielland-Brandt, 1996b) resulting in a dramatically increased sulphite production during fermentation.

The two batches of beer brewed using the two individual yeast strains were combined to obtain a predetermined sulphite content of 15 ppm in the final composite beer. Based on evaluation by an experienced taste panel, the composite beer obtained higher score after forced aging as compared to the two individual beers, and it was comparable to a reference beer brewed from a normal production strain.

6.2. Materials and methods

Strains and media

The three *Saccharomyces carlsbergensis* strains used were PFJ501 (see Example 1, Table 1), SB130 (Hansen and Kielland-Brandt, 1996b) and M204 as a reference production strain (see Example 1, Table 1). Brewer's wort with a gravity of 14.6% Plato was used for the 50 L-scale fermentations.

Fermentation at 50 L scale

After propagation, yeast was inoculated in brewer's wort at $1.5 \times 10^7$ cells/ml in 50 L fermentation vessels. Fermentation was performed at 13° C. The yeast was harvested after 10 days and the beer was left in the vessels for 8–12 days of lagering. The harvested yeast was used as inoculum for the following brewing generations.

Other analyses

Either fermentation samples (the supernatant from centrifuged samples) or bottled beer were assayed for total $SO_2$ using headspace chromatography with a Sulfur Chemiluminescence Detector (SCD) (Lowe and Dreyer, 1997).

6.3. Results (i) Production and evaluation of the flavour stability of a composite beer versus individual batches of beer with high or low sulphite content.

Fermentation of brewer's wort with strains PFJ501 and SB130 were performed at 50 L scale, and the production strain M204 was used as a reference. The sulphite production was followed during fermentation (Table 6.1). Fermentation with strain PFJ501 resulted in a very low sulphite production, whereas strain SB130 produced high amounts of sulphite as compared to the reference strain M204. With respect to the different brewing parameters, strains PFJ501 and SB130 performed normally.compared to the reference strain M204.

Prior to bottling the low- and high-sulphite beers were combined to obtain a composite beer containing 13 ppm of sulphite. This was done by mixing 11.4 litres of the beer produced by strain SB130 with 13.6 litres of the beer produced by strain PFJ501 to obtain a total of 25 litres of composite beer having a calculated sulphite content of 15 ppm (the difference of 2 ppm sulphite disappears during bottling). The composite beer was bottled as were the two individual batches of beer from which it was made, along with the reference beer.

TABLE 6.1.

Sulphite production during fermentation at 50 L scale from the three strains M204 (reference), SB130 (high sulphite producer) and PFJ501 (low sulphite producer). The last column represents the amount of sulphite measured in the bottled beer. All numbers are from the 2. brewing generation.

| | $SO_2$/ppm | | | | | | | | | |
|---|---|---|---|---|---|---|---|---|---|---|
| Strain | 2. day | 3. day | 6. day | 7. day | 10. day | 13. day | 14. day | 15. day | 17. day | Bottled beer |
| M204 | 0 | 1.4 | 5.7 | 8.5 | 7.1 | 6.4 | 6.4 | 6.4 | — | 4 |
| SB130 | 7.8 | 23 | 28 | 50 | 41 | — | 40 | 36 | 38 | 33 |
| PFJ501 | 0 | 0.7 | 0 | 0.7 | 0.7 | 0 | 0 | 0.7 | — | 0 |
| Mixture | — | — | — | — | — | — | — | — | — | 13 |

The bottled beer was judged by an experienced taste panel before and after forced aging (7 days at 37° C.). The evaluation of the beers is presented graphically in FIG. 27. Before aging, beer produced with strain PFJ501 was assessed as "not quite satisfactory", and so was beer produced with strain SB130, whereas the composite beer was "satisfactory" in line with the reference beer. After forced aging, the two individual beers from strain PFJ501 and SB130 were judged "not satisfactory" and "not quite satisfactory", respectively. The composite beer was assessed as "not quite satisfactory" along with the reference beer (FIG. 33).

6.4. Conclusion

By combining two different batches of beer made by individual recombinant brewer's yeast strains, one having enhanced production of sulphite and one having no sulphite production, it was possible to make a composite beer which fulfills specific criteria, in this case a beer containing a predetermined sulphite level of 15 ppm and at the same time being as satisfactory with respect to taste and flavour stability as is a conventionally produced reference beer.

When the mixture of PFJ501-based and SB130-based beer was evaluated by an experienced taste panel this composite beer obtained scores comparable to the reference beer. This shows that it is possible to produce a composite beer having a desired characteristic by mixing individual beer batches produced by yeast strains modified by recombinant genetics to have enhanced and decreased production of the compound causing that characteristic.

REFERENCES

Anness, B. J. (1980) The reduction of dimethyl sulphoxide to dimethyl sulphide during fermentation. J. Inst. Brew. 86:134–137.

Anness, B. J. and Bamforth, C. W. (1982) Dimethyl sulphide—a review. J. Inst. Brew. 88:244–252.

Anness, B. J., Bamforth, C. W. and Wainwright, T. (1979) The measurement of dimethyl sulphoxide in barley and malt and its reduction to dimethyl sulphide by yeast. J. Inst. Brew. 85:346–349.

Atkin, L., Stone, I. and Gray, P. P. (1947) Use of the specific gravity gradient tube for brewery control. Wallerstein Commun. 11:281–287

Baichwal, V. R.; Cunningham, T. S.; Gatzek, P. R. and Kohlhaw, G. B. (1983) Leucine biosynthesis in yeast. Identification of two genes (LEU4, LEU5) that affect α-isopropylmalate synthase activity and evidence that LEU1 and LEU2 gene expression is controlled by α-isopropylmalate and the product of a regulatory gene. Current Genetics 7:369–377.

Bamforth, C. W. (1980) Dimethyl sulphoxide reductase of Saccharomyces spp. FEMS Microbiol. Lett. 7:55–59.

Bamforth, C. W. and Anness, B. J. (1979) Dimethyl Sulphoxide reduction by yeast. Society for General Microbiology Quarterly 6:160.

Bamforth, C. W. and Anness, B. J. (1981) The role of dimethyl sulphoxide reductase in the formation of dimethyl sulphide during fermentations. J. Inst. Brew. 87:30–34.

Bilous, P. T., Cole, S. T., Anderson, W. F. and Weiner, J. H. (1988) Nucleotide sequence of the dmsABC operon encoding the anaerobic dimethyl sulphoxide reductase of *Escherichia coli*. Mol. Microbiol. 2:785–795.

Black, S., Harte, E. M., Hudson, B. and Wartofsky, L. (1960) A specific enzymatic reduction of L (−) methionine sulphoxide and a related nonspecific reduction of disulfides. J. Biol. Chem. 235:2910–2916.

Botstein, D., Falco, S. C., Stewart, S. E., Brennan, M., Scherer, S., Stinchcomb, D. T., Struhl, K. and Davis, R. W. (1979), Sterile host yeasts (SHY): a eukaryotic system of biological containment for recombinant DNA experiments. Gene 8:17–24.

Botstein, D. and R. W. Davis (1982). Principles and practice of recombinant DNA research with yeast. In: Molecular Biology of the Yeast Saccharomyces. Metabolism and Gene Expression. J. N. Strathern, E. W. Jones & J. R. Broach eds. Cold Spring Harbor Laboratory. Cold Spring Harbor, N.Y., 11B:607–636.

Breton, A. and Surdin-Kerjan, Y. (1977) Sulfate uptake in *Saccharomyces cerevisiae*: biochemical and genetic study. J. Bacteriol. 132:3017–3021.

Briza, P., Winkler, G., Kalchhauser, H. and Breitenbach, M. (1986) Dityrosine is a prominent component of the yeast ascospore wall. A proof of its structure. J. Biol. Chem. 261:4288–4294.

Casey, G. P. (1986) Cloning and analysis of two alleles of the ILV3 gene from *Saccharomyces carlsbergensis*. Carlsberg Res. Commun. 51:327–341.

Cherest, H., Davidian, J.-C., Thomas, D., Benes, V., Ansorge, W. and Surdin-Kerjan, Y. (1997) Molecular characterization of two high affinity sulfate transporters in *Saccharomyces cerevisiae*. Genetics 145 (3): 627–635.

Cherest, H. and Surdin-Kerjan, Y. (1992) Genetic analysis of a new mutation conferring cysteine auxotrophy in *Saccharomyces cerevisiae*: updating of the sulfur metabolism pathway. Genetics 130:51–58.

Cherest, H., Thao, N. N. and Surdin-Kerjan, Y. (1985) Transcriptional regulation of the MET3 gene of *Saccharomyces cerevisiae*. Gene 34:269–281.

Dickenson, C. J. (1983) Cambridge Prize Lecture: Dimethyl sulphide—its origin and control in brewing. J. Inst. Brew. 89:41–46.

Dickenson, C. J. and Anderson, R. G. (1981) The relative importance of S-methylmethionine and dimethyl sulphoxide as precursors of dimethyl sulphide in beer. Proc. Eur. Brew. Conv. Congr., Copenhagen, pp. 413–420.

Dickinson, J. R., Lanterman, M. M., Danner, D. J., Pearson, B. M., Sanz, P., Harrison, S. J. and Hewlins, M. J. E. (1997) A $^{13}$C nuclear magnetic resonance investigation of the metabolism of leucine to isoamyl alcohol in *Saccharomyces cerevisiae*. J. Biol. Chem. 272:26871–26878.

Drain, P. and Schimmel, P. (1986) Yeast LEU5 is a PET-like gene that is not essential for leucine biosynthesis Mol Gen Genet. 204:397–403.

Drain, P. and Schimmel, P. (1988) Multiple genes that determine activity for the first step of leucine biosynthesis in *Saccharomyces cerevisiae*. Genetics 119:13–20.

E. B. C. Analytica Microbiologica (1977) J. Inst. Brew. 83:109–118.

Elskens, M. T., Jaspers, C. J. and Penninckx, M. J. (1991) Glutathione as an endogenous sulphur source in the yeast *Saccharomyces cerevisiae*. J. Gen. Microbiol. 137:637–644.

Friden, P and Schimmel, P. (1988) LEU3 of *Saccharomyces cerevisiae* activates multiple genes for branched-chain amino acid biosynthesis by binding to a common decanucleotide core sequence. Mol. Cell. Biol. 8:2690–2697.

Fujii, T., Iwamatsu, A., Yoshimoto, H., Minetoki, T., Bogaki, T. and Nagasawa, N. (1993) European patent application 0 574 941 A3.

Fujii, T., Yoshimoto, H., Nagasawa, N., Bogaki, T., Tamai, Y. and Hamachi, M. (1996a) Nucleotide sequences of alcohol acetyltransferase genes from lager brewing yeast, *Saccharomyces carlsbergensis*. Yeast 12:593–598.

Fujii, T., Yoshimoto, H. and Tamai, Y. (1996b) Acetate ester production by *Saccharomyces cerevisiae* lacking the ATF1 gene encoding the alcohol acetyltransferase. J. Ferment. Bioeng. 81:538–542.

Gibson, R. M. and Large, P. J. (1985) The influence of assimilable nitrogen compounds in wort on the ability of yeast to reduce dimethyl sulphoxide. J. Inst. Brew. 91:401–405.

Gietz, D., St. Jean, A., Woods, R. A. and Schiestl, R. H. (1992) Improved method for high efficiency transformation of intact yeast cells. Nucl. Acids Res. 20:1425.

Gjermansen, C. and Sigsgaard, P. (1981) Construction of a hybrid brewing strain of *Saccharomyces carlsbergensis* by mating of meiotic segregants. Carlsberg Res. Commun. 46:1–11.

Hadfield, C. (1994) Construction of cloning and expression vectors, pp. 17–48 in: Molecular Genetics of Yeast. A practical approach. Johnston, J.R. (ed.). Oxford University Press, Oxford, UK.

Hadfield, C., Jordan, B. E., Mount, R. C., Pretorius, G. H. J. and Burbak, E. (1990) G418-resistance as a dominant marker and reporter for gene expression in *Saccharomyces cerevisiae*. Curr. Genet. 18:303–313.

Hansen, J. and Kielland-Brandt, M. C. (1994) *Saccharomyces carlsbergensis* contains two functional MET2 alleles similar to homologues from *S. cerevisiae* and *S. monacensis*. Gene 140:33–40.

Hansen, J., Cherest, H and Kielland-Brandt, M. C. (1994) Two divergent MET10 genes, one from *Saccharomyces cerevisiae* and one from *Sacchrommyces carlsbergensis*, encode the α subunit of sulfite reductase and specify potential binding sites for FAD and NADPH. J. Bacteriol. 176:6050–6058.

Hansen, J. and Kielland-Brandt, M. C. (1996a) Inactivation of MET2 in brewer's yeast increases the level of sulfite in beer. J. Biotechnol. 50:75–87.

Hansen, J. and Kielland-Brandt, M. C. (1996b) Inactivation of MET10 in brewer's yeast specifically increases $SO_2$ formation during beer production. Nature Biotechnol. 14:1587–1591.

Hoffman, C. S. and Winston, F. (1987) A ten-minute DNA preparation from yeast efficiently releases autonomous plasmids for transformation of *Escherichia coli*. Gene. 57:267–272.

Hu, Y., Cooper, T. G. and Kohlhaw, G. B. (1995) The *Saccharomyces cerevisiae* Leu3 protein activates expression of GDH1, a key gene in nitrogen assimilation. Mol. Cell. Biol. 15:52–57.

Johannesen, P. F. 1994. Increasing the flux in the sulfur assimilatory pathway. Overproduction of MET3, MET14 and MET16 in *Saccharomyces cerevisiae*. Thesis, University of Copenhagen, Copenhagen.

Kielland-Brandt, M. C., Nilsson-Tillgren, T., Gjermansen, C., Holmberg, S. and Pedersen, M. B. (1995) Genetics of brewing yeasts. In: Wheals, A. E., Rose, A. H. and Harrison, J. S., eds.:The Yeasts, $2^{nd}$ edn., Vol. 6., Academic Press, London, pp. 223–254.

Kispal G., Steiner H., Court D. A., Rolinski, B. and Lill, R. (1996) Mitochondrial and cytosolic branchez chain amino acid. transaminases from yeast, homologs of the myc oncogene-regulated Eca39 protein J. Biol. Chem. 271:24458–24464.

Kohlhaw, G. B. (1988) Methods in Enzymology 166:414–435, Academic Press, Inc.

Korch, C., Mountain, H. A. and Byström, A. S. (1991) Cloning, nucleotide sequence and regulation of MET14, the gene encoding the APS kinase of *Saccharomyces cerevisiae*. Mol. Gen. Genet. 229:96–108.

Langin, T., Faugeron, G., Goyon, C., Nicolas, A. and Rossignol, J.-L. (1986) The MET2 gene of *Saccharomyces cerevisiae*: molecular cloning and nucleotide sequence. Gene 49:283–293.

Lee S., Villa, K., and Patino H. (1995) Yeast strain development for enhanced production of desirable alcohols/esters in beer. J. Am. Soc. Brew. Chem. 53:153–156.

Leemans, C., Dupire, S. and Macron, J.-Y. (1993) Relation between wort DMSO and DMS concentration in beer. Proc. Eur. Brew. Conv. Congr., Oslo, pp. 709–716.

Lowe, L. E. and Dreyer, T. 1997. Quantitation of total sulphur dioxide in beer by automated headspace gas chromatography. Proc. Eur. Brew. Conv. Congr., Maastricht, pp. 649–654.

Malcorps, P. and Dufour, J.-P. (1992) Short-chain and medium-chain aliphatic-ester synthesis in *Saccharomyces cerevisiae*. Eur. J. Biochem. 210:1015–1022.

Meilgaard, M. (1975) Flavor chemistry of beer: Part II: Flavor and threshold of 239 aroma volatiles. MBAA Tech. Quart. 12:151–168.

Minetoki, T., Bogaki, T., Iwamatsu, A., Fujii, T. and Hamachi, M. (1993) The purification, properties and internal peptide sequences of alcohol acetyltransferase isolated from *Saccharomyces cerevisiae* kyokai No. 7 . Biosci. Biotech. Biochem. 57:2094–2098.

Moskovitz, J., Weissbach, H. and Brot, N. (1996) Cloning and expression of a mammalian gene involved in the reduction of methionine sulfoxide residues in proteins. Proc. Natl. Acad. Sci. U.S.A. 93:2095–2099.

Moskowitz, J., Berlett, B. S., Poston, J. M. and Stadtman, E. R. (1997) The yeast peptide-methionine sulfoxide reductase functions as an antioxidant in vivo. Proc. Natl. Acad. U.S.A. 94:9585–9589.

Mountain, H. A., Byström, A. S., Larsen, J. T. and Korch, C. (1991) Four major transcriptional responses in the methionine/threonine biosynthetic pathway of *Saccharomyces cerevisiae*. Yeast 7:781–803.

Nagami, K., Takahashi, T., Nakatani, K. and Kumada, J. (1980) Hydrogen sulfide in brewing. MBAA Tech. Quart. 17:64–68.

Nagasawa, N., Bogaki, T., Iwamatsu, A. and Kumagai, C. (1996) NCBI database, Accession No. D86325.

Nishimura, H., Kawasaki, Y., Kaneko, Y., Nosaka, K. and Iwashima, A. (1992) A positive regulatory gene, THI3, is required for thiamine metabolism in *Saccharomyces cerevisiae*. J. Bacteriol. 174:4701–4706.

Omura, F. and Shibano, Y. (1995) Reduction of hydrogen sufide production in brewing yeast by constitutive expression of MET25 gene. J. ASBC 53:58–62.

Orr-Weaver, T. L., Szostak, J. W. and Rothstein, R. J. (1981) Yeast transformation: A model system for the study of recombination. Proc. Natl. Acad. Sci. USA 78:6354–6358.

Pedersen, M. B. (1986) DNA sequence polymorphisms in the genus Saccharomyces. IV. Homoeologous chromosomes III of *Saccharomyces bayanus, S. carlsbergensis*, and *S. uvarum*. Carlsberg Res. Commun. 51:185–202.

Pedersen, M. B. (1988) The use of nucleotide sequence polymorphisms and DNA karyotyping in the identication of brewer's yeast strains and in microbiological control. In: Linskens, H. F. and Jackson, J. F. (eds.) Modern methods of plant analysis 7:180–194 Springer-Verlag. Berlin.

Porqué, P. G., Baldesten, A. and Reichard, P. (1970) The involvement of the thioredoxin system in the reduction of methionine sulfoxide and sulfate. J. Biol. Chem. 245:2371–2374.

Rahman, M. A., Nelson, H., Weissbach, H. and Brot, N. (1992) Cloning, sequencing, and expression of the *Escherichia coli* peptide methionine sulfoxide reductase gene. J. Biol. Chem. 267:15549–15551.

Ramos, C. and Calderon, I. L. (1992) Overproduction of threonine by *Saccharomyces cerevisiae* mutants resistant to hydroxynorvaline. Appl. Env. Microbiol. 58:1677–1682.

Ramos-Jeunehomme, C., de Keyser, L. and Masschelein, C. A. (1979) Formation de substances aromatiques et cinetiques d'absorption des acides amines do mout. Proc. Eur. Brew. Conv. Congr., Berlin, pp. 505–519.

Rikkerink, E. H. A., Magee, B. B. and Magee, P. T. (1988) Opaquewhite phenotype transition: a programmed morphological transition in *Candida albicans*. J. Bacteriol. 170:895–899.

Rothstein, R. (1991) Targeting, Disruption, Replacement, and allele rescue: Integrative DNA transformation in yeast. Meth. Enzymol. 194:281–301.

Sambrook, J., Fritsch, E. F. and Maniatis, T. (1989) Molecular cloning. A laboratory manual. Cold Spring Harbor Laboratory Press, Cold Spring Harbor, N.Y.

Sangsoda, S., Cherest, H. and Surdin-Kerjan, Y. (1985) The expression of the MET25 gene of *Saccharomyces cerevisiae* is regulated transcriptionally. Mol. Gen. Genet. 200:407–414.

Satoh, T. and Kurihara, F. N. (1987) Purification and properties of dimethylsulfoxide reductase containing a molybdenom cofactor from a photodenitrifier, *Rhodopseudomonas sphaeroides* f.s. denitrificans. J. Biochem. (Tokyo) 102:191–197.

Schaeffer, A. B. and Fulton, M. (1933) A simplified method of staining endospores. Science 77:194.

Scherer, S. and Davis, R. W. (1979) Replacement of chromosome segments wih altered DNA sequences constructed in vitro. Proc. Natl. Acad. Sci. USA 76:4951–4955.

Schiestl, R. H. and Gietz, R. D. (1989) High efficiency transformation of intact yeast cells using single stranded nucleic acids as a carrier. Curr. Genet. 16:339–346.

Schuler, G. D., Altschul, S. F. and Lipman, D. J. (1991) A workbench for multiple alignment construction and analysis. Proteins: Structure, Function and Genetics 9:180–190.

Schwartz, D. C. and Cantor, C. R. (1984) Separation of yeast chromosome-sized DNAs by pulsed field gradient gel electrophoresis. Cell 37:67–75.

Sherman, F. (1991) Getting started with yeast. In: C. Guthrie and G. R. Fink (eds.), Methods in Enzymology 194: Guide to Yeast Genetics and Molecular biology. Academic Press Inc., San Diego, Calif., pp. 3–21.

Sherman, F., Fink, G. R. and Hicks, J. B. (1979) Methods in Yeast Genetics. Cold Spring Harbor Laboratory, Cold Spring Harbor, N.Y. 11724, pp 61–64.

Sigsgaard, P. and Rasmussen, J. N. (1985) Screening of the brewing performance of new yeast strains. J. Am. Soc. Brew. Chem. 43:104–108.

Sikorski, R. S. and Hieter, P. (1989) A system of shuttle vectors and yeast host strain designed for efficient manipulation of DNA in *Saccharomyces cerevisiae*. Genetics 122:19–27.

Singer, R. A., Johnston, C. G. and Bedard, D. (1978) Methionine analogs and cell division regulation in the yeast *Saccharomyces cerevisiae*. Proc. Natl. Acad. USA 75:6083–6087

Takahashi, T., Nagami, K., Nakatani, K. and Kumada, J. (1980) Hydrogen sulfide in brewing—II. MBAA Tech. Quart. 17:210–214.

Tezuka, H., Mori, T., Okumara, Y., Kitabatake, K. and Tsumura, Y. (1992) Cloning of a gene suppressing hydrogen sulfide production by *Saccharomyces cerevisiae* and its expression in a brewing yeast. J. Am. Soc. Brew. Chem. 50:130–133.

Thomas, D., Barbey, R. and Surdin-Kerjan, Y. (1990) Geneenzyme relationship in the sulfate assimilation pathway of *Saccharomyces cerevisiae*. Study of the 3'-phosphoadenylylsulfate reductase structural gene. J. Biol. Chem. 265:15518–15524.

Thomas, D., Barbey, R., Henry, D. and Surdin-Kerjan, Y. (1992) Physiological analysis of mutants of *Saccharomyces cerevisiae* impaired in sulphate assimilation. J. Gen. Microbiol. 138:2021–2028.

Thomas, D., Cherest, H. and Surdin-Kerjan, Y. (1989) Elements involved in S-adenosylmethionine-mediated regulation of the *Saccharomyces cerevisiae* MET25 gene. Mol. Cell. Biol. 9:3292–3298.

Weiner, J. H., Rothery, R. A., Sambasivarao, D. and Trieber, C. A. (1992) Molecular analysis of dimethylsulfoxide reductase: a complex iron-sulfur molybdoenzyme of *Escherichia coli*. Biochim. Biophys. Acta 1102:1–18.

Yamamoto, I., Wada, N., Ujiiye, T., Tachibana, M., Matsuzaki, M., Kajiwara, H., Watanabe, Y., Hirano, H., Okubo, A., Satoh, T. and Yamazaki, S. (1995) Cloning and nucleotide sequence of the gene encoding dimethyl sulfoxide reductase from *Rhodopseudomonas sphaeroides* f.sp. denitrificans. Biosci. Biotech. Biochem. 59:1850–1855.

Yanisch-Perron, C., Vieria, J., Messing, J. (1985) Improved M13 phage cloning vectors and host strains: nucleotide sequence of the M13mp18 and pUC19 vectors. Gene 33:103–119.

Yoshimoto, H., Momma, T., Fujiwara, D., Nagasawa, N. and Tamai, Y. (1996a) Cloning and characterization of the ATF2 gene encoding alcohol acetyltransferase in the bottom fermenting yeast *Saccharomyces pastorianus*. NCBI database Accession No. D86480.

Yoshimoto, H., Momma, T., Fujiwara, D., Sone, H. and Tamai, Y. (1996b) Characterization of the ATF genes encoding alcohol acetyltransferase in the bottom fermenting yeast *Saccharomyces pastorianus*. Abstract. 1996 Yeast Genetics and Molecular Biology Meeting. University of Wisconsin. August 6–11. p. 257.

Zinder, S. H. and Brock, T. D. (1978a) Dimethyl sulphoxide reduction by micro-organisms. J. gen. Microbiol. 105:335–342

Zinder, S. H. and Brock, T. D. (1978b) Dimethyl sulfoxide as an electron acceptor for anaerobic growth. Arch. Microbiol. 116:35–40.

What is claimed is:

1. A genetically modified yeast strain in which all copies of the MET14 gene are inactivated, such that said strain, relative to its parent strain, has a reduced sulfite level or lacks production of sulfite during production of a fermented beverage.

2. A yeast strain according to claim 1 which, during production of a fermented beverage, produces less than 5 ppm sulfite in the beverage.

3. A yeast strain according to claim 2 which is substantially incapable of producing sulphite.

4. A yeast strain according to claim 1 which is selected from the group consisting of *Saccharomyces carsbergensis* and *Saccharomyces cerevisiae*.

5. A yeast strain according to claim 4 which is a *Saccharomyces carlsbergensis* strain selected from the group consisting of PFJ501 and PFJ514.

6. A yeast strain according to claim 1 which is further genetically modified to have under fermentation conditions, relative to its parent strain, (i) a reduced level or no production of a fusel alcohol and an ester thereof and/or (ii) an altered production of at least one of hydrogen sulfide, a thiol or a thioester and/or (iii) a reduced capability or no capability to produce dimethyl sulfide from dimethyl sulfoxide.

* * * * *

```
                         SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 1:

GCTCTAGAGC ATTGGAGTTG GTTATGCG                                    28

(2) INFORMATION FOR SEQ ID NO: 2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 2:

GCGGATCCCC GACCAGAAGA CGGTTGAAGA ATGTGC                           36

(2) INFORMATION FOR SEQ ID NO: 3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear
```

(xi) SEQUENCE DESCRIPTION: SEQ ID NO: 3:

GCGGATCCGC ACATTCTTCA ACCGTCTTCT GGTCGG 36

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 4:

GCTCTAGAAT GGCTACTAAT ATTACT 26

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 5:

GCTCTAGAAG TAATATTAGT AGCCAT 26

(2) INFORMATION FOR SEQ ID NO: 6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 6:

GCGGATCCTG TTCATGATTT CCGAAC 26

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 7:

GCGGATCCGG AGTCGGTACT AAATATC 27

(2) INFORMATION FOR SEQ ID NO: 8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 8:

GCGGATCCGA AAGGTGGCCT ATC 23

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
        (xi) SEQUENCE DESCRIPTION: SEQ ID NO: 9:

GCGAATTCCC ATCGCAAACT GGGG                                            24

(2) INFORMATION FOR SEQ ID NO: 10:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO: 10:

GCGGATCCGT CGAGAACATC TGCG                                            24

(2) INFORMATION FOR SEQ ID NO: 11:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO: 11:

GCTCTAGAGC TTGTGCACTG GAAC                                            24

(2) INFORMATION FOR SEQ ID NO: 12:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO: 12:

GCAAGCTTCT CTCATGGAAT CCTG                                            24

(2) INFORMATION FOR SEQ ID NO: 13:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (xi) SEQUENCE DESCRIPTION: SEQ ID NO: 13:

GGTAAAGCTT GGCGAGTCGA GAAAGGAAAT C                                    31

(2) INFORMATION FOR SEQ ID NO: 14:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (xi) SEQUENCE DESCRIPTION: SEQ ID NO: 14:

GGTATCTAGA ATCGATGGTT TTTGAAATAA GCGACGAC                             38

(2) INFORMATION FOR SEQ ID NO: 15:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (xi) SEQUENCE DESCRIPTION: SEQ ID NO: 15:
```

```
GGTAGGATCC CATTATCTGA GAGAAATGTA G                                         31

(2) INFORMATION FOR SEQ ID NO: 16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 16:

GGTAGAATTC GTCGCCTGGT TAAAGGCTAA C                                         31

(2) INFORMATION FOR SEQ ID NO: 17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 17:

ATCCTTAAGC TGTAGAAATT TGTGAAGCTG TTAAAAAGGC                                40

(2) INFORMATION FOR SEQ ID NO: 18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 18:

AATCTGTCGA CACCGCAACC ACGGTCATTG TGACAATGCG                                40

(2) INFORMATION FOR SEQ ID NO: 19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 19:

CTTGTCGACG CGCTGATCGT GTAGAAGGTT GTCTATTTGG                                40

(2) INFORMATION FOR SEQ ID NO: 20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 20:

CAGCTTAAGG ATCCAATGGT AAGTATGGAA TTCTCCACCG                                40

(2) INFORMATION FOR SEQ ID NO: 21:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 21:
```

```
AGGCTGAGCT CCTCCTGGAA TGTTAAGACT TTCTC                              35

(2) INFORMATION FOR SEQ ID NO: 22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 22:

GGGTAGCAAA ACTGTCCAGA GC                                            22

(2) INFORMATION FOR SEQ ID NO: 23:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 23:

GCTCTGGACA GTTTTGCTAC CCATGTGCGA TCGTGCCATC GGG                     43

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 24:

AGATCTCTGC AGCTAATCAA ATCAATTAAT                                    30

(2) INFORMATION FOR SEQ ID NO: 25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 25:

GCACGCGTCG ACCTACATTG AACTCTGTAG GCCACCG                            37

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 26:

CTCCATGACT TCTCTGTATT CTGG                                          24

(2) INFORMATION FOR SEQ ID NO: 27:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO: 27:

CCAGAATACA GAGAAGTCAT GGAGCGGCTC AACGTTGGA GGTTCGC                  47
```

(2) INFORMATION FOR SEQ ID NO: 28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 28:

GAGCAGCCAC GGCATGCATC GACT                                    24

(2) INFORMATION FOR SEQ ID NO: 29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 29:

AGCTAGTCTA GAGTGTGAGG ACTACTCATT GGCTTG                      36

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 30:

ACTGCACTGT ACTCAGGTTG TTCA                                    24

(2) INFORMATION FOR SEQ ID NO: 31:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO: 31:

TGAACAACCT GAGTACAGTG CAGTCGCAGA TTGCCGCTCA CAACTACC          48

(2) INFORMATION FOR SEQ ID NO: 32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 32:

AGCTGCGAGC TCACACGACA TAATCATATT GTCG                          34

(2) INFORMATION FOR SEQ ID NO: 33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 33:

AGCTAGTCTA GATTGAACAT TGATCAATGT GAA                           33

(2) INFORMATION FOR SEQ ID NO: 34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 34:

CCATCTTGCC GGTAATACAA TA                                          22

(2) INFORMATION FOR SEQ ID NO: 35:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 35:

TGTATTACCG GCAAGATGGC CACTTATTGC ACATTATCAT                40

(2) INFORMATION FOR SEQ ID NO: 36:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO: 36:

AGCTGCGAGC TCCACTTACT TACCTTACAC ACGTCGTT                  38

(2) INFORMATION FOR SEQ ID NO: 37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 37:

AGCTAGTCTA GAAGCGTACT ACTCTAGCGA AGAGTA                    36

(2) INFORMATION FOR SEQ ID NO: 38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 38:

CAGTGTAGTC TCGATCATAG TCAA                                      24

(2) INFORMATION FOR SEQ ID NO: 39:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO: 39:

TTGACTATGA TCGAGACTAC ACTGGTCGAA TACTACTATG ACCGCTT        47

(2) INFORMATION FOR SEQ ID NO: 40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 40:

```
TGTACGAGCT CGGCCGAGCT ATAC                                          24
```

(2) INFORMATION FOR SEQ ID NO: 41:

(i) SEQUENCE CHARACTERISTICS:
        (A) LENGTH: 1160 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 41:

```
GGATCCGAAA GGTGGCCTAT CAAAACAAAT TAACTTCCAC ATAACTGGAA GGCAGCAAAG      60
ATATGTCAGC AAAGACATGT TAGCTTGGTA GTGAAGTTTC TTGTTTTTTA CCTACAAAAC     120
GCCCCGCGCT GTTTTCTCAA TGTTGGAACA AAAAGCGTGC CACTAATTCC ACGTGATTAA     180
TGTCTGCAAG CCACCCCAAA AATTGTGGCT AGTATAGAAG ATGATGAACT CAACATTACT     240
TTAATTTCAT GAATTTTCTG AGGGCGTGTG TATAAAACGC AGATGTTCTC GACAACTTTA     300
CTGTACAAAC TTTACTCTTC TGCTGTAGCT AAATTTTAAA ATGAGTAGGA ACATTTTCGT     360
GAAATTCATT GAAACAAATG GCTACTAATA TCACTTGGCA TCCAAATCTT ACCTACGACG     420
AACGTAAGGA ATTAAGAAAG CAAGACGGCT GTACCGTTTG GTTGACCGGT CTAAGTGCGT     480
CAGGAAAAAG TACAATAGCT TGTGCACTGG AACAATTACT GCTTCAAAAA AACTTATCTG     540
CTTATAGGTT AGATGGTGAT AACATTCGTT TTGGTTTGAA TAAGGATTTG GCTTCTCAG      600
AAAAGGACAG AAATGAAAAC ATTCGTAGAA TTAGTGAAGT ATCCAAGCTA TTCGCTGATT     660
CGTGTGCTGT ATCCATCACT TCATTTATTT CCCCATACAG AGTCGATAGA GACAGAGCCC     720
GTGATTTACA TAAGGAAGCA GGCTTGAAGT TCATTGAAAT TTTTGTTGAT GTTCCATTAG     780
AAGTCGCTGA GCAAAGAGAC CCTAAGGGTT TGTATAAGAA AGCCAGAGAA GGTGTGATTA     840
AAGAGTTCAC TGGTATTTCA GCTCCTTACG AAGCTCCAAA GGCCCCAGAG TTGCATTTAA     900
GAACTGACCA AAAGACTGTT GAAGAATGTG CTGCTATCAT TTATGAGTAC CTGGTCAATG     960
AGAAGATTAT CCGGAAGCAT CTATAAATCT TATAAATTGC ATTTAATGAT ATAAAAGATG    1020
TATAATAGAA AACGTATTTA TTTAAAAGCC CATTCAAGAG CATTGAAAAC TGTAAATAAT    1080
GAGGAGGATG GTATAATAAA TGGTTTTAAA GTTTCACACA CTGTATCCTA TATTAGATAT    1140
TTAGTACCGA CTCCGGATCC                                               1160
```

(2) INFORMATION FOR SEQ ID NO: 42:

(i) SEQUENCE CHARACTERISTICS:
        (A) LENGTH: 619 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO: 42:

Met Val Lys Glu Ser Ile Ile Ala Leu Ala Glu His Ala Ala Ser Arg

-continued

```
  1               5                    10                   15
Ala Ser Arg Val Ile Pro Pro Val Lys Leu Ala Tyr Lys Asn Met Leu
            20                  25                  30

Lys Asp Pro Ser Ser Lys Tyr Lys Pro Phe Asn Ala Pro Lys Leu Ser
            35                  40                  45

Asn Arg Lys Trp Pro Asp Asn Arg Ile Thr Arg Ala Pro Arg Trp Leu
            50                  55                  60

Ser Thr Asp Leu Arg Asp Gly Asn Gln Ser Leu Pro Asp Pro Met Ser
65                      70                  75                  80

Val Glu Gln Lys Lys Glu Tyr Phe His Lys Leu Val Asn Ile Gly Phe
                85                  90                  95

Lys Glu Ile Glu Val Ser Phe Pro Ser Ala Ser Val Cys Leu Phe Asp
                100                 105                 110

Phe Thr Arg Tyr Ala Val Glu Asn Ala Pro Asp Asp Val Ser Ile Gln
            115                 120                 125

Cys Leu Val Gln Ser Arg Glu His Leu Ile Lys Arg Thr Val Glu Ala
            130                 135                 140

Leu Thr Gly Ala Lys Lys Ala Thr Ile His Thr Tyr Leu Ala Thr Ser
145                 150                 155                 160

Asp Met Phe Arg Glu Ile Val Phe Asn Met Ser Arg Glu Glu Ala Ile
                165                 170                 175

Ser Lys Ala Val Glu Ala Thr Lys Leu Val Arg Lys Leu Thr Lys Asp
                180                 185                 190

Asp Pro Ser Gln Gln Ala Thr Arg Trp Ser Tyr Glu Phe Ser Pro Glu
            195                 200                 205

Cys Phe Ser Asp Thr Pro Gly Glu Phe Ala Val Glu Ile Cys Glu Ala
            210                 215                 220

Val Lys Lys Ala Trp Glu Pro Thr Glu Glu Asn Pro Ile Ile Phe Asn
225                 230                 235                 240

Leu Pro Ala Thr Val Glu Val Ala Ser Pro Asn Val Tyr Ala Asp Gln
                245                 250                 255

Ile Glu Tyr Phe Ala Thr His Ile Thr Glu Arg Glu Lys Val Cys Ile
                260                 265                 270

Ser Thr His Cys His Asn Asp Arg Gly Cys Gly Val Ala Ala Thr Glu
            275                 280                 285

Leu Gly Met Leu Ala Gly Ala Asp Arg Val Glu Gly Cys Leu Phe Gly
290                 295                 300

Asn Gly Glu Arg Thr Gly Asn Val Asp Leu Val Thr Val Ala Met Asn
305                 310                 315                 320

Met Tyr Thr Gln Gly Val Ser Pro Asn Leu Asp Phe Ser Asp Leu Thr
            325                 330                 335

Ser Val Leu Asp Val Val Glu Arg Cys Asn Lys Ile Pro Val Ser Gln
            340                 345                 350

Arg Ala Pro Tyr Gly Gly Asp Leu Val Val Cys Ala Phe Ser Gly Ser
            355                 360                 365

His Gln Asp Ala Ile Lys Lys Gly Phe Asn Leu Gln Asn Lys Lys Arg
            370                 375                 380

Ala Gln Gly Glu Thr Gln Trp Arg Ile Pro Tyr Leu Pro Leu Asp Pro
385                 390                 395                 400

Lys Asp Ile Gly Arg Asp Tyr Glu Ala Val Ile Arg Val Asn Ser Gln
                405                 410                 415

Ser Gly Lys Gly Gly Ala Ala Trp Val Ile Leu Arg Ser Leu Gly Leu
            420                 425                 430
```

-continued

```
Asp Leu Pro Arg Asn Met Gln Ile Glu Phe Ser Ser Ala Val Gln Asp
        435                 440                 445

His Ala Asp Ser Leu Gly Arg Glu Leu Lys Ser Asp Glu Ile Ser Lys
        450                 455                 460

Leu Phe Lys Glu Ala Tyr Asn Tyr Asn Asp Glu Gln Tyr Gln Ala Ile
465                     470                 475                 480

Ser Leu Val Asn Tyr Asn Val Glu Lys Phe Gly Thr Glu Arg Arg Val
                485                 490                     495

Phe Thr Gly Gln Val Lys Val Gly Asp Gln Ile Val Asp Ile Glu Gly
            500                 505                 510

Thr Gly Asn Gly Pro Ile Ser Ser Leu Val Asp Ala Leu Ser Asn Leu
        515                 520                 525

Leu Asn Val Arg Phe Ala Val Ala Asn Tyr Thr Glu His Ser Leu Gly
    530                 535                 540

Ser Gly Ser Ser Thr Gln Ala Ala Ser Tyr Ile His Leu Ser Tyr Arg
545                 550                 555                 560

Arg Asn Ala Asp Asn Glu Lys Ala Tyr Lys Trp Gly Val Gly Val Ser
                565                 570                 575

Glu Asp Val Gly Asp Ser Ser Val Arg Ala Ile Phe Ala Thr Ile Asn
            580                 585                 590

Asn Ile Ile His Ser Gly Asp Val Ser Ile Pro Ser Leu Ala Glu Val
        595                 600                 605

Glu Gly Lys Asn Ala Ala Ala Ser Gly Ser Ala
    610                 615
```